United States Patent

Kertesz et al.

[11] Patent Number: 6,127,402
[45] Date of Patent: Oct. 3, 2000

[54] 5-AROYLPYRROL-2-YLMETHYLARENE DERIVATIVES

[75] Inventors: Denis J. Kertesz, Mountain View, Calif.; Edvige Galeazzi Toscani, Mexico City, Mexico; Deborah C. Reuter; Eric B. Sjogren, both of Palo Alto, Calif.

[73] Assignee: Syntex (U.S.A.) Inc., Palo Alto, Calif.

[21] Appl. No.: 09/275,540

[22] Filed: Mar. 24, 1999

Related U.S. Application Data

[62] Division of application No. 08/864,703, May 28, 1997, Pat. No. 5,952,368.
[60] Provisional application No. 60/018,691, May 30, 1996.
[51] Int. Cl.$^7$ ................... C07D 209/52; A61K 31/403
[52] U.S. Cl. ................ 514/413; 514/299; 514/339; 546/112; 546/276.7; 548/516; 548/468
[58] Field of Search .................. 514/413, 299, 514/339; 548/468, 516; 546/276.7, 112

[56] References Cited

U.S. PATENT DOCUMENTS

| | | | |
|---|---|---|---|
| 3,752,826 | 8/1973 | Carson | 514/427 |
| 5,622,948 | 4/1997 | Dunn et al. | 514/252 |

FOREIGN PATENT DOCUMENTS 0 071 399 A2  9/1983  European Pat. Off. .

*Primary Examiner*—Jane Fan
*Attorney, Agent, or Firm*—Rohan Peries; Rekha Bansal

[57] ABSTRACT

Compounds selected from the group of compounds represented by formula I:

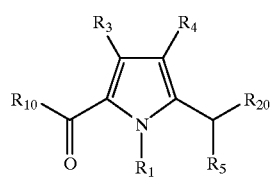

where:

$R_{10}$ is represented by the formula (A), (B), or (C):

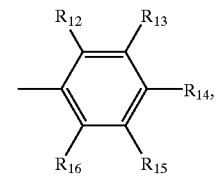

(A)

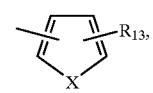

(B)

or

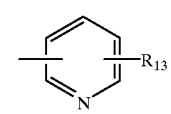

(C)

$R_{20}$ is represented by the formula (U), (V), or (W):

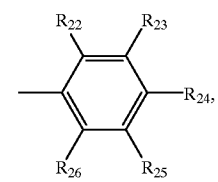

(U)

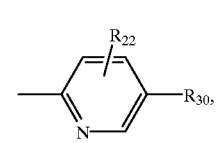

(V)

or

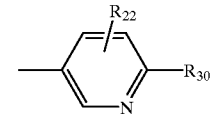

(W)

and the other substituents are as defined in the specification; and their pharmaceutically acceptable salts;
are inhibitors of prostaglandin G/H synthase and are anti-inflammatory and analgesic agents.

17 Claims, No Drawings

5-AROYLPYRROL-2-YLMETHYLARENE DERIVATIVES

CROSS-REFERENCE TO RELATED APPLICATION

This application is a divisional of application Ser. No. 08/864,703, filed May 28, 1997 now U.S. Pat. No. 5,952,368 and also claims the benefit under 35 U.S.C. 119(e) U.S. Provisional Application No. 60/018,691, filed May 30, 1996. The entire disclosure of the prior application is considered as being part of the disclosure of this divisional application and is hereby incorporated by reference therein.

BACKGROUND OF THE INVENTION

1. Field of the Invention

This invention relates to anti-inflammatory and analgesic compounds; especially to certain 5-aroylpyrrol-2-ylmethylarene derivatives, pharmaceutical compositions containing them, methods for their use and methods for preparing these compounds.

2. Description of the Related Art

U.S. Pat. No. 3,752,826 (Carson) discloses 5-aroylpyrrol-2-ylalkanoic acids and derivatives useful as anti-inflammatory agents.

European Patent Application Publication No. 0 071 399 (Syntex (U.S.A.) Inc.) discloses 2-benzyl-5-phenylpyrrolidine derivatives and analogs useful as cardiovascular agents and bronchodilators.

SUMMARY OF THE INVENTION

In a first aspect, this invention provides compounds selected from the group of compounds represented by formula I:

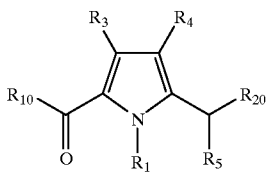

I where:
$R_1$ and $R_5$ are independently H or alkyl, or $R_1$ and $R_5$ together are —(CH$_2$)$_2$— or —(CH$_2$)$_3$—;
$R_3$ and $R_4$ are independently H, halo, alkyl, alkyloxy, or alkylthio;
$R_{10}$ is a group represented by formula (A), (B), or (C):

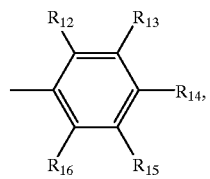

(A)

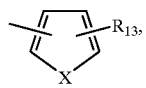

(B)

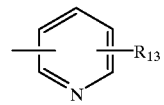

(C)

where:
X is O or S;
$R_{12}$ and $R_{16}$ are independently H, halo, alkyl, alkyloxy, alkylthio, cyano, or hydroxy;
$R_{13}$ and $R_{15}$ are independently H, halo, alkyl, alkyloxy, or alkylthio; and
$R_{14}$ is H, halo, alkyl, haloalkyl, amino, alkylamino, dialkylamino, alkyloxy, hydroxy, alkylthio, alkenyl, alkynyl, cyano, —SO$_2$R$_{17}$ where $R_{17}$ is alkyl, or —SO$_2$NR$_{18}$R$_{19}$ where $R_{18}$ and $R_{19}$ are independently H or alkyl;
provided that at least two of $R_{12}$, $R_{13}$, $R_{14}$, $R_{15}$, and $R_{16}$ are H, and that if only two of $R_{12}$, $R_{13}$, $R_{14}$, $R_{15}$, and $R_{16}$ are H, the non-hydrogen substituents are not all adjacent; or
$R_{12}$, $R_{15}$, and $R_{16}$ are H and $R_{13}$ and $R_{14}$ together are —OCH$_2$O—;
$R_{20}$ is a group represented by formula (U), (V), or (W):

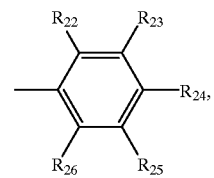

(U)

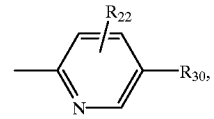

(V)

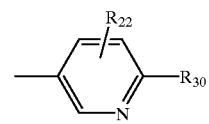

(W)

where:
$R_{22}$ is H, halo, alkyl, cyano, trifluoromethyl, hydroxy, alkyloxy, or —CO$_2$R$_{27}$ where $R_{27}$ is H or alkyl;
one of $R_{23}$, $R_{24}$, and $R_{25}$ is $R_{30}$; and
either all the remaining $R_{23}$, $R_{24}$, $R_{25}$, and $R_{26}$ are H; or one of the remaining $R_{23}$, $R_{24}$, $R_{25}$, and $R_{26}$ is halo, alkyl, cyano, trifluoromethyl, hydroxy, or alkyloxy; and
$R_{30}$ is —OH*, —NHH*, —NH*CHO, —NH*C(X)R$_{31}$, —NH*SO$_2$R$_{31}$, —NH*C(X)NR$_{32}$R$_{33}$, or —NH*SO$_2$NR$_{32}$R$_{34}$;
where:
H* is hydrogen, optionally replaced by an in vivo hydrolyzable protecting group;
$R_{31}$ is alkyl, haloalkyl, hydroxyalkyl, alkenyl, benzyl, aryl, cycloamino, —CH$_2$SO$_2$Me, or —$(CH_2)_nR_{35}$ where n is an integer from 2 to 5 and $R_{35}$ is alkylamino, dialkylamino, cycloamino, alkyloxy, acyloxy, or —$CO_2R_{27}$;

$R_{32}$ is H, alkyl, or —$(CH_2)_nOR_{27}$;

$R_{33}$ is H, alkyl, haloalkyl, aryl, hydroxyalkyl, tetrahydrofuran-2-ylmethyl, —$CH_2CO_2R_{27}$ or —$(CH_2)_nR_{35}$; and $R_{34}$ is H, alkyl, acetyl, hydroxyalkyl, or —$(CH_2)_nR_{35}$;

and their pharmaceutically acceptable salts.

In a second aspect, this invention provides pharmaceutical compositions containing a therapeutically effective amount of a compound of formula I or its pharmaceutically acceptable salt and a pharmaceutically acceptable excipient.

In a third aspect, this invention provides a method of treatment of a disease, in particular inflammatory and autoimmune diseases, in a mammal treatable by administration of a prostaglandin G/H synthase inhibitor, comprising administration of a therapeutically effective amount of a compound of formula I or its pharmaceutically acceptable salt.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms; or a branched or cyclic saturated monovalent hydrocarbon radical of three to six carbon atoms, e.g., methyl, ethyl, propyl, 2-propyl, cyclopropyl, cyclopropylmethyl, pentyl, and the like.

"Alkyloxy" means a radical —OR where R is alkyl, e.g., methoxy, ethoxy, propoxy, 2-propoxy, and the like.

"Alkylthio" means a radical —SR where R is alkyl, e.g., methylthio, butylthio, and the like.

"Acyloxy" means a radical —OC(O)R where R is alkyl, e.g., acetoxy, propionyloxy and the like.

"Alkenyl" means a linear monovalent hydrocarbon radical of two to six carbon atoms or a branched monovalent hydrocarbon radical of three to six carbon atoms, containing a double bond, e.g., ethenyl, propenyl, and the like.

"Alkynyl" means a linear monovalent hydrocarbon radical of two to six carbon atoms or a branched monovalent hydrocarbon radical of three to six carbon atoms, containing a triple bond, e.g., ethynyl, propynyl, butynyl, and the like.

"Halo" means fluoro, bromo, chloro and iodo, preferably fluoro and chloro.

"Haloalkyl" means alkyl substituted with one to three fluorine or chlorine atoms, e.g., —$CH_2Cl$, —$CF_3$, —$CH_2CF_3$, —$CH_2CCl_3$, and the like.

"Alkylamino" means a radical —NHR where R is alkyl, e.g., methylamino, (1-methylethyl)amino, and the like.

"Dialkylamino" means a radical —NRR' where R and R' are independently alkyl, e.g., dimethylamino, methylethylamino, di(1-methylethyl)amino, and the like.

"Cycloamino" means a saturated monovalent, cyclic radical of 5 or 6 ring atoms of which the bonding ring atom is N; one non-adjacent other ring atom is NR (where R is hydrogen or alkyl), O, or C; and the remaining ring atoms are C. Examples include 1-pyrrolidino, 1-piperidino, 1-piperazino, N-methylpiperazino, 4-morpholino, and the like.

"Hydroxyalkyl" means a linear monovalent hydrocarbon radical of two to four carbon atoms or a branched monovalent hydrocarbon radical of three or four carbons substituted with one or two hydroxy groups, provided that: (1) the bonding carbon is unsubstituted, and (2) if two hydroxy groups are present, they are not both on the same carbon atom. Examples include 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Aryl" means a monovalent aromatic hydrocarbon radical of 5 or 6 ring atoms, optionally containing one ring heteroatom selected from NR (where R is H or alkyl), O or S, and optionally mono- or di-substituted independently with —OH, —COOH, alkyl, alkyloxy, alkylthio, fluoro, chloro, —$CF_3$, and cyano; e.g., phenyl, thienyl, pyridyl, furanyl, 3-chlorophenyl, 4-(methylthio) phenyl, and the like.

An "in vivo hydrolyzable protecting group" means a group, replacing an acidic proton (such as a phenolic or amino proton) in a compound of formula I, that is capable of undergoing enzymatic hydrolysis within a living organism to form the unprotected (proton-containing) compound of formula I in vivo. Preferred in vivo hydrolyzable protecting groups are —C(O)R, where R is alkyl, or —C(O)CH(NH$_2$)R", where R" is the side chain of a D or L natural amino acid [e.g., for alanine, R" is methyl; for lysine, R" is —$(CH_2)_4NH_2$]. Preferred R" groups are methyl, isopropyl and benzyl.

"Optional" or "optionally" means that the subsequently described event or circumstance may but need not occur, and that the description includes instances where the event or circumstance occurs and instances in which it does not. For example, "—OH* where H* is optionally replaced by an in vivo hydrolyzable protecting group" means that the in vivo hydrolyzable protecting group may but need not be present, and the description includes situations where —OH* is present as —OH, —OC(O)R, or —OC(O)CH(NH$_2$)R" where —C(O)R and —C(O)CH(NH$_2$)R" are in vivo hydrolyzable protecting groups as defined above.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Me" denotes methyl.

Nomenclature

The naming and numbering of the compounds of this invention is illustrated below. The pyrrole and the side chain of $R_{20}$ nucleus of the compounds of formula I are numbered as follows:

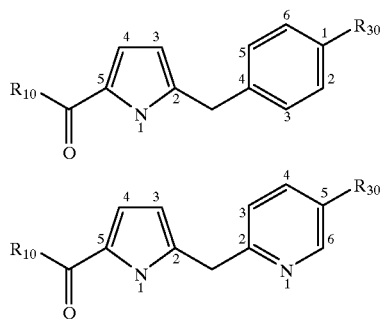

Side chains of the $R_{10}$ substituent are numbered as shown below:

(A)

(B)

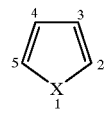

(C)

The pyridine, thiophene, and furan rings can be linked to the pyrrole carbonyl group at any position on the ring other than 1-position. Accordingly, the pyridine ring can be 2-, 3-, or 4-pyridyl, the thiophene ring can be 2- or 3-thienyl, and the furan ring can be 2- or 3-furyl.

The nomenclature used in this application is generally based on the IUPAC recommendations. However, because a strict adherence to these recommendations would result in the names changing substantially when only a single substituent is changed, compounds have been named in a form that maintains consistency of nomenclature for the basic structure of the molecule.

Representative Compounds of this Invention Are as Follows:

Ia. Compounds of formula I where $R_1=R_3=Me$; $R_4=R_{12}=R_{13}=R_{15}=R_{16}=R_{25}=H$, $R_{14}=Cl$; $R_{10}$=group represented by formula (A); $R_{20}$=group represented by formula (U); and $R_{24}=R_{30}=NH^*SO_2R_{31}$, are:

| CPD# | $R_5$ | $R_{22}$ | $R_{23}$ | $R_{26}$ | $R_{31}$ | M. Pt. ° C. |
|---|---|---|---|---|---|---|
| 1 | H | H | H | H | Me | 200.9–202 |
| 2 | H | H | H | H | $CF_3$ | 159.5–160.2 |
| 3 | H | H | H | H | $CH_2CH_3$ | 152.1–152.9 |
| 4 | H | H | H | H | $(CH_2)_2NMe_2.HCl$ | 232.5–232.7 |
| 5 | H | H | H | H | $(CH_2)_2CO_2Me$ | 147.6–148.2 |
| 6 | H | H | H | H | $(CH_2)_2CO_2H$ | 211 |
| 7 | H | H | H | H | $(CH_2)_2OH$ | 132.2–134 |
| 8 | H | H | H | H | $(CH_2)_2$-morpholine.HCl | 243.4–243.7 |
| 9 | H | H | H | H | $CH=CH_2$ | 146.8–147 |
| 10 | H | H | H | H | $CH_2SO_2Me$ | 187–188 |
| 11 | Me | H | H | H | Me | foam |
| 12 | H | Me | H | H | Me | 190–191 |
| 13 | H | $CF_3$ | H | H | Me | 204–206 |
| 14 | H | Cl | H | H | Me | 215–217 |
| 15 | H | $CO_2Me$ | H | H | Me | 197–199 |
| 16 | H | $CO_2H$ | H | H | Me | 248–250 |
| 17 | H | F | H | H | Me | 211–212 |
| 18 | H | OMe | H | H | Me | 164–165 |
| 19 | H | CN | H | H | Me | 204 |
| 20 | H | F | H | H | $CH_2CH_3$ | 151–151.3 |
| 21 | H | H | Me | H | Me | 175–177 |
| 22 | H | H | F | H | Me | 183–185 |
| 23 | H | H | OH | H | Me | 205 |
| 24 | H | H | CN | H | Me | 187 |
| 25 | H | Cl | H | H | $(CH_2)_2OH$ | 159 |
| 26 | H | H | H | H | Me    H*=COMe | 196 |
| 27 | H | F | H | F | Me | 242.8–243.5 | and are named as follows:
1. N-{4-[5-(4-Chlorobenzoyl)-1,4-dimethyl-1H-pyrrol-2-ylmethyl]phenyl}methane-sulfonamide.
2. N-{4-[5-(4-Chlorobenzoyl)-1,4-dimethyl-1H-pyrrol-2-ylmethyl]phenyl}trifluoro-methanesulfonamide.
3. N-{4-[5-(4-Chlorobenzoyl)-1,4-dimethyl-1H-pyrrol-2-ylmethyl]phenyl}ethanesulfonamide.
4. N-{4-[5-(4-Chlorobenzoyl)-1,4-dimethyl-1H-pyrrol-2-ylmethyl]phenyl}-2-(dimethylamino)-etanesulfonamide hydrochloride.
5. N-{4-[5-(4-Chlorobenzoyl)-1,4-dimethyl-1H-pyrrol-2-ylmethyl]phenyl}-2-(methoxycarbonyl) ethanesulfonamide.

6. N-{4-[5-(4-Chlorobenzoyl)-1,4-dimethyl-1H-pyrrol-2-ylmethyl]phenyl}-2-(carboxy)-ethanesulfonamide.
7. N-{4-[5-(4-Chlorobenzoyl)-1,4-dimethyl-1H-pyrrol-2-ylmethyl]phenyl}-2-(hydroxy)-ethanesulfonamide.
8. N-{4-[5-(4-Chlorobenzoyl)-1,4-dimethyl-1H-pyrrol-2-ylmethyl]phenyl}-2-(morpholin-4-yl)ethanesulfonamide hydrochloride.
9. N-{4-[5-(4-Chlorobenzoyl)-1,4-dimethyl-1H-pyrrol-2-ylmethyl]phenyl}ethenesulfonamide.
10. N-{4-[5-(4-Chlorobenzoyl)-1,4-dimethyl-1H-pyrrol-2-ylmethyl]phenyl}-C-(methylsulfonyl)-methanesulfonamide.
11. N-{4-[5-(4-Chlorobenzoyl)-1,4-dimethyl-1H-pyrrol-2-ylethan-1-yl]phenyl}-methanesulfonamide, m/e=430 (M+).
12. N-{3-Methyl-4-[5-(4-chlorobenzoyl)-1,4-dimethyl-1H-pyrrol-2-ylmethyl]phenyl}-methanesulfonamide.
13. N-{3-Trifluoromethyl-4-[5-(4-chlorobenzoyl)-1,4-dimethyl-1H-pyrrol-2-ylmethyl]phenyl}-methanesulfonamide.
14. N-{3-Chloro-4-[5-(4-chlorobenzoyl)-1,4-dimethyl-1H-pyrrol-2-ylmethyl]phenyl}-methanesulfonamide.
15. N-{3-Carboxymethyl-4-[5-(4-chlorobenzoyl)-1,4-dimethyl-1H-pyrrol-2-ylmethyl]phenyl}-methanesulfonamide.
16. N-{3-Carboxy-4-[5-(4-chlorobenzoyl)-1,4-dimethyl-1H-pyrrol-2-ylmethyl]phenyl}-methanesulfonamide.
17. N-{3-Fluoro-4-[5-(4-chlorobenzoyl)-1,4-dimethyl-1H-pyrrol-2-ylmethyl]phenyl}-methanesulfonamide.
18. N-{3-Methoxy-4-[5-(4-chlorobenzoyl)-1,4-dimethyl-1H-pyrrol-2-ylmethyl]phenyl}-methanesulfonamide.
19. N-{3-Cyano-4-[5-(4-chlorobenzoyl)-1,4-dimethyl-1H-pyrrol-2-ylmethyl]phenyl}-methanesulfonamide.
20. N-{3-Fluoro-4-[5-(4-chlorobenzoyl)-1,4-dimethyl-1H-pyrrol-2-ylmethyl]phenyl}ethanesulfonamide.
21. N-{2-Methyl-4-[5-(4-chlorobenzoyl)-1,4-dimethyl-1H-pyrrol-2-ylmethyl]phenyl}-methanesulfonamide.
22. N-{2-Fluoro-4-[5-(4-chlorobenzoyl)-1,4-dimethyl-1H-pyrrol-2-ylmethyl]phenyl}-methanesulfonamide.
23. N-{2-Hydroxy-4-[5-(4-chlorobenzoyl)-1,4-dimethyl-1H-pyrrol-2-ylmethyl]phenyl}-methanesulfonamide.
24. N-{2-Cyano-4-[5-(4-chlorobenzoyl)-1,4-dimethyl-1H-pyrrol-2-ylmethyl]phenyl}-methanesulfonamide.
25. N-{3-Chloro-4-[5-(4-chlorobenzoyl)-1,4-dimethyl-1H-pyrrol-2-ylmethyl]phenyl}-2-(hydroxy)ethanesulfonamide.
26. N-Methoxycarbonyl-N-{4-[5-(4-chlorobenzoyl)-1,4-dimethyl-1H-pyrrol-2-ylmethyl]-phenyl}-methanesulfonamide.
27. N-{3,5-Difluoro-4-[5-(4-chlorobenzoyl)-1,4-dimethyl-1H-pyrrol-2-ylmethyl]phenyl}-methanesulfonamide.

Ib. Compounds of formula I where $R_1$=Me; $R_4$=$R_{13}$=$R_{15}$=$R_{16}$=$R_{23}$=$R_{25}$=H; $R_{14}$=Me; $R_{10}$=is a group represented by formula (A); $R_{20}$=is a group represented by formula (U); and $R_{24}$=$R_{30}$=NH*SO$_2$R$_{31}$, are:

| CPD# | $R_3$ | $R_5$ | $R_{12}$ | $R_{22}$ | $R_{26}$ | $R_{31}$ | M.Pt. °C. |
|---|---|---|---|---|---|---|---|
| 28 | H | H | H | H | H | Me | 138–139 |
| 29 | H | H | H | H | H | (CH$_2$)$_2$OH | foam |
| 30 | H | H | Me | H | H | Me | 147–148 |
| 31 | H | H | H | Cl | H | Me | 137–139 |
| 32 | H | H | H | CF$_3$ | H | Me | 172–174 |
| 33 | H | H | H | Br | H | Me | 160–161 |
| 34 | H | H | H | CN | H | Me | 171–172 |
| 35 | H | H | H | F | H | Me | 164.8–165.3 |

-continued

| CPD# | $R_3$ | $R_5$ | $R_{12}$ | $R_{22}$ | $R_{26}$ | $R_{31}$ | M.Pt. °C. |
|---|---|---|---|---|---|---|---|
| 36 | H | H | H | F | H | (CH$_2$)$_2$OH | foam |
| 37 | H | H | H | Cl | H | (CH$_2$)$_2$OH | 123–125 |
| 38 | Me | H | H | F | H | Me | 200.8–201.6 |
| 39 | Me | H | H | F | H | CH$_2$CH$_3$ | 140.4–141.9 |
| 40 | Me | H | H | CN | H | Me | 204.3–207.4 |
| 41 | H | H | Me | F | H | Me | 159.6–160.0 |
| 42 | H | H | H | F | H | CH(CH$_2$OH)$_2$ | 133.3–133.6 |
| 43 | Me | H | Me | Cl | H | Me | 191.8–192.4 |
| 44 | H | H | H | F | H | (CH$_2$)$_3$OH | 116.7–119.8 |
| 45 | Me | H | Me | CN | H | Me | 203–205.2 |
| 46 | Me | H | H | F | H | (CH$_2$)$_2$OH | 151.5–152.9 |
| 47 | Me | H | H | Cl | H | Me | 208.4–209.4 |
| 48 | Me | H | Me | F | H | (CH$_2$)$_2$OH | 135.4–136.8 |
| 49 | Me | H | Me | F | H | Me | 198.3–199 |
| 50 | H | H | Me | H | H | (CH$_2$)$_2$OH | 63–66 |
| 51 | H | H | H | F | F | (CH$_2$)$_2$OH | 154.2–155.2 |
| 52 | H | H | H | F | F | Me | 205.5–206.2 |
| 53 | H | H | OMe | F | H | (CH$_2$)$_2$OH | 70.5–76 | and are named as follows:

28. N-{4-[5-(4-Methylbenzoyl)-1-methyl-1H-pyrrol-2-ylmethyl]phenyl}methanesulfonamide.
29. N-{4-[5-(4-Methylbenzoyl)-1-methyl-1H-pyrrol-2-ylmethyl]phenyl}-2-(hydroxy)-ethanesufonamide, m/e=412 (M+).
30. N-{4-[5-(4-Methylbenzoyl)-1-methyl-1H-pyrrol-2-ylethan-1-yl]phenyl}methanesulfonamide.
31. N-{3-Cloro-4-[5-(4-methylbenzoyl)-1-methyl-1H-pyrrol-2-ylmethyl]phenyl}-methanesulfonamide.
32. N-{3-Trifluoromethyl-4-[5-(4-methylbenzoyl)-1-methyl-1H-pyrrol-2-ylmethyl]phenyl}-methanesulfonamide.
33. N-{3-Bromo-4-[5-(4-methylbenzoyl)-1-methyl-1H-pyrrol-2-ylmethyl]phenyl}-methanesulfonamide.
34. N-{3-Cyano-4-[5-(4-methylbenzoyl)-1-methyl-1H-pyrrol-2-ylmethyl]phenyl}-methanesulfonamide.
35. N-{3-Fluoro-4-[5-(4-methylbenzoyl)-1-methyl-1H-pyrrol-2-ylmethyl]phenyl}-methanesulfonamide.
36. N-{3-Fluoro-4-[5-(4-methylbenzoyl)-1-methyl-1H-pyrrol-2-ylmethyl]phenyl}-2-(hydroxy)ethanesulfonamide, m/e=430 (M+).
37. N-{3-Chloro-4-[5-(4-methylbenzoyl)-1-methyl-1H-pyrrol-2-ylmethyl]phenyl}-2-(hydroxy)ethanesulfonamide.
38. N-{3-Fluoro-4-[5-(4-methylbenzoyl)-1,4-dimethyl-1H-pyrrol-2-ylmethyl]phenyl}-methanesulfonamide.
39. N-{3-Fluoro-4-[5-(4-methylbenzoyl)-1,4-dimethyl-1H-pyrrol-2-ylmethyl]phenyl}ethanesulfonamide.
40. N-{3-Cyano-4-[5-(4-methylbenzoyl)-1,4-dimethyl-1H-pyrrol-2-ylmethyl]phenyl}-methanesulfonamide.
41. N-{3-Fluoro-4-[5-(2,4-dimethylbenzoyl)-1-methyl-1H-pyrrol-2-ylmethyl]phenyl}-methanesulfonamide.
42. N-{3-Fluoro-4-[5-(4-methylbenzoyl)-1,4-dimethyl-1H-pyrrol-2-ylmethyl]phenyl}-1-(hydroxymethyl)-2-(hydroxy)-ethanesulfonamide.
43. N-{3-Chloro-4-[5-(2,4-dimethylbenzoyl)-1,4-dimethyl-1H-pyrrol-2-ylmethyl]phenyl}-methanesulfonamide.
44. N-{3-Fluoro-4-[5-(4-methylbenzoyl)-1-methyl-1H-pyrrol-2-ylmethyl]phenyl}-3-(hydroxy)propanesulfonamide.
45. N-{3-Cyano-4-[5-(2,4-dimethylbenzoyl)-1,4-dimethyl-1H-pyrrol-2-ylmethyl]phenyl}-methanesulfonamide.
46. N-{3-Fluoro-4-[5-(4-methylbenzoyl)-1,4-dimethyl-1H-pyrrol-2-ylmethyl]phenyl}-2-(hydroxy)ethanesulfonamide.
47. N-{3-Cloro-4-[5-(4-methylbenzoyl)-1,4-dimethyl-1H-pyrrol-2-ylmethyl]phenyl}-methsnesulfonamide.

48. N-{3-Fluoro-4-[5-(2,4-dimethylbenzoyl)-1-methyl-1H-pyrrol-2-ylmethyl]phenyl}-2-(hydroxy)ethanesulfonamide.
49. N-{3-Fluoro-4-[5-(2,4-dimethylbenzoyl)-1,4-dimethyl-1H-pyrrol-2-ylmethyl]phenyl}-methanesulfonamide.
50. N-{4-[5-(2,4-dimethylbenzoyl)-1-methyl-1H-pyrrol-2-ylmethyl]phenyl}-2-(hydroxy)-ethanesulfonamide.
51. N-{3,5-Difluoro-4-[5-(4-methylbenzoyl)-1-methyl-1H-pyrrol-2-ylmethyl]phenyl}-2-(hydroxy)ethanesulfonamide.
52. N-{3,5-Difluoro-4-[5-(4-methylbenzoyl)-1-methyl-1H-pyrrol-2-ylmethyl]phenyl}-methanesulfonamide.
53. N-{3-Fluoro-4-[5-(2-methoxy-4-methylbenzoyl)-1-methyl-1H-pyrrol-2-ylmethyl]phenyl}-2-(hydroxy)ethanesulfonamide.

Ic. Compounds of formula I where R=Me; $R_4=R_5=R_{13}=R_{15}=R_{16}=R_{23}=R_{25}=H$; $R_{14}=H$; $R_{10}$=is a group represented by formula (A); $R_{20}$=is a group represented by formula (U); and $R_{24}=R_{30}=NH^*SO_2R_{31}$, are:

| CPD# | $R_3$ | $R_{12}$ | $R_{22}$ | $R_{26}$ | $R_{31}$ | M.Pt. ° C. |
|---|---|---|---|---|---|---|
| 54 | Me | H | H | H | Me | 149–150 |
| 55 | Me | H | H | H | $(CH_2)_2CO_2Me$ | 121.5–121.9 |
| 56 | Me | H | H | H | $(CH_2)_2CO_2H$ | 181 |
| 57 | Me | H | H | H | $(CH_2)_2OH$ | 158.2–158.6 |
| 58 | Me | H | H | H | $CH_2CH_3$ | 117.7–118.8 |
| 59 | Me | H | Cl | H | Me | 177–179 |
| 60 | Me | H | F | H | Me | 167–168 |
| 61 | Me | H | OMe | H | Me | 133–134 |
| 62 | Me | H | $CF_3$ | H | Me | 170–171 |
| 63 | Me | H | F | H | $(CH_2)_2OH$ | 149–149.3 |
| 64 | H | H | H | H | Me | 137–138 |
| 65 | H | H | F | H | Me | 137.2–137.5 |
| 66 | H | H | F | H | $(CH_2)_2OH$ | foam |
| 67 | Me | H | F | H | Me H*=COMe | 172 |
| 68 | Me | H | F | H | $CH_2CH_3$ | 141.1–143.1 |
| 69 | H | H | Cl | H | $(CH_2)_2OH$ | 149.9–151.1 |
| 70 | H | H | Cl | H | Me | 180.2–181.6 |
| 71 | H | Me | F | H | Me | 178.7–179.2 |
| 72 | H | OMe | F | H | Me | 184.4–184.9 |
| 73 | H | OMe | F | H | $(CH_2)_2OH$ | foam |
| 74 | H | F | F | H | Me | 140–141 |
| 75 | H | H | F | F | Me | 192.6–193.1 |
| 76 | H | Cl | F | H | $(CH_2)_2OH$ | 55.5–58.5 |
| 77 | H | F | F | H | $(CH_2)_2OH$ | 54.2–58.1 |
| 78 | H | H | F | F | $C_2H_5$ | 138.5–139.4 |
| 79 | Me | H | F | F | $(CH_2)_2OH$ | 171–173.8 |
| 80 | H | H | F | F | $(CH_2)_2OH$ | 156.5–157 | and are named as follows:
54. N-{4-[5-Benzoyl-1,4-dimethyl-1H-pyrrol-2-ylmethyl]phenyl}methanesulfonamide.
55. N-{4-[5-Benzoyl-1,4-dimethyl-1H-pyrrol-2-ylmethyl]phenyl}-2-(methoxycarbonyl)-ethanesulfonamide.
56. N-{4-[5-Benzoyl-1,4-dimethyl-1H-pyrrol-2-ylmethyl]phenyl}-2-(carboxy)ethane-sulfonamide.
57. N-{4-[5-benzoyl-1,4-dimethyl-1H-pyrrol-2-ylmethyl]phenyl}-2-(hydroxy)ethane-sulfonamide.
58. N-{4-[5-Benzoyl-1,4-dimethyl-1H-pyrrol-2-ylmethyl]phenyl}ethanesulfonamide.
59. N-{3-Chloro-4-[5-benzoyl-1,4-dimethyl-1H-pyrrol-2-ylmethyl]phenyl}methanesulfonamide.
60. N-{3-Fluoro-4-[5-benzoyl-1,4-dimethyl-1H-pyrrol-2-ylmethyl]phenyl}methanesulfonamide.
61. N-{3-Methoxy-4-[5-benzoyl-1,4-dimethyl-1H-pyrrol-2-ylmethyl]phenyl}methanesulfonamide.
62. N-{3-Trifluoromethyl-4-[5-benzoyl-1,4-dimethyl-1H-pyrrol-2-ylmethyl]phenyl}methanesulfonamide.
63. N-{3-Fluoro-4-[5-benzoyl-1,4-dimethyl-1H-pyrrol-2-ylmethyl]phenyl}-2-(hydroxy)-ethanesulfonamide.
64. N-{4-[5-Benzoyl-1-methyl-1H-pyrrol-2-ylmethyl]phenyl}methanesulfonamide.
65. N-{3-Fluoro-4-[5-benzoyl-1-methyl-1H-pyrrol-2-ylmethyl]phenyl}methanesulfonamide.
66. N-{3-Fluoro-4-[5-benzoyl-1-methyl-1H-pyrrol-2-ylmethyl]phenyl}-2-(hydroxy)-ethanesulfonamide, m/e=416 (M+).
67. N-Acetyl-N-{3-Fluoro-4-[5-benzoyl-1,4-dimethyl-1H-pyrrol-2-ylmethyl]phenyl}-methanesulfonamide.
68. N-{3-Fluoro-4-[5-benzoyl-1,4-dimethyl-1H-pyrrol-2-ylmethyl]phenyl}ethanesulfonamide.
69. N-{3-Chloro-4-[5-benzoyl-1-methyl-1H-pyrrol-2-ylmethyl]phenyl}-2-(hydroxy)-ethanesulfonamide.
70. N-{3-Chloro-4-[5-benzoyl-1-methyl-1H-pyrrol-2-ylmethyl]phenyl}methanesulfonamide.
71. N-{3-Fluoro-4-[5-(2-methylbenzoyl)-1-methyl-1H-pyrrol-2-ylmethyl]phenyl}-methanesulfonamide.
72. N-{3-Fluoro-4-[5-(2-methoxybenzoyl)-1-methyl-1H-pyrrol-2-ylmethyl]phenyl}-methanesulfonamide.
73. N-{3-Fluoro-4-[5-(2-methoxybenzoyl)-1-methyl-1H-pyrrol-2-ylmethyl]phenyl}-2-(hydroxy)-ethanesulfonamide, m/e=446 (M+).
74. N-{3-Fluoro-4-[5-(2-fluorobenzoyl)-1-methyl-1H-pyrrol-2-ylmethyl]phenyl}-methanesulfonamide.
75. N-{3,5-Difluoro-4-[5-benzoyl-1-methyl-1H-pyrrol-2-ylmethyl]phenyl}methanesulfonamide.
76. N-{3-Fluoro-4-[5-(2-chlorobenzoyl)-1-methyl-1H-pyrrol-2-ylmethyl]phenyl}-2-(hydroxy)-ethanesulfonamide.
77. N-{3-Fluoro-4-[5-(2-fluorobenzoyl)-1-methyl-1H-pyrrol-2-ylmethyl]phenyl}-2-(hydroxy)-ethanesulfonamide.
78. N-{3,5-Difluoro-4-[5-benzoyl-1-methyl-1H-pyrrol-2-ylmethyl]phenyl}ethanesulfonamide.
79. N-{3,5-Difluoro-4-[5-benzoyl-1,4-dimethyl-1H-pyrrol-2-ylmethyl]phenyl}-2-(hydroxy)-ethanesulfonamide.
80. N-{3,5-Difluoro-4-[5-benzoyl-1-methyl-1H-pyrrol-2-ylmethyl]phenyl}-2-(hydroxy)-ethanesulfonamide.

Id. Compounds of formula I where $R_1$=Me; $R_4=R_5=R_{13}=R_{15}=R_{16}=R_{23}=R_{25}=R_{26}=H$; $R_{10}$=is a group represented by formula (A); $R_{20}$=is a group represented by formula (U); and $R_{24}=R_{30}=NH^*SO_2R_{31}$, are:

| CPD# | $R_{12}$ | $R_{14}$ | $R_3$ | $R_{22}$ | $R_{31}$ | M.Pt. ° C. |
|---|---|---|---|---|---|---|
| 81 | H | $NMe_2$ | H | H | Me | 210–211 |
| 82 | H | Cl | H | H | Me | 164 |
| 83 | H | Br | H | H | Me | 169–170 |
| 84 | Me | Me | H | H | Me | 129–130 |
| 85 | H | OMe | H | H | Me | 147–148 |
| 86 | H | SMe | H | H | Me | 185–186 |
| 87 | H | $NH_2$ | H | H | Me | 203.3–205 |
| 88 | H | $NMe_2$ | H | F | Me | 199 |
| 89 | H | $NMe_2$ | H | CN | Me | 203 |
| 90 | H | $CH_2CH_3$ | H | H | Me | 115–116 |
| 91 | H | cyclopropyl | H | H | Me | foam |
| 92 | Me | H | Me | H | Me | 149–151 |
| 93 | H | Sme | Me | H | Me | 182.6–183.3 |
| 94 | H | SMe | Me | H | $CH_2CH_3$ $Na^+$ | >280 |
| 95 | H | OMe | Me | F | Me | 186.6–187.5 |
| 96 | H | OMe | H | F | Me | 180.9–181.8 |
| 97 | H | OMe | Me | F | $CH_2CH_3$ | 109–110 |
| 98 | H | OMe | Me | F | $(CH_2)_2OH$ | 139.5–140.5 |
| 99 | H | OMe | H | CN | Me | 164.7–166.7 |
| 100 | H | SMe | Me | F | $CH_2CH_3$ | 148.1–148.7 |
| 101 | H | F | Me | F | Me | 169.2–169.7 |
| 102 | H | F | Me | F | $CH_2CH_3$ | 138.2–139.2 |
| 103 | H | SMe | Me | F | Me | 188.8–189.5 |

-continued

| CPD# | $R_{12}$ | $R_{14}$ | $R_3$ | $R_{22}$ | $R_{31}$ | M.Pt. °C. |
|---|---|---|---|---|---|---|
| 104 | H | F | Me | F | $(CH_2)_2OH$ | 139.1–140.2 |
| 105 | H | OMe | Me | F | $CH=CH_2$ | 90–92 |
| 106 | H | OMe | H | F | $(CH_2)_2OH$ | 135–137 |
| 107 | H | SMe | Me | F | $(CH_2)_2OCOMe$ | 146.2–146.7 |
| 108 | H | SMe | Me | F | $(CH_2)_2OH$ | 174.9–175.5 |
| 109 | H | $CF_3$ | Me | F | Me | 177–177.8 |
| 110 | H | $CF_3$ | Me | F | $CH_2CH_3$ | 132.4–133.2 |
| 111 | H | cyclopropyl | H | F | Me | 140.5–142 |
| 112 | H | $CF_3$ | Me | Cl | Me | 203–204.8 |
| 113 | Cl | OMe | H | F | Me | 150–151 |
| 114 | Cl | OMe | H | F | $(CH_2)_2OH$ | |
| 115 | F | F | H | F | Me | 168.4–169.1 |
| 116 | F | F | H | F | $(CH_2)_2OH$ | 80–84 |
| 117 | H | $OC_2H_5$ | H | F | Me | 134.6–134.9 |
| 118 | OMe | F | H | F | Me | 162–162.3 |
| 119 | H | $OC_2H_5$ | H | F | $CH_2CH_3$ | 135.3–135.6 |
| 120 | OMe | F | H | F | $(CH_2)_2OH$ | 58.1–64.1 |
| 121 | H | $OC_2H_5$ | H | F | $(CH_2)_2OH$ | 105–106.5 |
| 122 | Me | OMe | H | F | Me | 149.5–150.1 |
| 123 | Me | OMe | H | F | $(CH_2)_2OH$ | 56.3–61.7 |
| 124 | Me | Br | H | F | Me | 177.5–178 |
| 125 | Me | Br | H | F | $(CH_2)_2OH$ | 70.5–71.5 |
| 126 | F | OMe | H | F | Me | 164.5–165.1 |
| 127 | H | Br | H | F | Me | 178.6–179.5 |
| 128 | H | Br | H | F | $(CH_2)_2OH$ | 53.5–56 |
| 129 | H | Cl | H | F | Me | 175.4–176.1 |
| 130 | H | Cl | H | F | $(CH_2)_2OH$ | 143.1–144 | and are named as follows:

81. N-{4-[5-(4-Dimethylaminobenzoyl)-1-methyl-1H-pyrrol-2-ylmethyl]phenyl}methanesulfonamide.
82. N-{4-[5-(4-Chlorobenzoyl)-1-methyl-1H-pyrrol-2-ylmethyl]phenyl}methanesulfonamide.
83. N-{4-[5-(4-Bromobenzoyl)-1-methyl-1H-pyrrol-2-ylmethyl]phenyl}methanesulfonamide.
84. N-{4-[5-(2,4-Dimethylbenzoyl)-1,4-dimethyl-1H-pyrrol-2-ylmethyl]phenyl}-methanesulfonamide.
85. N-{4-[5-(4-Methoxybenzoyl)-1-methyl-1H-pyrrol-2-ylmethyl]-phenyl}methanesulfonamide.
86. N-{4-[5-(4-Methylthiobenzoyl)-1-methyl-1H-pyrrol-2-ylmethyl]phenyl}methanesulfonamide.
87. N-{4-[5-(4-Aminobenzoyl)-1-methyl-1H-pyrrol-2-ylmethyl]phenyl}methanesulfonamide.
88. N-{3-Fluoro-4-[5-(4-dimethylaminobenzoyl)-1-methyl-1H-pyrrol-2-ylmethyl]phenyl}-methanesulfonamide.
89. N-{3-Cyano-4-[5-(4-dimethylaminobenzoyl)-1-methyl-1H-pyrrol-2-ylmethyl]phenyl}-methanesulfonamide.
90. N-{4-[5-(4-Ethylbenzoyl)-1-methyl-1H-pyrrol-2-ylmethyl]phenyl}methanesulfonamide.
91. N-{4-[5-(4-Cyclopropylbenzoyl)-1-methyl-1H-pyrrol-2-ylmethyl]phenyl}-methanesulfonamide.
92. N-{4-[5-(2-Methylbenzoyl)-1,4-dimethyl-1H-pyrrol-2-ylmethyl]phenyl}-methanesulfonamide.
93. N-{4-[5-(4-Methylthiobenzoyl)-1,4-dimethyl-1H-pyrrol-2-ylmethyl]phenyl}methanesulfonamide.
94. N-{4-[5-(4-Methylthiobenzoyl)-1,4-dimethyl-1H-pyrrol-2-ylmethyl]phenyl}ethanesulfonamide sodium salt.
95. N-{3-Fluoro-4-[5-(4-methoxybenzoyl)-1,4-dimethyl-1H-pyrrol-2-ylmethyl]phenyl}-methanesulfonamide.
96. N-{3-Fluoro-4-[5-(4-methoxybenzoyl)-1-methyl-1H-pyrrol-2-ylmethyl]phenyl}-methanesulfonamide.
97. N-{3-Fluoro-4-[5-(4-methoxybenzoyl)-1,4-dimethyl-1H-pyrrol-2-ylmethyl]phenyl}ethanesulfonamide.
98. N-{3-Fluoro-4-[5-(4-methoxybenzoyl)-1,4-dimethyl-1H-pyrrol-2-ylmethyl]phenyl}-2-(hydroxy)ethanesulfonamide.
99. N-{3-Cyano-4-[5-(4-methoxybenzoyl)-1-methyl-1H-pyrrol-2-ylmethyl]phenyl}-methanesulfonamide.
100. N-{3-Fluoro-4-[5-(4-methylthiobenzoyl)-1,4-dimethyl-1H-pyrrol-2-ylmethyl]phenyl}ethanesulfonamide.
101. N-{3-Fluoro-4-[5-(4-fluorobenzoyl)-1,4-dimethyl-1H-pyrrol-2-ylmethyl]phenyl}-methanesulfonamide.
102. N-{3-Fluoro-4-[5-(4-fluorobenzoyl)-1,4-dimethyl-1H-pyrrol-2-ylmethyl]phenyl}ethanesulfonamide.
103. N-{3-Fluoro-4-[5-(4-methylthiobenzoyl)-1,4-dimethyl-1H-pyrrol-2-ylmethyl]phenyl}-methanesulfonamide.
104. N-{3-Fluoro-4-[5-(4-fluorobenzoyl)-1,4-dimethyl-1H-pyrrol-2-ylmethyl]phenyl}-2-(hydroxy)ethanesulfonamide.
105. N-{3-Fluoro-4-[5-(4-methoxybenzoyl)-1,4-dimethyl-1H-pyrrol-2-ylmethyl]phenyl}ethenesulfonamide.
106. N-{3-Fluoro-4-[5-(4-methoxybenzoyl)-1-methyl-1H-pyrrol-2-ylmethyl]phenyl}-2-(hydroxy)ethanesulfonamide.
107. N-{3-Fluoro-4-[5-(4-methylthiobenzoyl)-1,4-dimethyl-1H-pyrrol-2-ylmethyl]phenyl}-2-(acetoxy)ethanesulfonamide.
108. N-{3-Fluoro-4-[5-(4-methylthiobenzoyl)-1,4-dimethyl-1H-pyrrol-2-ylmethyl]phenyl}-2-(hydroxy)ethanesulfonamide.
109. N-{3-Fluoro-4-[5-(4-trifluoromethylbenzoyl)-1,4-dimethyl-1H-pyrrol-2-ylmethyl]phenyl}-methanesulfonamide.
110. N-{3-Fluoro-4-[5-(4-trifluoromethylbenzoyl)-1,4-dimethyl-1H-pyrrol-2-ylmethyl]phenyl}ethanesulfonamide.
111. N-{3-Fluoro-4-[5-(4-cyclopropylbenzoyl)-1-methyl-1H-pyrrol-2-ylmethyl]phenyl}-methanesulfonamide.
112. N-{3-Chloro-4-[5-(4-trifluoromethylbenzoyl)-1,4-dimethyl-1H-pyrrol-2-ylmethyl]phenyl}-methanesulfonamide.
113. N-{3-Fluoro-4-[5-(2-chloro-4-methoxylbenzoyl)-1-methyl-1H-pyrrol-2-ylmethyl]phenyl}-methanesulfonamide.
114. N-{3-Fluoro-4-[5-(2-chloro-4-methoxylbenzoyl)-1-methyl-1H-pyrrol-2-ylmethyl]phenyl}-2-(hydroxy)ethanesulfonamide, m/e=481 (M+H).
115. N-{3-Fluoro-4-[5-(2,4-difluorobenzoyl)-1-methyl-1H-pyrrol-2-ylmethyl]phenyl}-methanesulfonamide.
116. N-{3-Fluoro-4-[5-(2,4-difluorobenzoyl)-1-methyl-1H-pyrrol-2-ylmethyl]phenyl}-2-(hydroxy)-ethanesulfonamide.
117. N-{3-Fluoro-4-[5-(4-ethoxybenzoyl)-1-methyl-1H-pyrrol-2-ylmethyl]phenyl}-methanesulfonamide.
118. N-{3-Fluoro-4-[5-(4-fluoro-2-methoxybenzoyl)-1-methyl-1H-pyrrol-2-ylmethyl]phenyl}-methanesulfonamide.
119. N-{3-Fluoro-4-[5-(4-ethoxybenzoyl)-1-methyl-1H-pyrrol-2-ylmethyl]phenyl}ethanesulfonamide.
120. N-{3-Fluoro-4-[5-(4-fluoro-2-methoxybenzoyl)-1-methyl-I H-pyrrol-2-ylmethyl]phenyl}-2-(hydroxy)ethanesulfonamide.
121. N-{3-Fluoro-4-[5-(4-ethoxybenzoyl)-1-methyl-1H-pyrrol-2-ylmethyl]phenyl}-2-(hydroxy)ethanesulfonamide.
122. N-{3-Fluoro-4-[5-(4-methoxy-2-methylbenzoyl)-1-methyl-1H-pyrrol-2-ylmethyl]phenyl}-methanesulfonamide.
123. N-{3-Fluoro-4-[5-(4-methoxy-2-methylbenzoyl)-1-methyl-1H-pyrrol-2-ylmethyl]phenyl}-2-(hydroxy)ethanesulfonamide.

124. N-{3-Fluoro-4-[5-(4-bromo-2-methylbenzoyl)-1-methyl-1H-pyrrol-2-ylmethyl]phenyl}-methanesulfonamide.
125. N-{3-Fluoro-4-[5-(4-bromo-2-methylbenzoyl)-1-methyl-1H-pyrrol-2-ylmethyl]phenyl}-2-(hydroxy)ethanesulfonamide.
126. N-{3-Fluoro-4-[5-(2-fluoro-4-methoxybenzoyl)-1-methyl-1H-pyrrol-2-ylmethyl]phenyl}-methanesulfonamide.
127. N-{3-Fluoro-4-[5-(4-bromobenzoyl)-1-methyl-1H-pyrrol-2-ylmethyl]phenyl}-methanesulfonamide.
128. N-{3-Fluoro-4-[5-(4-bromobenzoyl)-1-methyl-1H-pyrrol-2-ylmethyl]phenyl}-2-(hydroxy)ethanesulfonamide.
129. N-{3-Fluoro-4-[5-(4-chlorobenzoyl)-1-methyl-1H-pyrrol-2-ylmethyl]phenyl}-methanesulfonamide.
130. N-{3-Fluoro-4-[5-(4-chlorobenzoyl)-1-methyl-1H-pyrrol-2-ylmethyl]phenyl}-2-(hydroxy)ethanesulfonamide.

Ie. Compounds of formula I where $R_1+R_5=$—$(CH_2)_2$—; $R_3=R_4=R_{12}=R_{13}=R_{15}=R_{16}=R_{23}=R_{25}=R_{26}=H$; $R_{10}=$is a group represented by formula (A); $R_{20}=$is a group represented by formula (U); and $R_{24}=R_{30}=NH*SO_2R_{31}$, are:

| CPD# | $R_{14}$ | $R_{22}$ | $R_{31}$ | M.Pt. °C. |
|---|---|---|---|---|
| 131 | H | Cl | Me | 85–95 |
| 132 | OMe | Cl | Me | 183–183.5 |
| 133 | OMe | Cl | $(CH_2)_2OH$ | 74.5–84.5 |
| 134 | H | Cl | $(CH_2)_2OH$ | 80.5–109 |
| 135 | H | F | Me | 162–162.8 |
| 136 | OMe | H | Me | 146–147.1 |
| 137 | OMe | F | $(CH_2)_2OH$ | 146–147.1 |
| 138 | OMe | F | Me | 159–162 |
| 139 | H | F | $(CH_2)_2OH$ | 159–161.5 | and are named as follows:
131. N-{3-Chloro-4-[5-Benzoyl-1,2-dihydro-3H-pyrrolizin-1-yl]phenyl}methanesulfonamide.
132. N-{3-Chloro-4-[5-(4-methoxybenzoyl)-1,2-dihydro-3H-pyrrolizin-1-yl]phenyl}-methanesulfonamide.
133. N-{3-Chloro-4-[5-(4-methoxybenzoyl)-1,2-dihydro-3H-pyrrolizin-1-yl]phenyl}-2-(hydroxy)ethanesulfonamide.
134. N-{3-Chloro-4-[5-benzoyl-1,2-dihydro-3H-pyrrolizin-1-yl]phenyl}-2-(hydroxy)-ethanesulfonamide.
135. N-{3-Fluoro-4-[5-benzoyl-1,2-dihydro-3H-pyrrolizin-1-yl]phenyl}methanesulfonamide.
136. N-{4-[5-(4-methoxybenzoyl)-1,2-dihydro-3H-pyrrolizin-1-yl]phenyl}methanesulfonamide.
137. N-{3-Fluoro-4-[5-(4-methoxybenzoyl)-1,2-dihydro-3H-pyrrolizin-1-yl]phenyl}-2-(hydroxy)-ethanesulfonamide.
138. N-{3-Fluoro-4-[5-(4-methoxybenzoyl)-1,2-dihydro-3H-pyrrolizin-1-yl]phenyl}-methanesulfonamide.
139. N-{3-Fluoro-4-[5-benzoyl-1,2-dihydro-3H-pyrrolizin-1-yl]phenyl}-2-(hydroxy)-ethanesulfonamide.

IIa. Compounds of formula I where $R_1=R_3=Me$; $R_4=R_5=R_{12}=R_{13}=R_{15}=R_{16}=R_{23}=R_{25}=R_{26}=H$; $R_{14}=Cl$; $R_{10}=$is a group represented by formula (A); $R_{20}=$is a group represented by formula (U); and $R_{24}=R_{30}=NH*SO_2NR_{32}R_{34}$, are:

| CPD# | $R_{22}$ | $R_{32}$ | $R_{34}$ | M.Pt. °C. |
|---|---|---|---|---|
| 140 | H | Me | Me | 57–142 |
| 141 | H | H | H | 175–177 |
| 132 | H | H | $COCH_3$ | 164.5–170 |
| 143 | H | $(CH_2)_2OH$ | $(CH_2)_2OH$ | 122–124 |
| 144 | Cl | Me | Me | 175–177 |
| 145 | F | Me | Me | 185–186 |
| 146 | F | H | H | 179.8–180 |
| 147 | CN | H | H | 192 |
| 148 | Cl | H | H | 179–180 | and are named as follows:
140. 1-{4-[5-(4-Chlorobenzoyl)-1,4-dimethyl-1H-pyrrol-2-ylmethyl]phenyl}-3,3-dimethylsufamide.
141. 1-{4-[5-(4-Chlorobenzoyl)-1,4-dimethyl-1H-pyrrol-2-ylmethyl]phenyl}sulfamide.
142. 1-{4-[5-(4-Chlorobenzoyl)-1,4-dimethyl-1H-pyrrol-2-ylmethyl]phenyl}-3-acetylsulfamide.
143. 1-{4-[5-(4-Chlorobenzoyl)-1,4-dimethyl-1H-pyrrol-2-ylmethyl]-phenyl}-3,3-bis-(2-hydroxyethyl)sulfamide.
144. 1-{3-Chloro-4-[5-(4-chlorobenzoyl)-1,4-dimethyl-1H-pyrrol-2-ylmethyl]phenyl}-3,3-dimethylsulfamide.
145. 1-{3-Fluoro-4-[5-(4-chlorobenzoyl)-1,4-dimethyl-1H-pyrrol-2-ylmethyl]phenyl}-3,3-dimethylsulfamide.
146. 1-{3-Fluoro-4-[5-(4-chlorobenzoyl)-1,4-dimethyl-1H-pyrrol-2-ylmethyl]phenyl}sulfamide.
147. 1-{3-Cyano-4-[5-(4-chlorobenzoyl)-1,4-dimethyl-1H-pyrrol-2-ylmethyl]phenyl}sulfamide.
148. 1-{3-Chloro-4-[5-(4-chlorobenzoyl)-1,4-dimethyl-1H-pyrrol-2-ylmethyl]phenyl}sulfamide.

IIb. Compounds of formula I where $R_1=Me$; $R_4=R_5=R_{13}=R_{15}=R_{16}=R_{23}=R_{25}=H$; $R_{14}=Me$; $R_{10}=$is a group represented by formula (A); $R_{20}=$is a group represented by formula (U); and $R_{24}=R_{30}=NH*SO_2NR_{32}R_{34}$, are:

| CPD# | $R_3$ | $R_{12}$ | $R_{22}$ | $R_{26}$ | $R_{32}$ | $R_{34}$ | M. Pt. °C. |
|---|---|---|---|---|---|---|---|
| 149 | H | H | H | H | Me | Me | 130–139 |
| 150 | H | H | H | H | H | H | 152–152.8 |
| 151 | H | H | Cl | H | Me | Me | 157–159 |
| 152 | H | H | $CF_3$ | H | Me | Me | 114–115 |
| 153 | H | H | Br | H | Me | Me | 157–158 |
| 154 | H | H | F | H | H | H | 153.1–153.9 |
| 155 | H | H | F | H | Me | Me | 158–158.9 |
| 156 | H | H | Cl | H | H | H | 166.3–166.9 |
| 157 | H | H | F | H | $(CH_2)_2OH$ | $(CH_2)_2OH$ | 108.4–108.7 |
| 158 | H | H | F | H | H | Me | foam |
| 159 | H | H | F | H | H | $CH_2CH_3$ | foam |
| 160 | H | H | F | H | H | $(CH_2)_2OMe$ | foam |
| 161 | Me | H | F | H | H | Me | 166.5–167. |
| 162 | Me | H | F | H | H | H | 189.5–189.9 |
| 163 | Me | H | F | H | Me | Me | 169.6–170.5 |
| 164 | H | H | F | H | H | $(CH_2)_2OH$ | 120.2–121.8 |
| 165 | H | Me | F | H | H | H | 149–152 |
| 166 | Me | Me | Cl | H | Me | Me | 58.9–61.8 |
| 167 | Me | Me | Cl | H | H | H | 76.5–80.2 |
| 168 | H | Me | H | H | H | $CH_2CH_3$ | 66–70 |
| 169 | H | Me | H | H | H | H | 77–88.6 |
| 170 | H | Me | H | H | H | Me | 76–80 |
| 171 | Me | Me | CN | H | H | H | 161.5–165 |
| 172 | H | Me | F | H | H | Me | 65.1–67.5 |
| 173 | Me | Me | CN | H | Me | Me | 67–71 |
| 174 | H | H | F | F | H | H | 202.2–202.8 |
| 175 | H | Me | F | H | H | $COCH_3$ | 94–97.5 | and are named as follows:
149. 1-{4-[5-(4-Methylbenzoyl)-1-methyl-1H-pyrrol-2-ylmethyl]phenyl}-3,3-dimethylsulfamide.

150. 1-{4-[5-(4-Methylbenzoyl)-1-methyl-1H-pyrrol-2-ylmethyl]phenyl}sulfamide.
151. 1-{3-Chloro-4-[5-(4-methylbenzoyl)-1-methyl-1H-pyrrol-2-ylmethyl]phenyl}-3,3-dimethylsulfamide.
152. 1-{3-Trifluoromethyl-4-[5-(4-methylbenzoyl)-1-methyl-1H-pyrrol-2-ylmethyl]phenyl}-3,3-dimethylsulfamide.
153. 1-{3-Bromo-4-[5-(4-methylbenzoyl)-1-methyl-1H-pyrrol-2-ylmethyl]phenyl}-3,3-dimethylsulfamide.
154. 1-{3-Fluoro-4-[5-(4-methylbenzoyl)-1-methyl-1H-pyrrol-2-ylmethyl]phenyl}sulfamide.
155. 1-{3-Fluoro-4-[5-(4-methylbenzoyl)-1-methyl-1H-pyrrol-2-ylmethyl]phenyl}-3,3-dimethylsulfamide.
156. 1-{3-Chloro-4-[5-(4-methylbenzoyl)-1-methyl-1H-pyrrol-2-ylmethyl]phenyl}sulfamide.
157. 1-{3-Fluoro-4-[5-(4-methylbenzoyl)-1-methyl-1H-pyrrol-2-ylmethyl]phenyl}-3,3-bis-(2-hydroxyethyl)sulfamide.
158. 1-{3-Fluoro-4-[5-(4-methylbenzoyl)-1-methyl-1H-pyrrol-2-ylmethyl]phenyl}-3-methylsulfamide, m/e=415 (M+).
159. 1-{3-Fluoro-4-[5-(4-methylbenzoyl)-1-methyl-1H-pyrrol-2-ylmethyl]phenyl}-3-ethylsulfamide, m/e=429 (M+).
160. 1-{3-Fluoro-4-[5-(4-methylbenzoyl)-1-methyl-1H-pyrrol-2-ylmethyl]phenyl}-3-(2-methoxyethyl)sulfamide, m/e=459 (M+).
161. 1-{3-Fluoro-4-[5-(4-methylbenzoyl)-1,4-dimethyl-1H-pyrrol-2-ylmethyl]phenyl}-3-methylsulfamide.
162. 1-{3-Fluoro-4-[5-(4-methylbenzoyl)-1,4-dimethyl-1H-pyrrol-2-ylmethyl]phenyl}sulfamide.
163. 1-{3-Fluoro-4-[5-(4-methylbenzoyl)-1,4-dimethyl-1H-pyrrol-2-ylmethyl]phenyl}-3,3-dimethylsulfamide.
164. 1-{3-Fluoro-4-[5-(4-methylbenzoyl)-1-methyl-1H-pyrrol-2-ylmethyl]phenyl}-3-(2-hydroxyethyl)sulfamide.
165. 1-{3-Fluoro-4-[5-(2,4-dimethylbenzoyl)-1-methyl-1H-pyrrol-2-ylmethyl]phenyl}sulfamide.
166. 1-{3-Chloro-4-[5-(2,4-dimethylbenzoyl)-1,4-dimethyl-1H-pyrrol-2-ylmethyl]phenyl}-3,3-dimethylsulfamide.
167. 1-{3-Chloro-[5-(2,4-dimethylbenzoyl)-1,4-dimethyl-1H-pyrrol-2-ylmethyl]phenyl}sulfamide.
168. 1-{4-[5-(2,4-Dimethylbenzoyl)-1-methyl-1H-pyrrol-2-ylmethyl]phenyl}-3-ethylsulfamide.
169. 1-{4-[5-(2,4-Dimethylbenzoyl)-1-methyl-1H-pyrrol-2-ylmethyl]phenyl}sulfamide.
170. 1-{4-[5-(2,4-Dimethylbenzoyl)-1-methyl-1H-pyrrol-2-ylmethyl]phenyl}-3-methylsufamide.
171. 1-{3-Cyano-4-[5-(2,4-dimethylbenzoyl)-1,4-dimethyl-1H-pyrrol-2-ylmethyl]phenyl}sulfanide.
172. 1-{3-Fluoro-4-[5-(2,4-dimethylbenzoyl)-1-methyl-1H-pyrrol-2-ylmethyl]phenyl}-3-methylsulfamide.
173. 1-{3-Cyano-4-[5-(2,4-dimethylbenzoyl)-1,4-dimethyl-1H-pyrrol-2-ylmethyl]phenyl}-3,3-dimethylsulfamide.
174. 1-{3,5-Difluoro-4-[5-(4-methylbenzoyl)-1-methyl-1H-pyrrol-2-ylmethyl]phenyl}sulfamide.
175. 1-{3-Fluoro-4-[5-(2,4-dimethylbenzoyl)-1-methyl-1H-pyrrol-2-ylmethyl]phenyl}-3-acetylsulfamide.

IIc. Compounds of formula I where $R_1$=Me; $R_4$=$R_5$=$R_{13}$=$R_{15}$=$R_{16}$=$R_{23}$=$R_{25}$=H, $R_{14}$=H; $R_{10}$=is a group represented by formula (A); $R_{20}$=is a group represented by formula (U); and $R_{24}$=$R_{30}$=NH*$SO_2$NR$_{32}$R$_{34}$, are:

| CPD# | $R_3$ | $R_{12}$ | $R_{22}$ | $R_{26}$ | $R_{32}$ | $R_{34}$ | M.Pt. °C. |
|---|---|---|---|---|---|---|---|
| 176 | Me | H | H | H | Me | Me | 126.5–127.4 |
| 177 | Me | H | H | H | H | H | 179.1–180 |
| 178 | Me | H | Cl | H | Me | Me | 185–187 |
| 179 | Me | H | F | H | Me | Me | 182–183 |
| 180 | Me | H | OMe | H | Me | Me | 166–167 |
| 181 | Me | H | $CF_3$ | H | Me | Me | 164–165 |
| 182 | H | H | F | H | H | H | 168.6–169.2 |
| 183 | H | H | CN | H | H | H | 176.4–176.8 |
| 184 | H | H | Cl | H | H | H | 167.4–168.3 |
| 185 | H | Cl | F | H | Me | H | 99–150.5 |
| 186 | H | Cl | F | H | Me | Me | 68.4–69.8 |
| 187 | H | Cl | F | H | H | H | 171.8–172.6 |
| 188 | H | F | F | H | Me | Me | 114.4–114.9 |
| 189 | H | H | F | F | H | H | 199.8–200.2 |
| 190 | H | H | F | F | H | Me | 179–180.5 |
| 191 | H | OMe | F | H | H | H | 144.7–146 |
| 192 | H | Me | F | H | H | H | 186.3–186.6 |
| 193 | Me | H | F | F | H | H | 222.5–223 |
| 194 | H | H | F | F | Me | Me | 158–159.3 | and are named as follows:
176. 1-{4-[5-Benzoyl-1,4-dimethyl-1H-pyrrol-2-ylmethyl]phenyl}-3,3-dimethylsulfamide.
177. 1-{4-[5-benzoyl-1,4-dimethyl-1H-pyrrol-2-ylmethyl]phenyl}sulfamide.
178. 1-{3-Chloro-4-[5-benzoyl-1,4-dimethyl-1H-pyrrol-2-ylmethyl]phenyl}-3,3-dimethylsulfamide.
179. 1-{3-Fluoro-4-[5-benzoyl-1,4-dimethyl-1H-pyrrol-2-ylmethyl]phenyl}-3,3-dimethylsulfamide.
180. 1-{3-Methoxy-4-[5-benzoyl-1,4-dimethyl-1H-pyrrol-2-ylmethyl]phenyl}-3,3-dimethylsulfamide.
181. 1-{3-Trifluoromethyl-4-[5-benzoyl-1,4-dimethyl-1H-pyrrol-2-ylmethyl]phenyl}-3,3-dimethylsulfamide.
182. 1-{3-Fluoro-4-[5-benzoyl-1-methyl-1H-pyrrol-2-ylmethyl]phenyl}sulfamide.
183. 1-{3-Cyano-4-[5-benzoyl-1-methyl-1H-pyrrol-2-ylmethyl]phenyl}sulfamide.
184. 1-{3-Chloro-4-[5-benzoyl-1-methyl-1H-pyrrol-2-ylmethyl]phenyl}sulfamide.
185. 1-{3-Fluoro-4-[5-(2-chlorobenzoyl)-1-methyl-1H-pyrrol-2-ylmethyl]phenyl}-3-methylsulfamide.
186. 1-{3-Fluoro-4-[5-(2-chlorobenzoyl)-1-methyl-1H-pyrrol-2-ylmethyl]phenyl}-3,3-dimethylsulfamide.
187. 1-{3-Fluoro-4-[5-(2-chlorobenzoyl)-1-methyl-1H-pyrrol-2-ylmethyl]phenyl}sulfamide.
188. 1-{3-Fluoro-4-[5-(2-fluorobenzoyl)-1-methyl-1H-pyrrol-2-ylmethyl]phenyl}-3-3-dimethylsulfamide.
189. 1-{3-Difluoro-4-[5-benzoyl-1-methyl-1H-pyrrol-2-ylmethyl]phenyl}sulfamide.
190. 1-{3-Difluoro-4-[5-benzoyl-1-methyl-1H-pyrrol-2-ylmethyl]phenyl}-3-methylsulfamide.
191. 1-{3-Fluoro-4-[5-(2-methoxybenzoyl)-1-methyl-1H-pyrrol-2-ylmethyl]phenyl}sulfamide.
192. 1-{3-Fluoro-4-[5-(2-methylbenzoyl)-1-methyl-1H-pyrrol-2-ylmethyl]phenyl}sulfamide.
193. 1-{3-Difluoro-4-[5-benzoyl-1,4-dimethyl-1H-pyrrol-2-ylmethyl]phenyl}sulfamide.
194. 1-{3-Difluoro-4-[5-benzoyl-1-methyl-1H-pyrrol-2-ylmethyl]phenyl}-3,3-dimethylsulfamide.

IId. Compounds of formula I where $R_1$=Me; $R_4$=$R_5$=$R_{13}$=$R_{15}$=$R_{16}$=$R_{23}$=$R_{25}$=$R_{26}$=H; $R_{10}$=is a group represented by formula (A); $R_{20}$=is a group represented by formula (U); and $R_{24}$=$R_{30}$=NH*$SO_2$NR$_{32}$R$_{34}$, are:

| CPD# | $R_{12}$ | $R_{14}$ | $R_3$ | $R_{22}$ | $R_{32}$ | $R_{34}$ | M.Pt. °C. |
|---|---|---|---|---|---|---|---|
| 195 | H | OMe | H | H | Me | Me | 147–148 |
| 196 | H | OMe | H | F | H | H | 133 |
| 197 | H | OMe | Me | F | H | H | 175–176.5 |
| 198 | H | OMe | Me | F | Me | Me | 165.3–166.2 |
| 199 | H | SMe | H | H | Me | Me | 117–118 |
| 200 | H | SMe | Me | H | Me | Me | 161.4–163.2 |
| 201 | H | NMe₂ | H | F | H | H | 193 |
| 202 | H | OMe | H | CN | H | H | 193 |
| 203 | H | NMe₂ | H | CN | H | H | 185 |
| 204 | H | F | Me | F | H | H | 184.8–185.2 |
| 205 | H | F | Me | F | Me | Me | 151–151.4 |
| 206 | H | F | Me | F | H | Me | 128–129 |
| 207 | H | SMe | Me | F | Me | Me | 177.8–178.3 |
| 208 | H | CF₃ | Me | F | Me | Me | 188–189 |
| 209 | H | cyclo-propyl | H | F | Me | Me | 128.6–129.2 |
| 210 | H | CF₃ | Me | F | H | Me | 179–179.9 |
| 211 | H | CF₃ | Me | Cl | H | H | 200–201 |
| 212 | F | F | H | F | H | Me | 90–92 |
| 213 | H | OC₂H₅ | H | F | Me | Me | 158.2–158.7 |
| 214 | OMe | F | H | F | Me | Me | 159–160 |
| 215 | OMe | F | H | F | H | Me | 152.2–157.5 |
| 216 | H | OC₂H₅ | H | F | H | H | 152.4–153.2 |
| 217 | Me | OMe | H | F | H | H | 157.7–158.3 |
| 218 | Me | Br | H | F | H | H | 162.3–162.9 |
| 219 | OMe | F | H | F | H | H | 101.4–108.5 |
| 220 | F | OMe | H | F | H | H | 168.9–171.5 |
| 221 | H | Cl | H | F | H | H | 190–190.3 | and are named as follows:
195. 1-{4-[5-(4-Methoxybenzoyl)-1-methyl-1H-pyrrol-2-ylmethyl]phenyl}-3,3-dimethylsulfamide.
196. 1-{3-Fluoro-4-[5-(4-Methoxybenzoyl)-1-methyl-1H-pyrrol-2-ylmethyl]phenyl}sulfamide.
197. 1-{3-Fluoro-4-[5-(4-Methoxybenzoyl)-1,4-dimethyl-1H-pyrrol-2-ylmethyl]phenyl}sulfamide.
198. 1-{3-Fluoro-4-[5-(4-Methoxybenzoyl)-1,4-dimethyl-1H-pyrrol-2-ylmethyl]phenyl}-3,3-dimethylsulfamide.
199. 1-{4-[5-(4-Methylthiobenzoyl)-1-methyl-1H-pyrrol-2-ylmethyl]phenyl}-3,3-dimethylsulfamide.
200. 1-{4-[5-(4-Methylthiobenzoyl)-1,4-dimethyl-1H-pyrrol-2-ylmethyl]phenyl}-3,3-dimethylsulfamide.
201. 1-{3-Fluoro-4-[5-(4-dimethylaminobenzoyl)-1-methyl-1H-pyrrol-2-ylmethyl]phenyl}sulfamide.
202. 1-{3-Cyano-4-[5-(4-methoxybenzoyl)-1-methyl-1H-pyrrol-2-ylmethyl]phenyl}-sufamide.
203. 1-{3-Cyano-4-[5-(4-dimethylaminobenzoyl)-1-methyl-1H-pyrrol-2-ylmethyl]phenyl}sulfamide.
204. 1-{3-Fluoro-4-[5-(4-fluorobenzoyl)-1,4-dimethyl-1H-pyrrol-2-ylmethyl]phenyl}-sufamide.
205. 1-{3-Fluoro-4-[5-(4-fluorobenzoyl)-1,4-dimethyl-1H-pyrrol-2-ylmethyl]phenyl}-3,3-dimethylsulfamide.
206. 1-{3-Fluoro-4-[5-(4-fluorobenzoyl)-1,4-dimethyl-1H-pyrrol-2-ylmethyl]phenyl}-3-methylsulfamide.
207. 1-{3-Fluoro-4-[5-(4-methylthiobenzoyl)-1,4-dimethyl-1H-pyrrol-2-ylmethyl]phenyl}-3,3-dimethylsulfamide.
208. 1-{3-Fluoro-4-[5-(4-trifluoromethylbenzoyl)-1,4-dimethyl-1H-pyrrol-2-ylmethyl]phenyl}-3,3-dimethylsulfamide.
209. 1-{3-Fluoro-4-[5-(4-cyclopropylbenzoyl)-1-methyl-1H-pyrrol-2-ylmethyl]phenyl}-3,3-dimethylsulfamide.
210. 1-{3-Fluoro-4-[5-(4-trifluoromethylbenzoyl)-1,4-dimethyl-1H-pyrrol-2-ylmethyl]phenyl}-3-methylsulfamide.
211. 1-{3-Chloro-4-[5-(4-trifluoromethylbenzoyl)-1,4-dimethyl-1H-pyrrol-2-ylmethyl]phenyl}sulfamide.
212. 1-{3-Fluoro-4-[5-(2,4-difluorobenzoyl)-1-methyl-1H-pyrrol-2-ylmethyl]phenyl}-3-methylsulfamide.
213. 1-{3-Fluoro-4-[5-(4-ethoxybenzoyl)-1-methyl-1H-pyrrol-2-ylmethyl]phenyl}-3,3-dimethylsulfamide.
214. 1-{3-Fluoro-4-[5-(4-fluoro-2-methoxybenzoyl)-1-methyl-1H-pyrrol-2-ylmethyl]phenyl}-3,3-dimethylsulfamide.
215. 1-{3-Fluoro-4-[5-(4-fluoro-2-methoxybenzoyl)-1-methyl-1H-pyrrol-2-ylmethyl]phenyl}-3-methylsulfamide.
216. 1-{3-Fluoro-4-[5-(4-ethoxybenzoyl)-1-methyl-1H-pyrrol-2-ylmethyl]phenyl}sufamide.
217. 1-{3-Fluoro-4-[5-(4-methoxy-2-methylbenzoyl)-1-methyl-1H-pyrrol-2-ylmethyl]phenyl}sulfamide.
218. 1-{3-Fluoro-4-[5-(4-bromo-2-methylbenzoyl)-1-methyl-1H-pyrrol-2-ylmethyl]phenyl}sulfamide.
219. 1-{3-Fluoro-4-[5-(4-fluoro-2-methoxybenzoyl)-1-methyl-1H-pyrrol-2-ylmethyl]phenyl}sulfamide.
220. 1-{3-Fluoro-4-[5-(2-fluoro-4-methoxybenzoyl)-1-methyl-1H-pyrrol-2-ylmethyl]phenyl}sulfamide.
221. 1-{3-Fluoro-4-[5-(4-chlorobenzoyl)-1-methyl-1H-pyrrol-2-ylmethyl]phenyl}sulfamide.

IIe. Compounds of formula (I) where $R_1+R_5=-(CH_2)_2-$; $R_3=R_4=R_{12}=R_{13}=R_{15}=R_{16}=R_{23}=R_{25}=R_{26}=H$; $R_{10}=$is a group represented by formula (A); $R_{20}=$is a group represented by formula (U); and $R_{24}=R_{30}=NHSO_2NR_{32}R_{34}$, are:

| CPD# | $R_{14}$ | $R_{22}$ | $R_{32}$ | $R_{34}$ | M.Pt. °C. |
|---|---|---|---|---|---|
| 222 | H | Cl | H | H | 115–126 |
| 223 | OMe | Cl | H | H | 112–130 |
| 224 | H | F | H | H | |
| 225 | OMe | F | H | H | 117.5–172.9 | and are named as follows:
222. 1-{3-Chloro-4-[5-benzoyl-1,2-dihydro-3H-pyrrolizin-1-yl]phenyl}sulfamide.
223. 1-{3-Chloro-4-[5-(4-methoxybenzoyl)-1,2-dihydro-3H-pyrrolizin-1-yl]phenyl}sulfamide.
224. 1-{3-Fluoro-4-[5-benzoyl-1,2-dihydro-3H-pyrrolizin-1-yl]phenyl}sulfamide.
225. 1-{3-Fluoro-4-[5-(4-methoxybenzoyl)-1,2-dihydro-3H-pyrrolizin-1-yl]phenyl}sulfamide.

IIIa. Compounds of formula I where $R_1=R_3=Me$; $R_4=R_5=R_{12}=R_{13}=R_{15}=R_{16}=R_{22}=R_{23}=R_{25}=R_{26}=H$; $R_{14}=Cl$; $R_{10}=$is a group represented by formula (A); $R_{20}=$is a group represented by formula (U); and $R_{24}=R_{30}=NH^*C(O)NR_{32}R_{33}$, are:

| CPD# | $R_{32}$ | $R_{33}$ | M.Pt. °C. |
|---|---|---|---|
| 226 | Me | Me | 199–201.9 |
| 227 | H | phenyl | 213.5–214.5 |
| 228 | H | 3-Cl-phenyl | 219.5–221.5 |
| 229 | H | CH₂CO₂H | 193.3–194 |
| 230 | H | (CH₂)₂OH | 209.6–210.2 |
| 231 | H | H | 214.6–215 | and are named as follows:
226. 1-{4-[5-(4-Chlorobenzoyl)-1,4-dimethyl-1H-pyrrol-2-ylmethyl]phenyl}-3,3-dimethylurea.
227. 1-{4-[5-(4-Chlorobenzoyl)-1,4-dimethyl-1H-pyrrol-2-ylmethyl]phenyl}-3-phenylurea.
228. 1-{4-[5-(4-Chlorobenzoyl)-1,4-dimethyl-1H-pyrrol-2-ylmethyl]phenyl}-3-(3-chlorophenyl)-urea.
229. 1-{4-[5-(4-Chlorobenzoyl)-1,4-dimethyl-1H-pyrrol-2-ylmethyl]phenyl}-3-carboxymethylurea.
230. 1-{4-[5-(4-Chlorobenzoyl)-1,4-dimethyl-1H-pyrrol-2-ylmethyl]phenyl}-3-(2-hydroxyethyl)-urea.
231. 1-{4-[5-(4-Chlorobenzoyl)-1,4-dimethyl-1H-pyrrol-2-ylmethyl]phenyl}urea.

IIIb. Compounds of formula I where $R_1$=Me; $R_3$=$R_4$=$R_5$=$R_{12}$=$R_{13}$=$R_{15}$=$R_{16}$=$R_{23}$=$R_{25}$=$R_{26}$=H; $R_{14}$=Me; $R_{10}$=is a group represented by formula (A); $R_{20}$=is a group represented by formula (U); and $R_{24}$=$R_{30}$=NH*C(O)N$R_{32}R_{33}$, are:

| CPD# | $R_{22}$ | $R_{32}$ | $R_{33}$ | M.Pt. ° C. |
|---|---|---|---|---|
| 232 | H | Me | Me | 167.2–167.7 |
| 233 | H | H | H | 188.4–189.9 |
| 234 | F | H | (CH$_2$)$_2$OH | 193.7–194.7 | and are named as follows:

232. 1-{4-[5-(4-Methylbenzoyl)-1-methyl-1H-pyrrol-2-ylmethyl]phenyl}-3,3-dimethylurea.
233. 1-{4-[5-(4-Methylbenzoyl)-1-methyl-1H-pyrrol-2-ylmethyl]phenyl}urea.
234. 1-{3-Fluoro-4-[5-(4-methylbenzoyl)-1-methyl-1H-pyrrol-2-ylmethyl]phenyl}-3-(2-hydroxyethyl)urea.

IV. Compounds of formula I where $R_1$=$R_3$=Me; $R_4$=$R_5$=$R_{12}$=$R_{13}$=$R_{15}$=$R_{16}$=$R_{23}$=$R_{25}$=$R_{26}$=H; $R_{10}$=is a group represented by formula (A); $R_{20}$=is a group represented by formula (U); and $R_{24}$=$R_{30}$=NH*C(S)N$R_{32}R_{33}$, are:

| CPD# | $R_{14}$ | $R_{22}$ | $R_{32}$ | $R_{33}$ | M.Pt. ° C. |
|---|---|---|---|---|---|
| 235 | Cl | H | H | CH$_2$CH$_3$ | 80–82 |
| 236 | Cl | H | H | Me | 80–82 |
| 237 | Cl | H | H | phenyl | 158.3–159 |
| 238 | Cl | H | H | 2-Cl-phenyl | 164.5–166 |
| 239 | Cl | H | H | 4-Cl-phenyl | 176–177.5 |
| 240 | Me | F | H | tetrahydrofuran-2-yl-methyl | 131.4–132 | and are named as follows:

235. 1-{4-[5-(4-Chlorobenzoyl)-1,2-dimethyl-1H-pyrrol-2-ylmethyl]phenyl}-3-ethyl-2-thiourea.
236. 1-{4-[5-(4-Chlorobenzoyl)-1,2-dimethyl-1H-pyrrol-2-ylmethyl]phenyl}-3-methyl-2-thiourea.
237. 1-{4-[5-(4-Chlorobenzoyl)-1,2-dimethyl-1H-pyrrol-2-ylmethyl]phenyl)-3-phenyl-2-thiourea.
238. 1-{4-[5-(4-Chlorobenzoyl)-1,2-dimethyl-1H-pyrrol-2-ylmethyl]phenyl}-3-(2-chlorophenyl)-2-thiourea.
239. 1-{4-[5-(4-Chlorobenzoyl)-1,2-dimethyl-1H-pyrrol-2-ylmethyl]phenyl}-3-(4-chlorophenyl)-2-thiourea.
240. 1-{3-Fluoro-4-[5-(4-methylbenzoyl)-1,2-dimethyl-1H-pyrrol-2-ylmethyl]phenyl}-3-(tetrahydrofuran-2-ylmethyl)-2-thiourea.

V. Compounds of formula I where $R_1$=$R_3$=Me; $R_4$=$R_5$=$R_{12}$=$R_{13}$=$R_{15}$=$R_{16}$=$R_{23}$=$R_{25}$=$R_{26}$=H; $R_{14}$=Cl; $R_{10}$=is a group represented by formula (A); $R_{20}$=is a group represented by formula (U); and $R_{24}$=$R_{30}$=NH*C(O)$R_{31}$, are:

| CPD# | $R_{22}$ | $R_{31}$ | M.Pt. ° C. |
|---|---|---|---|
| 241 | H | Me | 189–189.9 |
| 242 | H | CF$_3$ | 231.5–234.5 |
| 243 | H | CH$_2$F | 180.5–181.7 |
| 244 | F | Me | 184.3–185.1 |
| 245 | H | morpholino | 209.5–210.5 |
| 246 | H | 4-Me piperazino | 141.8–142.6 |
| 247 | H | piperazino | >280 |
| 248 | H | piperazino.HCl | >280 |
| 249 | H | pyrrolidino | 217.5–218.4 | and are named as follows:

241. N-{4-[5-(4-Chlorobenzoyl)-1,4-dimethyl-1H-pyrrol-2-ylmethyl]phenyl}acetamide.
242. N-{4-[5-(4-Chlorobenzoyl)-1,4-dimethyl-1H-pyrrol-2-ylmethyl]phenyl}trifluoroacetamide.
243. N-{4-[5-(4-Chlorobenzoyl)-1,4-dimethyl-1H-pyrrol-2-ylmethyl]phenyl}fluoroacetamide.
244. N-{3-Fluoro-4-[5-(4-chlorobenzoyl)-1,4-dimethyl-1H-pyrrol-2-ylmethyl]phenyl}actamide.
245. N-{4-[5-(4-Chlorobenzoyl)-1,4-dimethyl-1H-pyrrol-2-ylmethyl]phenyl}morpholin-4-ylcarboxamide.
246. N-{4-[5-(4-Chlorobenzoyl)-1,4-dimethyl-1H-pyrrol-2-ylmethyl]phenyl}-(4-methyl-piperazin-1-yl)carboxamide.
247. N-{4-[5-(4-Chlorobenzoyl)-1,4-dimethyl-1H-pyrrol-2-ylmethyl]phenyl}piperazin-1-yl-carboxamide.
248. N-{4-[5-(4-Chlorobenzoyl)-1,4-dimethyl-1H-pyrrol-2-ylmethyl]phenyl}piperazin-1-yl-carboxamide hydrochloride.
249. N-{4-[5-(4-Chlorobenzoyl)-1,4-dimethyl-1H-pyrrol-2-ylmethyl]phenyl}pyrrolidin-1-yl-carboxamide.

Compounds of formula I where $R_1$=Me; $R_4$=$R_5$=$R_{13}$=$R_{15}$=$R_{16}$=$R_{23}$=$R_{25}$=$R_{26}$=H; $R_{10}$=is a group represented by formula (A); $R_{20}$=is a group represented by formula (U); and $R_{24}$=$R_{30}$=NHH* are:

| CPD # | $R_3$ | $R_{12}$ | $R_{14}$ | $R_{22}$ | $R_{30}$ | M.Pt. ° C. |
|---|---|---|---|---|---|---|
| 250 | Me | H | Cl | H | NH$_2$ | 142.8–145.5 |
| 251 | Me | H | SMe | F | NH$_2$ | 199.1–199.7 |
| 252 | H | H | OMe | F | NH$_2$ | 146.4–147.7 |
| 253 | H | H | Me | F | NH$_2$ | 142.4–143 |
| 254 | H | H | H | F | NH$_2$ | 130.3–131.2 |
| 255 | Me | Me | Me | CN | NH$_2$ | 179.8–181.9 |
| 256 | Me | Me | Me | Cl | NH$_2$ | 120–121.5 |
| 257 | Me | H | H | F | NHC(O)CH(NH$_2$)CH(Me)$_2$(S) | 130.6–131.5 |
| 258 | Me | H | Me | Cl | NH$_2$ | |
| 259 | Me | H | CF$_3$ | Cl | NH$_2$ | 140–140.8 |
| 260 | H | Cl | H | F | NH$_2$ | 97.9–99 |
| 261 | H | OMe | H | F | NH$_2$ | 131.4–132.6 |
| 262 | Me | Me | Me | Cl | NH H*=COCH$_3$ | 153–155 | and are named as follows:

250. 4-[5-(4-Chlorobenzoyl)-1,4-dimethyl-1H-pyrrol-2-ylmethyl]aniline.
251. 3-Fluoro-4-[5-(4-methylthiobenzoyl)-1,4-dimethyl-1H-pyrrol-2-ylmethyl]aniline.
252. 3-Fluoro-4-[5-(4-methoxybenzoyl)-1-methyl-1H-pyrrol-2-ylmethyl]aniline.
253. 3-Fluoro-4-[5-(4-methylbenzoyl)-1-methyl-1H-pyrrol-2-ylmethyl]aniline.

254. 3-Fluoro-4-[5-benzoyl-1-methyl-1H-pyrrol-2-ylmethyl]aniline.
255. 3-Cyano-4-[5-(2,4-dimethylbenzoyl)-1,4-dimethyl-1H-pyrrol-2-ylmethyl]aniline.
256. 3-Chloro-4-[5-(2,4-dimethylbenzoyl)-1,4-dimethyl-1H-pyrrol-2-ylmethyl]aniline.
257. N-(S)-Valyl-3-fluoro-4-[5-benzoyl-1-methyl-1H-pyrrol-2-ylmethyl]aniline.
258. 3-Chloro-4-[5-(4-methylbenzoyl)-1,4-dimethyl-1H-pyrrol-2-ylmethyl]aniline, m/e=352 (M+H).
259. 3-Chloro-4-[5-(4-trifluoromethylbenzoyl)-1,4-dimethyl-1H-pyrrol-2-ylmethyl]aniline.
260. 3-Fluoro-4-[5-(2-chlorobenzoyl)-1-methyl-1H-pyrrol-2-ylmethyl]aniline.
261. 3-Fluoro-4-[5-(2-methoxybenzoyl)-1-methyl-1H-pyrrol-2-ylmethyl]aniline.
262. N-{3-Chloro-4-[5-(2,4-dimethylbenzoyl)-1,4-dimethyl-1H-pyrrol-2-ylmethyl]phenyl}-acetamide.

VIIa. Compounds of formula I where $R_1=R_3=Me$; $R_4=R_5=R_{12}=R_{15}=R_{16}=H$; $R_{14}=Cl$; $R_{10}=$is a group represented by formula (A); $R_{20}=$is a group represented by formula (V); and $R_{30}=NH^*SO_2R_{31}$, are:

| CPD# | $R_{13}$ | $R_{22}$ | $R_{31}$ | M.Pt. °C. |
|---|---|---|---|---|
| 263 | H | H | Me | 191 |
| 264 | H | H | Me Na$^+$ | >280 |
| 265 | H | H | Me HCl | 199–200 |
| 266 | H | H | CH$_2$CH$_3$ | 181–182 |
| 267 | H | H | (CH$_2$)$_2$OH | 160–161 |
| 268 | Cl | H | Me | 161.7–162.3 |
| 269 | Cl | H | CH$_2$CH$_3$ | 67.8–78.8 |
| 270 | Cl | H | 2-thienyl | 111–114 | and are named as follows:
263. N-{2-[5-(4-Chlorobenzoyl)-1,4-dimethyl-1H-pyrrol-2-ylmethyl]pyridin-5-yl}-methanesufonamide.
264. N-{2-[5-(4-Chlorobenzoyl)-1,4-dimethyl-1H-pyrrol-2-ylmethyl]pyridin-5-yl}-methansulfonamide sodium salt.
265. N-{2-[5-(4-Chlorobenzoyl)-1,4-dimethyl-1H-pyrrol-2-ylmethyl]pyridin-5-yl}-methanesulfonamide hydrochloride.
266. N-{2-[5-(4-Chlorobenzoyl)-1,4-dimethyl-1H-pyrrol-2-ylmethyl]pyridin-5-yl}ethanesulfonamide.
267. N-{2-[5-(4-Chlorobenzoyl)-1,4-dimethyl-1H-pyrrol-2-ylmethyl]pyridin-5-yl}-2-(hydroxy)ethanesulfonamide.
268. N-{2-[5-(3,4-Dichlorobenzoyl)-1,4-dimethyl-1H-pyrrol-2-ylmethyl]pyridin-5-yl}-methanesulfonamide.
269. N-{2-[5-(3,4-Dichlorobenzoyl)-1,4-dimethyl-1H-pyrrol-2-ylmethyl]pyridin-5-yl}ethanesulfonamide.
270. N-{2-[5-(3,4-Dichlorobenzoyl)-1,4-dimethyl-1H-pyrrol-2-ylmethyl]pyridin-5-yl}-thiopen-2-ylsulfonamide.

VIIb. Compounds of formula I where $R_1=Me$; $R_5=R_{13}=R_{15}=R_{16}=H$; $R_{14}=Me$; $R_{10}=$is a group represented by formula (A); $R_{20}=$is a group represented by formula (V); and $R_{30}=NH^*SO_2R_{31}$, are:

| CPD# | $R_3$ | $R_4$ | $R_{12}$ | $R_{22}$ | $R_{31}$ | M.Pt. °C. |
|---|---|---|---|---|---|---|
| 271 | H | H | H | H | Me | 158.7–159.5 |
| 272 | H | H | H | H | (CH$_2$)$_2$OH .HCl | 129 |
| 273 | Me | H | H | H | Me | 179–180 |
| 274 | Me | H | H | H | CH$_2$CH$_3$ | 56 |
| 275 | Me | H | H | H | CH(CH$_3$)$_2$ | 73 |
| 276 | H | H | H | 3-Cl | Me | 188.2–190 |
| 277 | H | H | Me | H | Me .HCl | 81–83.5 |
| 278 | H | Cl | H | H | Me | 142.5–142.9 | and are named as follows:
271. N-{2-[5-(4-Methylbenzoyl)-1-methyl-1H-pyrrol-2-ylmethyl]pyridin-5-yl}methanesulfonamide.
272. N-{2-[5-(4-Methylbenzoyl)-1,4-dimethyl-1H-pyrrol-2-ylmethyl]pyridin-5-yl}-2-(hydroxy)-ethanesulfonamide hydrochloride.
273. N-{2-[5-(4-Methylbenzoyl)-1,4-dimethyl-1H-pyrrol-2-ylmethyl]pyridin-5-yl}methanesulfonamide.
274. N-{2-[5-(4-Methylbenzoyl)-1,4-dimethyl-1H-pyrrol-2-ylmethyl]pyridin-5-yl}ethanesulfonamide.
275. N-{2-[5-(4-Methylbenzoyl)-1,4-dimethyl-1H-pyrrol-2-ylmethyl]pyridin-5-yl}(2-propane)sulfonamide.
276. N-{3-Chloro-2-[5-(4-methylbenzoyl)-1-methyl-1H-pyrrol-2-ylmethyl]pyridin-5-yl}-methanesulfonamide.
277. N-{2-[5-(2,4-Dimethylbenzoyl)-1-methyl-1H-pyrrol-2-ylmethyl]pyridin-5-yl}-methanesulfonalide hydrochloride salt.
278. N-{2-[5-(4-Methylbenzoyl)-1-methyl-4-chloro-1H-pyrrol-2-ylmethyl]pyridin-5-yl}-methanesulfonamide.

VIIc. Compounds of formula I where $R_1=Me$; $R_4=R_5=R_{12}=R_{13}=R_{15}=R_{16}=H$; $R_{10}=$is a group represented by formula (A); $R_{20}=$is a group represented by formula (V); and $R_{30}=NH^*SO_2R_{31}$, are:

| CPD# | $R_3$ | $R_{14}$ | $R_{22}$ | $R_{31}$ | M.Pt. °C. |
|---|---|---|---|---|---|
| 279 | Me | H | H | Me .HCl | 204–206 |
| 280 | Me | H | H | CH$_2$CH$_3$ | 117–118 |
| 281 | Me | H | H | (CH$_2$)$_2$OH.HCl | 151.5–153 |
| 282 | Me | SMe | H | CH$_2$CH$_3$ | 210–215 |
| 283 | Me | SMe | H | Me | 175 |
| 284 | Me | OMe | 3-Cl | Me | 178–180 |
| 285 | Me | OMe | H | CH$_2$CH$_3$ | 53.8–64.7 |
| 286 | Me | F | H | CH$_2$CH$_3$ | 145.5–146.2 |
| 287 | Me | F | H | Me | 166.1–167.2 |
| 288 | H | OMe | H | Me | 141–142 |
| 289 | Me | OMe | H | Me | 149.4–150.2 | and are named as:
279. N-{2-[5-Benzoyl-1,4-dimethyl-1H-pyrrol-2-ylmethyl]pyridin-5-yl}methanesulfonamide hydrochloride.
280. N-{2-[5-Benzoyl-1,4-dimethyl-1H-pyrrol-2-ylmethyl]pyridin-5-yl}ethanesulfonamide.
281. N-{2-[5-benzoyl-1,4-dimethyl-1H-pyrrol-2-ylmethyl]pyridin-5-yl}-2-(hydroxy)-ethanesulfonamide.
282. N-{2-[5-(4-Methylthiobenzoyl)-1,4-dimethyl-1H-pyrrol-2-ylmethyl]pyridin-5-yl}ethanesulfonamide.
283. N-{2-[5-(4-Methylthiobenzoyl)-1,4-dimethyl-1H-pyrrol-2-ylmethyl]pyridin-5-yl}-methanesulfonamide.
284. N-{3-Chloro-2-[5-(4-methoxybenzoyl)-1,4-dimethyl-1H-pyrrol-2-ylmethyl]pyridin-5-yl}-methanesulfonamide.
285. N-{2-[5-(4-Methoxybenzoyl)-1,4-dimethyl-1H-pyrrol-2-ylmethyl]pyridin-5-yl}ethanesulfonamide.
286. N-{2-[5-(4-Fluorobenzoyl)-1,4-dimethyl-1H-pyrrol-2-ylmethyl]pyridin-5-yl}ethanesulfonamide.
287. N-{2-[5-(4-Fluorobenzoyl)-1,4-dimethyl-1H-pyrrol-2-ylmethyl]pyridin-5-yl}-methanesulfonamide.
288. N-{2-[5-(4-Methoxybenzoyl)-1-methyl-1H-pyrrol-2-ylmethyl]pyridin-5-yl}-methanesulfonanide.

289. N-{2-[5-(4-Methoxybenzoyl)-1,4-dimethyl-1H-pyrrol-2-ylmethyl]pyridin-5-yl}-methanesulfonamide.

VIII. Compounds of formula I where $R_1$=Me; $R_4$=$R_5$=$R_{13}$=$R_{15}$=$R_{16}$=H; $R_{10}$=is a group represented by formula (A); $R_{20}$=is a group represented by formula (V); and $R_{30}$=NH*SO$_2$NR$_{32}$R$_{34}$, are:

| CPD# | $R_{12}$ | $R_{14}$ | $R_3$ | $R_{22}$ | $R_{32}$ | $R_{34}$ | M.Pt. °C. |
|---|---|---|---|---|---|---|---|
| 290 | H | Cl | Me | H | Me | Me | 154–155.9 |
| 291 | H | Cl | Me | H | H | H | 170–171 |
| 292 | H | Me | H | H | Me | Me | 135–136.5 |
| 293 | H | Me | H | H | H | H | 168.8–169.1 |
| 294 | H | H | Me | H | Me | Me | 146–146.6 |
| 295 | H | H | Me | H | H | H | 162–163 |
| 296 | H | SMe | Me | H | Me | Me | 154.9–159.5 |
| 297 | H | OMe | Me | 3-Cl | H | H | 179.8–180.2 |
| 298 | H | Cl | Me | H | H | Me | 175.5–176.1 |
| 299 | H | Cl | Me | H | H | CH$_2$CH$_3$ | 167.3–168.1 |
| 300 | H | Me | H | H | H | CH$_2$CH$_3$ | 162–163.7 |
| 301 | H | SMe | Me | H | H | H | 175.3–175.7 |
| 302 | H | F | Me | H | Me | Me | 117.3–117.8 |
| 303 | H | Me | H | H | H | Me | 60.3–61.3 |
| 304 | H | F | Me | H | H | Me | 137–142.2 |
| 305 | H | F | Me | H | H | CH$_2$CH$_3$ | 163–163.5 |
| 306 | H | OMe | H | H | H | H | 179.8–180.2 |
| 307 | Me | Me | H | H | H | Me | 124–130 | and are named as follows:
290. 1-{2-[5-(4-Chlorobenzoyl)-1,4-dimethyl-1H-pyrrol-2-ylmethyl]pyridin-5-yl}-3,3-dimethylsulfamide.
291. 1-{2-[5-(4-Chlorobenzoyl)-1,4-dimethyl-1H-pyrrol-2-ylmethyl]pyridin-5-yl}sulfamide.
292. 1-{2-[5-(4-Methylbenzoyl)-1-methyl-1H-pyrrol-2-ylmethyl]pyridin-5-yl}-3,3-dimethylsulfamide.
293. 1-{2-[5-(4-Methylbenzoyl)-1-methyl-1H-pyrrol-2-ylmethyl]pyridin-5-yl}sulfamide.
294. 1-{2-[5-Benzoyl-1,4-dimethyl-1H-pyrrol-2-ylmethyl]pyridin-5-yl}-3,3-dimethylsulfamide.
295. 1-{2-[5-benzoyl-1,4-dimethyl-1H-pyrrol-2-ylmethyl]pyridin-5-yl}sulfamide.
296. 1-{2-[5-(4-Methylthiobenzoyl)-1,4-dimethyl-1H-pyrrol-2-ylmethyl]pyridin-5-yl}-3,3-dimethylsulfamide.
297. 1-{3-Chloro-2-[5-(4-methoxybenzoyl)-1,4-dimethyl-1H-pyrrol-2-ylmethyl]pyridin-5-yl}-3,3-dimethylsulfamide.
298. 1-{2-[5-(4-Chlorobenzoyl)-1,4-dimethyl-1H-pyrrol-2-ylmethyl]pyridin-5-yl}-3-methylsulfamide.
299. 1-{2-[5-(4-Chlorobenzoyl)-1,4-dimethyl-1H-pyrrol-2-ylmethyl]pyridin-5-yl}-3-ethylsulfamide.
300. 1-{2-[5-(4-Chlorobenzoyl)-1-methyl-1H-pyrrol-2-ylmethyl]pyridin-5-yl}-3-ethylsulfamide.
301. 1-{2-[5-(4-Methylthiobenzoyl)-1,4-dimethyl-1H-pyrrol-2-ylmethyl]pyridin-5-yl}sulfamide.
302. 1-{2-[5-(4-Fluorobenzoyl)-1,4-dimethyl-1H-pyrrol-2-ylmethyl]pyridin-5-yl}-3,3-dimethylsulfamide.
303. 1-{2-[5-(4-Methylbenzoyl)-1-methyl-1H-pyrrol-2-ylmethyl]pyridin-5-yl}-3-methylsulfamide.
304. 1-{2-[5-(4-Fluorobenzoyl)-1,4-dimethyl-1H-pyrrol-2-ylmethyl]pyridin-5-yl}-3-methylsulfamide.
305. 1-{2-[5-(4-Fluorobenzoyl)-1,4-dimethyl-1H-pyrrol-2-ylmethyl]pyridin-5-yl}-3-ethylsulfamide.
306. 1-{2-[5-(4-Methoxybenzoyl)-1-methyl-1H-pyrrol-2-ylmethyl]pyridin-5-yl}sulfamide.
307. 1-{2-[5-(4-Dimethylbenzoyl)-1-methyl-1H-pyrrol-2-ylmethyl]pyridin-5-yl}-3-methylsulfamide.

IX. Compounds of formula I where $R_1$=$R_3$=Me; $R_4$=$R_5$=$R_{12}$=$R_{13}$=$R_{15}$=$R_{16}$=$R_{22}$=H; $R_{14}$=Cl; $R_{10}$=is a group represented by formula (A); $R_{20}$=is a group represented by formula (V); and $R_{30}$=NH*C(O)NR$_{32}$R$_{33}$, are:

| CPD# | $R_{32}$ | $R_{33}$ | M.Pt. °C. |
|---|---|---|---|
| 308 | Me | Me | 227–230 |
| 309 | H | Me | 234–235.5 |
| 310 | H | (CH$_2$)$_2$Cl | 181.8–182.9 |
| 311 | H | phenyl | 194.5–195.2 |
| 312 | H | 3-Cl-phenyl | 167.5–168.2 |
| 313 | H | 2-Cl-phenyl | 186–188 |

308. 1-{2-[5-(4-Chlorobenzoyl)-1,4-dimethyl-1H-pyrrol-2-ylmethyl]pyridin-5-yl}-3,3-dimethylurea.
309. 1-{2-[5-(4-Chlorobenzoyl)-1,4-dimethyl-1H-pyrrol-2-ylmethyl]pyridin-5-yl}-3-methylurea.
310. 1-{2-[5-(4-Chlorobenzoyl)-1,4-dimethyl-1H-pyrrol-2-ylmethyl]pyridin-5-yl}-3-(2-chloroethyl)urea.
311. 1-{2-[5-(4-Chlorobenzoyl)-1,4-dimethyl-1H-pyrrol-2-ylmethyl]pyridin-5-yl}-3-phenylurea.
312. 1-{2-[5-(4-Chlorobenzoyl)-1,4-dimethyl-1H-pyrrol-2-ylmethyl]pyridin-5-yl}-3-(3-chlorophenyl)urea.
313. 1-{2-[5-(4-Chlorobenzoyl)-1,4-dimethyl-1H-pyrrol-2-ylmethyl]pyridin-5-yl}-3-(2-chlorophenyl)urea.

X. Compounds of formula I where $R_1$=Me; $R_4$=$R_5$=$R_{12}$=$R_{13}$=$R_{15}$=$R_{16}$=$R_{22}$=H; $R_{10}$=is a group represented by formula (A); $R_{20}$=is a group represented by formula (V); and $R_{30}$=NH*C(S)NR$_{32}$R$_{33}$, are:

| CPD# | $R_3$ | $R_{14}$ | $R_{22}$ | $R_{32}$ | $R_{33}$ | M.Pt. °C. |
|---|---|---|---|---|---|---|
| 314 | Me | Cl | H | H | CH$_2$CH$_3$ | 139–142 |
| 315 | Me | Cl | H | H | Me | 135 |
| 316 | Me | Cl | H | H | phenyl | 154.2–155.5 |
| 317 | Me | Cl | H | H | cyclohexyl | 146–150 |
| 318 | Me | Cl | H | H | (CH$_2$)$_2$OMe | 136.1–137.9 |
| 319 | Me | Cl | H | H | tetrahydro-furan-2-ylmethyl | 130.6–133.1 |
| 320 | Me | Cl | H | H | CH$_2$CO$_2$Me | 155–156.5 |
| 321 | Me | Cl | H | H | cyclopropyl | 11O–122.5 |
| 322 | Me | Cl | H | H | (CH$_2$)$_2$-morpholine | 84–98 |
| 323 | Me | Cl | H | H | phenyl HCl.Salt | 172–174 |
| 324 | Me | Cl | H | H | 4-Cl-phenyl | 157.8–158.5 |
| 325 | Me | Cl | H | H | 3-Cl-phenyl | 157.5–159 |
| 326 | Me | Cl | H | H | 4-SMe-phenyl | 149–150 |
| 327 | H | Me | Cl | H | (CH$_2$)$_2$OMe | 172.4–174.2 |
| 328 | H | Me | Cl | H | tetrahydro-furan-2-ylmethyl | 150.1–150.8 | and are named as follows:
314. 1-{2-[5-(4-Chlorobenzoyl)-1,4-dimethyl-1H-pyrrol-2-ylmethyl]pyridin-5-yl}-3-ethyl-2-thiourea.
315. 1-{2-[5-(4-Chlorobenzoyl)-1,4-dimethyl-1H-pyrrol-2-ylmethyl]pyridin-5-yl}-3-methyl-2-thiourea.
316. 1-{2-[5-(4-Chlorobenzoyl)-1,4-dimethyl-1H-pyrrol-2-ylmethyl]pyridin-5-yl}-3-phenyl-2-thiourea.
317. 1-{2-[5-(4-Chlorobenzoyl)-1,4-dimethyl-1H-pyrrol-2-ylmethyl]pyridin-5-yl}-3-cyclohexyl-2-thiourea.
318. 1-{2-[5-(4-Chlorobenzoyl)-1,4-dimethyl-1H-pyrrol-2-ylmethyl]pyridin-5-yl}-3-(2-methoxyethyl)-2-thiourea.
319. 1-{2-[5-(4-Chlorobenzoyl)-1,4-dimethyl-1H-pyrrol-2-ylmethyl]pyridin-5-yl}-3-(tetrahydrofuran-2-ylmethyl)-2-thiourea.
320. 1-{2-[5-Chlorobenzoyl)-1,4-dimethyl-1H-pyrrol-2-ylmethyl]pyridin-5-yl}-3-[(methoxycarbonyl)methyl]-2-thiourea.

321. 1-{2-[5-(4-Chlorobenzoyl)-1,4-dimethyl-1H-pyrrol-2-ylmethyl]pyridin-5-yl}-3-cyclopropyl-2-thiourea.
322. 1-{2-[5-(4-Chlorobenzoyl)-1,4-dimethyl-1H-pyrrol-2-ylmethyl]pyridin-5-yl}-3-[2-(morpholin-4-yl)ethyl]-2-thiourea.
323. 1-{2-[5-(4-Chlorobenzoyl)-1,4-dimethyl-1H-pyrrol-2-ylmethyl]pyridin-5-yl}-3-phenyl-2-thiourea hydrochloride.
324. 1-{2-[5-(4-Chlorobenzoyl)-1,4-dimethyl-1H-pyrrol-2-ylmethyl]pyridin-5-yl}-3-(4-chlorophenyl)-2-thiourea.
325. 1-{2-[5-(4-Chlorobenzoyl)-1,4-dimethyl-1H-pyrrol-2-ylmethyl]pyridin-5-yl}-3-(3-chlorophenyl)-2-thiourea.
326. 1-{2-[5-(4-Chlorobenzoyl)-1,4-dimethyl-1H-pyrrol-2-ylmethyl]pyridin-5-yl}-3-(4-methylthiophenyl)-2-thiourea.
327. 1-{3-Chloro-2-[5-(4-methylbenzoyl)-1-methyl-1H-pyrrol-2-ylmethyl]pyridin-5-yl}-3-(2-methoxyethyl)-2-thiourea.
328. 1-{3-Chloro-2-[5-(4-methylbenzoyl)-1-methyl-1H-pyrrol-2-ylmethyl]pyridin-5-yl}-3-(tetrahydrofuran-2-ylmethyl)-2-thiourea.

XI. Compounds of formula I where $R_1=R_3=Me$; $R_4=R_5=R_{12}=R_{13}=R_{15}=R_{16}=R_{22}=H$; $R_{14}=Cl$; $R_{10}$=is a group represented by formula (A); $R_{20}$=is a group represented by formula (V); and $R_{30}=NH^*C(O)R_{31}$, are:

| CPD# | $R_{31}$ | M.Pt. °C. |
|---|---|---|
| 329 | Me | 194–195 |
| 330 | H | 166.6–167.7 |
| 331 | CH(NH$_2$)CH$_3$ .2HCl | 129–210 chiral (R) |
| 332 | morpholino | 243–244 | and are named as follows:
329. N-{2-[5-(4-Chlorobenzoyl)-1,4-dimethyl-1H-pyrrol-2-ylmethyl]pyridin-5-yl}acetamide.
330. N-{2-[5-(4-Chlorobenzoyl)-1,4-dimethyl-1H-pyrrol-2-ylmethyl]pyridin-5-yl}formamide.
331. (R)-N-{2-[5-(4-chlorobenzoyl)-1,4-dimethyl-1H-pyrrol-2-ylmethyl]pyridin-5-yl}alaninamide.
332. N-{2-[5-(4-chlorobenzoyl)-1,4-dimethyl-1H-pyrrol-2-ylmethyl]-pyridin-5-yl}morpholin-4-ylcarboxamide.

XII. Compounds of formula I where $R_1=Me$; $R_4=R_5=R_{13}=R_{15}=R_{16}=R_{22}=H$; $R_{10}$=is a group represented by formula (A); $R_{20}$=is a group represented by formula (V); and $R_{30}=NHH^*$ are:

| CPD# | $R_3$ | $R_{12}$ | $R_{14}$ | M.Pt. °C. |
|---|---|---|---|---|
| 333 | Me | H | Cl | 133.1–133.6 |
| 334 | Me | H | SMe | 152.6–153.7 |
| 335 | H | Me | Me | 238.9–240.2 | and are named as:
333. {2-[5-(4-Chlorobenzoyl)-1,4-dimethyl-1H-pyrrol-2-ylmethyl]pyridin-5-yl}amine.
334. {2-[5-(4-Methylthiobenzoyl)-1,4-dimethyl-1H-pyrrol-2-ylmethyl]pyridin-5-yl}amine.
335. {2-[5-(2,4-Dimethylbenzoyl)-1-methyl-1H-pyrrol-2-ylmethyl]pyridin-5-yl}amine.

Miscellaneous compounds:

I. Compounds of formula I where $R_1=R_3=Me$; $R_4=R_5=R_{13}=R_{22}=H$; $R_{20}$=is a group represented by formula (V); and $R_{24}=R_{30}=NHSO_2R_{31}$ are:

| CPD# | $R_{10}$ | $R_{31}$ | M.Pt. °C. |
|---|---|---|---|
| 336 | 2-thienyl | CH$_2$CH$_3$ .HCl | 166–167 |
| 337 | 2-thienyl | Me .HCl | 168–170.5 | and are named as follows:
336. N-{2-[5-Thenoyl-1,4-dimethyl-1H-pyrrol-2-ylmethyl]pyridin-5-yl}ethanesulfonamide hydrochloride.
337. N-{2-[5-Thenoyl-1,4-dimethyl-1H-pyrrol-2-ylmethyl]pyridin-5-yl}methanesulfonamide hydrochloride.

II. Compound of formula (I) where $R_{1=Me; R3}=R_4=R_{12}=R_{13}=R_{15}=R_{16}=R_{24}=R_{25}=R_{26}=H$; $R_{14}=Me$; $R_{10}$=is a group represented by formula (A); $R_{20}$=is a group represented by formula (U); and $R_{23}=R_{30}=NH^*SO_2R_{31}$, is:

| CPD# | $R_5$ | $R_{22}$ | $R_{31}$ | |
|---|---|---|---|---|
| 338 | H | H | Me | Foam | and is named as follows:
338. N-{3-[5-(4-Methylbenzoyl)-1-methyl-1H-pyrrol-2-ylmethyl]phenyl}methanesulfonamide.

III. Compounds of formula I where $R_1=Me$; $R_4=R_5=R_{13}=R_{23}=R_{25}=R_{26}=H$; $R_{20}$=is a group represented by formula (U); and $R_{24}=R_{30}=NH^*SO_2R_{31}$, are:

| CPD# | $R_{10}$ | $R_3$ | $R_{22}$ | $R_{31}$ | M.Pt. °C. |
|---|---|---|---|---|---|
| 339 | 2-thienyl | H | H | Me | 142–143 |
| 340 | 2-thienyl | Me | F | Me | 169–170 |
| 341 | 3-pyridyl | Me | H | Me | 130–132 | and are named as follows:
339. N-{4-[5-(2-thenoyl)-1-methyl-1H-pyrrol-2-ylmethyl]phenyl}methanesulfonamide.
340. N-{3-Fluoro-4-[5-(2-thenoyl)-1,4-dimethyl-1H-pyrrol-2-ylmethyl]phenyl}-methanesulfonamide.
341. N-{4-[5-(2-thenoyl)-1,4-dimethyl-1H-pyrrol-2-ylmethyl]phenyl}methanesulfonamide.

IV. Compounds of formula(I) where $R_1=Me$; $R_4=R_5=R_{13}=R_{23}=R_{25}=R_{26}=H$; $R_{20}$=is a group represented by formula (U); and $R_{24}=R_{30}=NH^*SO_2NR_{32}R_{34}$, is:

| CPD# | $R_{10}$ | $R_3$ | $R_{22}$ | $R_{32}$ | $R_{34}$ | M.Pt.° C. |
|---|---|---|---|---|---|---|
| 342 | 2-thienyl | Me | F | H | H | 204–205 | and is named as follows:
342. 1-{3-Fluoro-4-[5-(2-thenoyl)-1,4-dimethyl-1H-pyrrol-2-ylmethyl]phenyl}sulfamide.

V. Compounds of formula I where $R_4=R_5=R_{12}=R_{13}=R_{15}=R_{16}=R_{22}=R_{23}=R_{25}=R_{26}=H$; $R_{10}$=is a group represented by formula (A); $R_{20}$=is a group represented by formula (U); and $R_{24}=R_{30}$ are

| CPD# | $R_1$ | $R_3$ | $R_{14}$ | $R_{30}$ | M.Pt |
|------|-------|-------|----------|----------|------|
| 343  | Me    | Me    | Cl       | OH       |      |
| 344  | Me    | Me    | Cl       | $OSO_2NMe_2$ |   |
| 345  | H     | H     | SMe      | $NHSO_2Me$ | 188.7–189 | and are named as follows:

343. 4-{5-(4-Chlorobenzoyl)-1,4-dimethyl-1H-pyrrol-2-ylmethyl}phenol, m/e=340 (M+).
344. 1-N,N-dimethylaminosulfonyloxy-4-[5-(4-Chlorobenzoyl)-1,4-dimethyl-1H-pyrrol-2-ylmethyl]benzene, m/e=446 (M+).
345. N-{4-[5-(4-Methylthiobenzoyl)-1H-pyrrol-2-ylmethyl]phenyl}methanesulfonamide.

PREFERRED COMPOUNDS

Preferred compounds of this invention are those where:
(1) $R_1$, $R_3$, $R_4$, and $R_5$ are independently H or alkyl; more preferably H or Me; most preferably $R_1$ is Me; $R_3$ is H or Me; and $R_4$ and $R_5$ are H;
(2) $R_{10}$ is a group represented by formula (A);
(3) $R_{12}$ and $R_{16}$ are independently H, alkyl, hydroxy, alkyloxy, cyano, or halo; more preferably H, Me, OH, OMe, F, or Cl; most preferably H, Me, or OMe;
(4) $R_{13}$ is H or alkyl; more preferably H or Me; most preferably H;
(5) $R_{14}$ is H, halo, alkyl, dialkylamino, alkoxy, alkylthio, or cyano; more preferably H, Me, OMe, F, Cl, $NMe_2$, or SMe; most preferably H, F, Cl, Me, or OMe;
(6) $R_{15}$ is H or halo; more preferably H or Cl; most preferably H;
(7) $R_{20}$ is a group represented by formula (U) or (V); preferably (U);
(8) where $R_{20}$ is a group represented by formula (U):
  $R_{22}$ is H, halo, alkyl, cyano, or —$CF_3$; more preferably H, F, Cl, or CN; most preferably F, Cl, or CN;
  $R_{23}$ and $R_{25}$ are H;
  $R_{24}$ is $R_{30}$; and
  $R_{26}$ is H, alkyl, or halo; more preferably H, Me, F, or Cl; most preferably H or F;
(9) where $R_{20}$ is a group represented by the formula (V):
  $R_{22}$ is preferably meta to $R_{30}$ and is preferably H, F, Cl, or cyano; more preferably H, F, or Cl; most preferably H;
(10) $R_{30}$ is —NHH*, —NH*C(S)$R_{32}R_{33}$, —NH*$SO_2R_{31}$, or —NH*$SO_2NR_{32}R_{34}$; more preferably —NHH*, —NH*$SO_2R_{31}$, or —NH*$SO_2NR_{32}R_{34}$; most preferably —NH*$SO_2R_{31}$ or —NH*$SO_2NR_{32}R_{34}$
(11) $R_{31}$ is alkyl, 2-hydroxyethyl, 2,3-dihydroxypropyl, or —$(CH_2)_nR_{35}$ where n is 2 or 3 and $R_{35}$ is OMe, cycloamino, —$NMe_2$, or —$CO_2R_{27}$ where $R_{27}$ is alkyl; more preferably Me or 2-hydroxyethyl;
(12) $R_{32}$ is H or Me; more preferably H;
(13) $R_{34}$ is H, Me, 2-hydroxyethyl, or acetyl; more preferably H or Me; most preferably H; and pharmaceutically acceptable salts thereof.

A number of different substituent preferences have been given in the list above, and following any of these substituent preferences results in a compound of this invention that is more preferred than one in which the particular substituent preference is not followed. However, these substituent preferences are generally independent, although some preferences are mutually exclusive, and following more than one of the substituent preferences results in a more preferred compound than one in which fewer of the substituent preferences are followed. Thus, particularly preferred compounds of this invention are those in which (to the extent possible) most of the above preferences are followed.

Exemplary particularly preferred compounds are:

N-{3-Cyano-4-[5-(4-chlorobenzoyl)-1,4-dimethyl-1H-pyrrol-2-ylmethyl]phenyl}-methanesulfonamide.

N-{3-Fluoro-4-[5-(4-methylbenzoyl)-1-methyl-1H-pyrrol-2-ylmethyl]phenyl}-2-(hydroxy)ethanesulfonamide.

N-{3-Fluoro-4-[5-(2,4-dimethylbenzoyl)-1-methyl-1H-pyrrol-2-ylmethyl]phenyl}-2-(hydroxy)ethanesulfonamide.

N-{3-Fluoro-4-[5-(2-methoxybenzoyl)-1-methyl-1H-pyrrol-2-ylmethyl]phenyl}-methanesulfonamide.

N-{3-Fluoro-4-[5-(4-methoxybenzoyl)-1,4-dimethyl-1H-pyrrol-2-ylmethyl]phenyl}-2-(hydroxy)ethanesulfonamide.

1-{4-[5-(4-Chlorobenzoyl)-1,4-dimethyl-1H-pyrrol-2-ylmethyl]phenyl}-3,3-dimethylsulfamide.

1-{3-Fluoro-4-[5-(4-chlorobenzoyl)-1,4-dimethyl-1H-pyrrol-2-ylmethyl]phenyl}sulfamide.

1-{3-Cyano-4-[5-(4-methoxybenzoyl)-1-methyl-1H-pyrrol-2-ylmethyl]phenyl}sulfamide.

1-{4-[5-(4-Chlorobenzoyl)-1,4-dimethyl-1H-pyrrol-2-ylmethyl]phenyl}-3-methyl-2-thiourea.

N-{2-[5-(4-Chlorobenzoyl)-1,4-dimethyl-1H-pyrrol-2-ylmethyl]pyridin-5-yl}-methanesulfonamide.

N-{3-Chloro-2-[-5-(4-methoxybenzoyl)-1,4-dimethyl-1H-pyrrol-2-ylmethyl]pyridin-5-yl}methanesulfonamide.

1-{2-[-5-(4-Methoxybenzoyl)-1-methyl-1H-pyrrol-2-ylmethyl]pyridin-5-yl}sulfamide.

{2-[5-(4-Thiomethylbenzoyl)-1,4-dimethyl-1H-pyrrol-2-ylmethyl]pyridin-5-yl}amine.

4-[5-(4-Chlorobenzoyl)-1,4-dimethyl-1H-pyrrol-2-ylmethyl]phenol.

N-{2-[5-(4-Methylbenzoyl)-1-methyl-1H-pyrrol-2-ylmethyl]pyridin-5-yl}methanesulfonamide.

1-{3-Fluoro-4-[5-(2,4-dimethylbenzoyl)-1-methyl-1H-pyrrol-2-ylmethyl]-phenyl}sulfamide.

N-{2-[5-(4-Methoxybenzoyl)-1-methyl-1H-pyrrol-2-ylmethyl]pyridin-5-yl}methanesulfonamide.

N-{3,5-Difluoro-4-[5-benzoyl-1-methyl-1H-pyrrol-2-ylmethyl]phenyl}-2-(hydroxy)-ethanesulfonamide.

N-{3-Fluoro-4-[5-(2-methoxybenzoyl)-1-methyl-1H-pyrrol-2-ylmethyl]phenyl}-2-(hydroxy)ethanesulfonamide.

N-{3-Fluoro-4-[5-(2-methyl-4-methoxybenzoyl)-1-methyl-1H-pyrrol-2-ylmethyl]-phenyl}-2-(hydroxy)ethanesulfonamide.

N-{3-Fluoro-4-[5-(2-chloro-4-methoxybenzoyl)-1-methyl-1H-pyrrol-2-ylmethyl]phenyl}methanesulfonamide.

N-{3-Fluoro-4-[5-(2-methoxy-4-methyl)-1-methyl-1H-pyrrol-2-ylmethyl]phenyl}-2-(hydroxy)ethanesulfonamide.

N-{3-fluoro-4-[5-benzoyl-1-methyl-1H-pyrrol-2-ylmethyl]phenyl}-2-(hydroxy)-ethanesulfonamide.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., or are prepared by methods known to those skilled in the art following procedures set forth in references such as *Fieser and Fieser's Reagents for Organic Synthesis*, Volumes 1–15 (John Wiley and Sons, 1991); *Rodd's Chemistry of Carbon Compounds*, Volumes 1–5 and Supplementals (Elsevier Science Publishers, 1989); and *Organic Reactions*, Volumes 1–40 (John Wiley and Sons, 1991). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In general, compounds of formula I are prepared by modification of 5-aroylpyrrol-2-ylmethylanilines ("anilines") or 5-aroylpyrrol-2-ylmethylpyridinamines ("pyridinamines"). These anilines or pyridinamines, which will sometimes be referred to later as compounds of formula Ia, are compounds of formula I where $R_{30}$ is —$NH_2$; so they are both compounds of this invention and are also intermediates to further compounds of this invention.

For convenience in the synthetic schemes following, $R_{20}$ (with the exception of the $R_{30}$ substituent thereon), will be denoted by —Q—. The use of —Q—$R_{30}$ to denote $R_{20}$ does not imply that $R_{20}$ is substituted only with $R_{30}$; $R_{20}$ may contain any other substituents within the scope described in the Summary of the Invention (or as specifically limited in a particular reaction sequence).

Schemes A, B, C and D describe alternative methods to generate the compounds of formula Ia.

Scheme A

The aniline/pyridinamine of formula Ia can be prepared from a pyrrole-2-acetate 2 by the method shown in Scheme A.

Step 1:

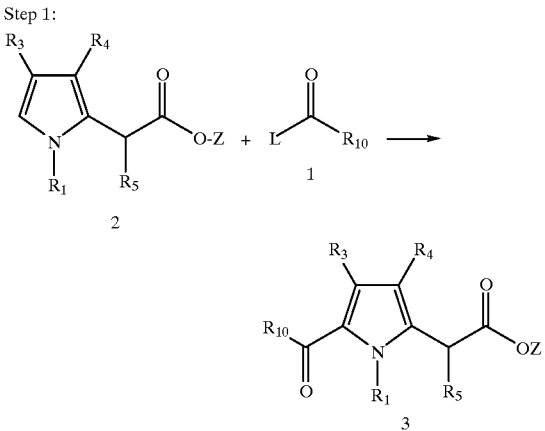

Step 2:

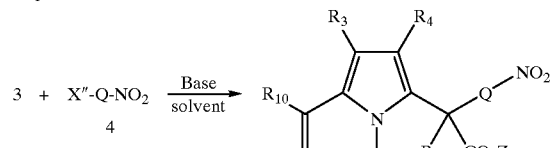

Step 3:

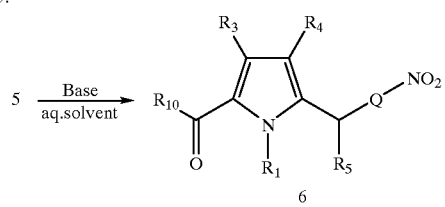

Step 4:

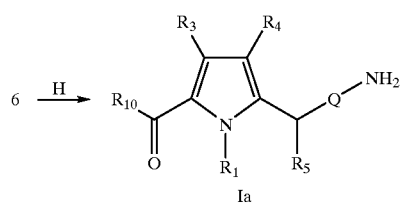

Step 3,4 (alternate)

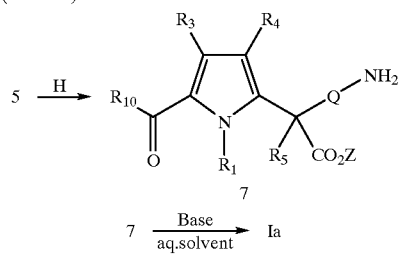

In Step 1, a 5-aroylpyrrole-2-acetate 3 is prepared by acylating a pyrrole-2-acetate 2, where $R_1$ is not hydrogen and Z is alkyl (particularly Me or ethyl) with an acylating agent of formula 1, where $R_{10}$ is as defined in the Summary of the Invention (except that $R_{14}$ is not an amino or alkylamino group) and L is a leaving group under acylating conditions [such as halo (particularly Cl), dialkylamino (particularly —$NMe_2$), or cycloamino (particularly morpholino)]. Suitable solvents for the reaction are halogenated and aromatic hydrocarbons (e.g. dichloroethane, xylenes and the like). When L is halo, the reaction proceeds on heating; when L is dialkylamino or cycloamino, the reaction proceeds in the presence of an acid halide such as phosphorus oxychloride, thionyl chloride, phosgene, oxalyl chloride, and the like (a Vilsmeier-Haack reaction).

In general, the compounds of formula 1, the pyrrole-2-acetates 2 and the 5-aroylpyrrole-2-acetates 3 are known to or can readily be synthesized by those of ordinary skill in the art. For example, synthesis of a pyrrole-2-acetate 2, where $R_1$ and $R_3$ are methyl is described by Stahley G. P., Marlett E. M., and Nelson G. E., *J. Org. Chem.*; 48:4423 (1983) and where $R_1$ is hydrogen and $R_5$ is H or alkyl is described by Schloemer, G. C., et. al., *J. Org. Chem.*; 59, 5230 (1994).

Also, a pyrrole-2-acetate 2 where $R_5$ is alkyl, can be prepared by reacting a pyrrole-2-acetate 2 where $R_5$ is hydrogen, with an alkylating agent $R_5L$ where L is a leaving group under alkylating conditions, such as halo, methanesulfonate, p-toluenesulfonate and the like. The reaction is carried out in the presence of a base (e.g., cesium carbonate, sodium hydride, or potassium carbonate) in a suitable polar aprotic organic solvent such as ether, THF, dioxane, DMF and the like. However, it is preferable to introduce $R_5$ as the alkyl group, in Step (2) of the synthesis as described below.

The 5-aroylpyrrole-2-acetates 3, where $R_1$ is alkyl and $R_3$ is methylthio or where $R_1$ and $R_5$ together form —$(CH_2)_2$—, and their synthesis are described in Muchowski, J. M.; Galeazzi, E., et al., *J. Med. Chem.* 32, 1202–1207, (1989).

Certain 5-aroylpyrrole-2-acetates 3 are also commercially available. For example the sodium salts of zomepirac, 5-(4-chlorobenzoyl)-1,4-dimethylpyrrole-2-acetate and tolmetin, 5-(4-methyl-benzoyl)-1-methylpyrrole-2-acetate are available from Sigma Chemical Company.

If a compound of formula 3 is obtained as an acid or salt, it is converted to an alkyl (preferably Me or ethyl) or an allyl ester prior to Step 2. The allyl ester is preferred when —Q— in compound 5 contains an electron withdrawing group such as a halo group meta to the nitro group or a base sensitive group such as a cyano group as one of the substituents. The alkyl or allyl ester is prepared by reacting the alkali metal salt of compound 3 with an alkylating agent such as an alkyl (preferably Me or ethyl) or allyl halide (e.g., Cl or Br). Suitable solvents for the reaction are polar aprotic organic solvents. If compound 3 is obtained as an alkyl ester (e.g., Z=Me or ethyl) but the allyl ester is preferred, the alkyl ester is converted to the corresponding allyl ester by heating it in an excess of allyl alcohol, in the presence of a suitable basic catalyst such as titanium isopropoxide.

In Step 2, a 2-(5-aroylpyrrol-2-yl)-2-(nitrophenyl/nitropyridyl)acetate 5 is prepared by nucleophilic substitution of X" in a nitro compound of formula 4, where X" is a leaving group under arylation conditions (e.g., Cl, F, —$OSO_2Me$, —$OSO_2CF_3$, and the like) by a 5-aroylpyrrole-2-acetate 3. The reaction is carried out in the presence of a strong base (e.g., sodium or potassium hydride, lithium diisopropylamide and the like) under an inert atmosphere (e.g., argon or nitrogen). Suitable solvents are aprotic organic solvents (e.g., tetrahydrofuran, dimethylformamide, and the like). Additionally, a compound of formula 5 where $R_5$ is alkyl, can be prepared from a compound of formula 3 where $R_5$ is hydrogen, by carrying out the above arylation procedure in the presence of an alkylating agent $R_5L$, where L is a leaving group under alkylating condition Compounds of formula 4 are commercially available or can be synthesized by one of ordinary skill in the art.

In Step 3, a nitrobenzene/nitropyridine 6 is prepared by hydrolysis and decarboxylation of the ester group in a compound of formula 5. If compound 5 is the alkyl ester, the hydrolysis/decarboxylation proceeds on heating, in the presence of an aqueous solution of a suitable base (e.g., LiOH, NaOH and the like) and in a suitable organic solvent such as methanol, methoxyethanol, DMF, THF, or mixtures thereof (preferably a high boiling solvent such as methoxyethanol or DMF). If the decarboxylation does not occur during the hydrolysis, it is effected by acidifying the reaction mixture with an aqueous acid such as HCl to give the free acid, which undergoes decarboxylation either at ambient temperature or upon heating in a high boiling organic solvent.

If compound 5 is the allyl ester, the deprotection reaction proceeds at ambient temperature, in the presence of a palladium catalyst (e.g., tetrakis(triphenylphosphine) palladium), an allyl scavenger (e.g., morpholine or pyrrolidine) and under an inert atmosphere. Suitable solvents for the reaction are polar organic solvents (e.g., THF, dioxane, or DMF).

In Step 4, an aniline/pyridinamine of formula Ia is prepared by reducing the nitro group of nitrobenzene/nitropyridine 6 to an amino group. Suitable nitro group reducing conditions include iron metal with ammonium chloride in ethanol/water, nickel boride in acidic methanol or catalytic hydrogenation using a platinum or palladium catalyst (e.g., $PtO_2$ or Pd/C) in an alcoholic solvent (e.g., methanol or ethanol, preferably ethanol).

Alternatively, a compound of formula Ia can be prepared from an alkyl ester of compound 5 by carrying out the reduction of the nitro group to the amino group, followed by the hydrolysis and decarboxylation of the ester group in the resulting aniline/pyridinamine-acetate of formula 7, utilizing the reaction conditions described in Steps 4 and 3 above. In general, this alternative route for the synthesis of compounds of formula Ia is preferred over the hydrolysis/decarboxylation, followed by reduction sequence described in steps 3 and 4 above when 5 is the alkyl ester.

The synthesis of a (5-aroylpyrrol-2-ylmethyl)aniline and a [2-(5-aroylpyrrol-2-ylmethyl)-pyridin-5-yl}amine utilizing the reaction conditions described in Scheme A is given in Examples 1–6.

Scheme B

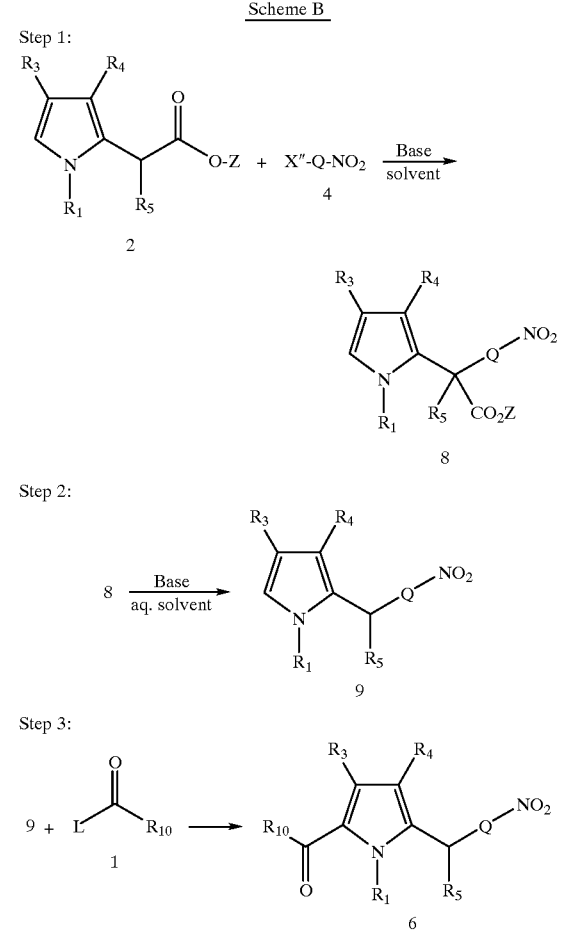

Step 4:

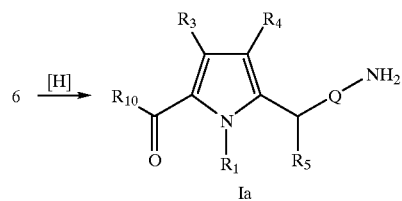

The aniline/pyridinamine of formula Ia can also be prepared from a pyrrole-2-acetate 2 by the method shown in Scheme B.

In Step 1, a 2-pyrrole-2-(nitrophenyl/nitropyridyl)acetate 8 is prepared by proceeding as in Step 2 of Scheme A but substituting a pyrrole-2-acetate 2 for a 5-aroylpyrrole-2-acetate 3.

In Step 2, a (pyrrol-2-ylmethyl)nitrobenzene/nitropyridine 9 is prepared by proceeding as in Step 3 of Scheme A but substituting a compound of formula 8 for a compound of formula 5.

In Step 3, a 2-(5-aroylpyrrol-2-ylmethyl)nitrobenzene/nitropyridine 6 is prepared from the compound of formula 9 by 5-acylation, utilizing the reaction conditions described in Step 1 of Scheme A.

In Step 4, an aniline/pyridinamine Ia is prepared by reduction of the nitro group in compound 6, utilizing the reaction conditions described in Step 4 of Scheme A.

Although Scheme B is generally suitable for synthesis of compounds of formula I that are within the scope of this invention, it is particularly suitable for the preparation of compounds of formula I where $R_{14}$ is an amino or alkylamino group. A detailed description of the synthesis of a compound of formula Ia by this method is given in Example 7.

Scheme C

The aniline/pyridinamine of formula Ia where $R_1$ is H or alkyl and $R_5$ is hydrogen, can also be prepared starting from a pyrrole as shown in Scheme C.

Step 1:

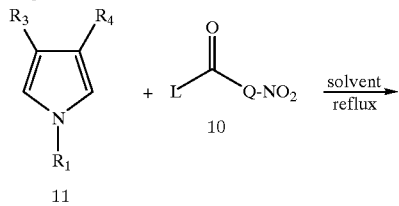

R1 = H or alkyl

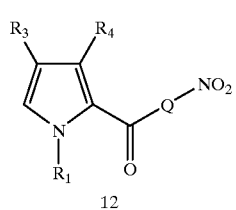

12

Step 2:

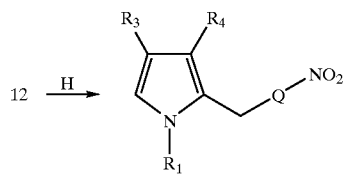

Step 3:

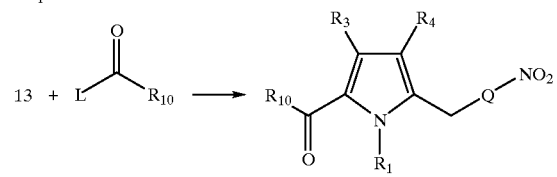

Step 4:

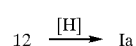

In Step 1, a 2-(nitroaroyl)pyrrole 12 is prepared by proceeding as in Step 1 of Scheme A but substituting an acylating agent of formula 10 and a pyrrole of formula 11 for the compounds of formula 1 and 2 respectively.

In Step 2, a (pyrrol-2-ylmethyl)nitrobenzene/nitropyridine 13 is prepared by reduction of the ketone group in compound 12 with a reducing agent selective for the ketone group, such as sodium cyanoborohydride in presence of a catalyst such as zinc iodide. Suitable solvents for this reaction include dihalogenated solvents (e.g., dichloromethane or dichloroethane).

A compound of formula Ia is then prepared from the compound of formula 13 by 5-acylation, followed by nitro group reduction in steps (3) and (4), utilizing the reaction conditions described in Steps 1 and 4 of Scheme A.

This route is particularly suited for preparing compounds of formula I where $R_{20}$ is a group represented by the formula (U) in which $R_{23}$ or $R_{25}$ is $R_{30}$. A detailed description of the synthesis of a compound of formula Ia by this method is given in Example 8.

Scheme D

The aniline/pyridinamine of formula Ia can also be prepared by the method shown in Scheme D.

Step 1:

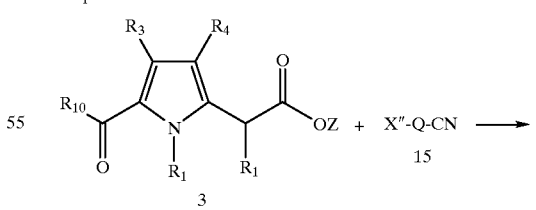

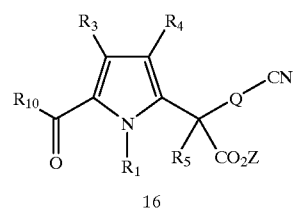

16

Step 2:

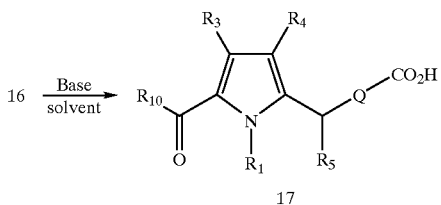

Step 3:

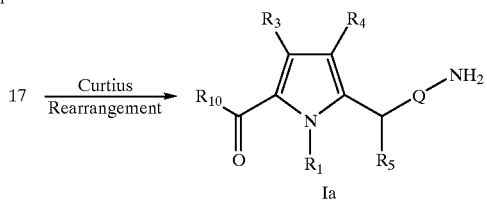

In Step 1, a 2-(5-aroylpyrrol-2-yl)-2-(cyanophenyl/cyanopyridyl)acetate 16 is prepared by proceeding as in Step 2 of Scheme A but substituting a nitrile of formula 15 for a nitro compound of formula 4.

In Step 2, a (5-aroylpyrrol-2-ylmethyl)benzoic/nicotinic acid 17 is prepared by proceeding as in Step 3 of Scheme A but substituting the compound of formula 16 for a compound of formula 5. The hydrolysis/decarboxylation reaction condition also causes the hydrolysis of the nitrite group.

In step 3, a compound of formula Ia is then prepared from a compound of formula 17, using a Curtius rearrangement reaction. Suitable conditions are those described in Yamada F., et al.; *J. Am. Chem. Soc.*; 6203, (1974) and Yamada, F., et al.; *Tetrahedron*, 30, 2151 (1974). The preparation of a compound of formula Ia by this method is described in Example 9.

Schemes E–I describe methods to prepare other compounds of formula I from compounds of formula Ia.

Scheme E

Scheme E describes the synthesis of compounds of formula I where $R_{30}$ is OH:

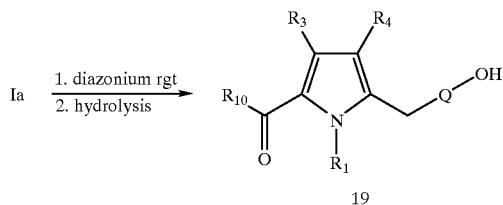

A compound of formula I where $R_{30}$ is —OH can be prepared by converting an aniline/pyridinamine of formula Ia to a diazonium salt, which upon hydrolysis in an aqueous acid gives the hydroxy group. The diazonium salt is prepared by reacting a compound of formula Ia with a nitrite salt (e.g., $NaNO_2$, $KNO_2$ and the like) in an aqueous solvent (e.g., water, aqueous acetic acid, aqueous organic mixtures such as acetic acid/acetone) or an alkyl nitrite such as isoamylnitrite in a non-aqueous solvent such as glacial acetic acid, acetone or a mixture thereof. The conversion of a compound of formula Ia to a compound of formula I where $R_{24}=R_{30}$ is —OH is described in detail in Example 10.

Scheme F

Scheme F describes the synthesis of compounds of formula I where $R_{30}$ is —NHC(O)$R_{31}$:

a.

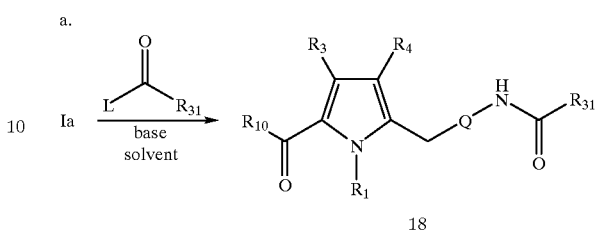

A compound of formula I where $R_{30}$ is an amide group can be prepared, either:
(a) by reacting an aniline/pyridinamine of formula Ia with an acylating reagent $R_{31}$COL, where L is a leaving group under acylating conditions, such as a halo (particularly Cl or Br) or imidazolide. Suitable solvents for the reaction include aprotic polar solvents (e.g., dichloromethane, THF, dioxane and the like.) When an acyl halide is used as the acylating agent the reaction is carried out in the presence of a non-nucleophilic organic base (e.g., triethylamine or pyridine, preferably pyridine); or
(b) by heating a compound of formula Ia with an acid anhydride. Suitable solvents for the reaction are THF, dioxane and the like. Detailed descriptions of the conversion of a compound of formula Ia to compounds of Formula I where $R_{31}$ is —NHC(O)CH$_3$ or —NHCHO are given in Examples 11 and 12.

Scheme G

Scheme G describes the synthesis of compounds of formula where $R_{30}$ is —NHC(X)NR$_{32}$R$_{33}$

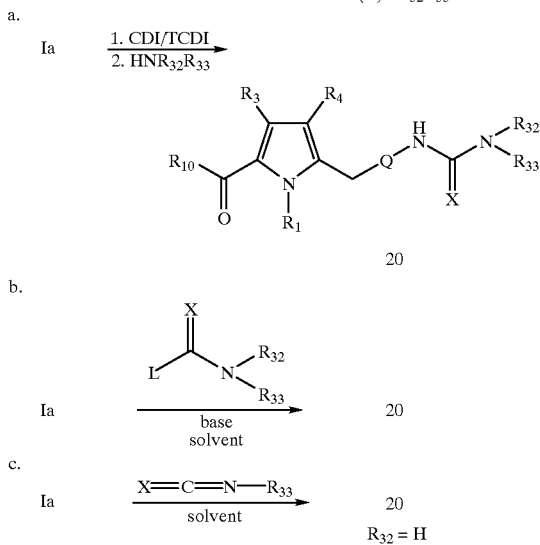

A compound of formula I where $R_{30}$ is a urea/thiourea group can be prepared, either:
(a) by reacting an aniline/pyridinamine of formula Ia with an activating agent such as carbonyl diimidazole/thiocarbonyl diimidazole, followed by nucleophilic displacement of the imidazole group with a primary or secondary amine. The reaction occurs at ambient temperature. Suitable solvents include polar organic solvents (e.g., THF, dioxane and the like);

(b) by reacting a compound of formula Ia with a carbamoyl/thiocarbamoyl halide. The reaction is carried out in the presence of a non-nucleophilic organic base. Suitable solvents for the reaction are dichloromethane, 1,2-dichloroethane, THF, or pyridine; or
(c) by reacting a compound of formula Ia with an isocyanate/isothiocyanate in an aprotic organic solvent (e.g., benzene, THF, DMF and the like). Detailed descriptions of the conversion of a compound of formula Ia to compounds of formula I where $R_{30}$ is —NHC(O)NHCH$_2$CH$_2$OH, —NHC(O)NMe$_2$, —NHC(O)NHMe, or —NHC(S)NHMe are given in Examples 13–16.

Scheme H

Scheme H is used to synthesize compounds of formula I where $R_{30}$ is —NHSO$_2$R$_{31}$ a.

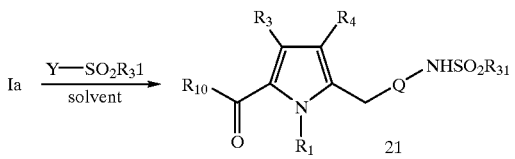

b.
Step 1:

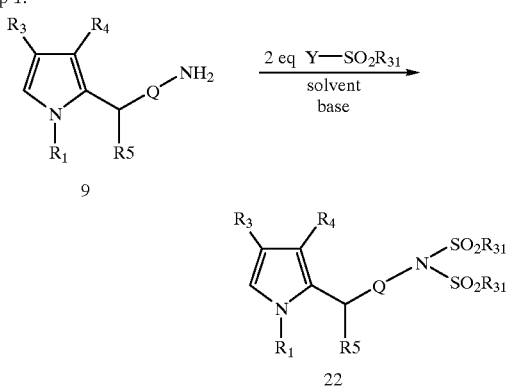

Step 2:

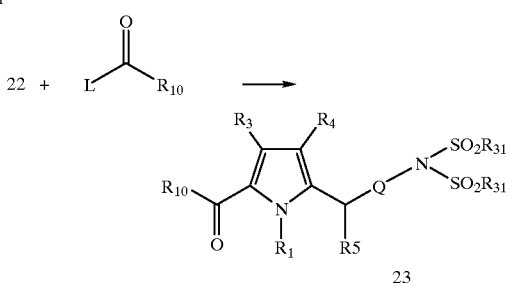

Step 3:

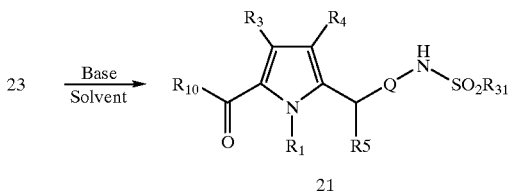

A compound of formula I where $R_{30}$ is a sulfonamide group can be prepared, either:
(a) by reacting an aniline/pyridinamine of formula Ia with a sulfonyl halide, utilizing the reaction conditions described in method (b) of Scheme G. Sulfonyl halides are commercially available or may be prepared by methods such as those described in (1) Langer, R. F.; *Can. J. Chem.*; 61, 1583–1592, (1983); (2) Aveta, R.; et. al.; *Gazetta Chimica Italiana*, 116, 649–652, (1986); (3) King, J. F. and Hillhouse, J. H.; *Can. J. Chem.*; 54, 498, (1976); and (4) Szymonifka, M. J. ane Heck, J. V.; *Tet. Lett.*; 30, 2869–2872, (1989). Detailed descriptions of the conversion of a compound of formula Ia to compounds of formula I where $R_{30}$ is —NHSO$_2$Me, —NHSO$_2$(CH$_2$)$_2$OH, —NHSO$_2$CH=CH$_2$, or —NHSO$_2$(CH$_2$)$_2$NMe$_2$ are given in Examples 17–20.
(b) by reacting a compound of formula 9 with two equivalents of a sulfonyl halide in the presence of a non-nucleophilic organic base to give a bis-sulfonamide. Suitable solvents for the reaction are halogenated organic solvents (e.g., dichloromethane, dichloroethane, CCl$_4$ and the like). The resulting bis-sulfonamide is 5-acylated under the reaction conditions described in Step 1 of Scheme A. Hydrolysis of one of the sulfonyl groups in presence of an inorganic base (e.g., LiOH, KOH and the like) gives a compound of formula I. Suitable solvents for the hydrolysis include THF, dioxane, DMF, and the like. A detailed description of the conversion of a compound of formula Ia to a compound of formula I, where $R_{30}$ is —NHSO$_2$Me by this procedure is given in Example 21.

Scheme I

Scheme I was used to prepare compounds of formula I where $R_{30}$ is —NHSO$_2$NR$_{32}$R$_{34}$ a.

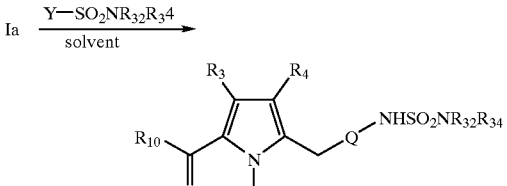

b.

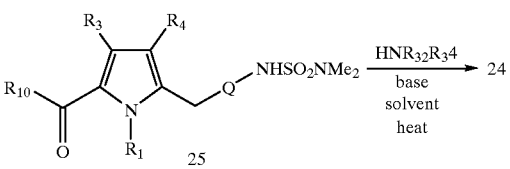

A compound of formula I where $R_{30}$ is a sulfamide group can be prepared, either:
(a) by reacting an aniline/pyridinamine of formula Ia with a sulfamoyl halide, utilizing the reaction conditions described in method (b) of Scheme G. Sulfamoyl halides are commercially available or may be prepared by methods such as those described in Graf, R; German Patent, 931225 (1952) and Catt, J. D. and Matler, W. L; *J. Org. Chem.*, 39, 566–568, (1974); or
(b) by an amine exchange reaction, in which a dimethyl sulfamide (prepared according to the method described above) is heated with an amine NHR$_{32}$R$_{34}$ in an aromatic hydrocarbon in presence of an excess amount of a non-nucleophilic organic base. Detailed descriptions of the conversion of a compound of formula Ia to a compound of formula I where $R_{30}$ is —NHSO$_2$NMe$_2$, —NHSO$_2$NH$_2$, or —NHSO$_2$-morpholine are given in Examples 22–24.

Additional Processes

Compounds of formula I and Ia having a group that would be unstable under the reaction conditions utilized in Schemes A–I can be prepared by the modification of another group present on a corresponding compound of formula I and Ia, e.g.; compounds of formula I containing a hydroxy group may be prepared by de-alkylation/benzylation of an alkyloxy/benzyloxy substituent; those containing an acid group, by hydrolysis of an ester group; and those containing a cyano, by displacement of a bromine atom on the corresponding compounds of formula I. Similarly, a compound of formula Ia having an alkenyl or alkynyl group can be prepared by reacting a corresponding compound of formula Ia containing a bromine or iodine atom with trimethylsilylacetylene under the Castro-Stephens reaction conditions. A detailed description of the conversion of a benzyloxy group to a hydroxy group; an ester group to an acid and a bromine atom to a cyano group are given in Examples 25–27 respectively. Furthermore, a compound of formula I and Ia can prepared by substitution of a group present on a corresponding compound of formula I and Ia, e.g., a compound of formula Ia where $R_{14}$ is H, or alkylthio may be conveniently prepared by dehalogenation/substitution of a chlorine atom on a corresponding compound of formula Ia. The conversion of a compound of formula Ia where $R_{14}$ is chloro to a corresponding compound of formula Ia where $R_{14}$ is H or methylthio is described in Examples 28 and 29 respectively.

General Utility

The compounds of the invention are inhibitors of prostaglandin G/H Synthase I and II (COX I and COX II), especially COX II, in vitro, and as such are expected to possess both anti-inflammatory and analgesic properties in vivo. See, for example, Goodman and Gilmans's "The Pharmacological Basis of Therapeutics," Ninth Edition, McGraw Hill, New York, 1996, Chapter 27. The compounds, and compositions containing them, are therefore useful as anti-inflammatory and analgesic agents in mammals, especially humans. They find utility in the treatment of inflammation and pain caused by diseases such as arthritis, gout, and autoimmune disorders (such as systemic lupus erythematosus, rheumatoid arthritis, and type I diabetes).

As inhibitors of prostaglandin G/H Synthase, the compounds of this invention are also expected to be useful in the prevention and treatment of cancer, in particular colon cancer. It has been shown that COX-2 gene expression is upregulated in human colorectal cancers and that drugs that inhibit prostaglandin G/H Synthase are effective in animal models of cancer (Eberhart, C. E., et. al.; *Gastroenterology*, (1994), 107, 1183–1188 and Ara, G., and Teicher, B. A., *Prostaglandins, Leukotrienes and Essential Fatty Acids*, (1996), 54, 3–16). In addition, there is epidemiological evidence that shows a correlation between use of drugs that inhibit prostaglandin G/H synthase and a reduced risk of developing colorectal cancer, (Heath, C. W. Jr., et. al.; *Cancer,* (1994), 74, No. 10, 2885–8).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients, (Rogers, J., et. al., *Neurology*, (1993), 43, 1609). Also, the use of drugs which inhibit prostaglandin. G/H synthase has been linked epidemiologically with a delayed onset of Alzheimer's disease, (Breitner, J. C. S., et. al., *Neurobiology of Aging*, (1995), 16, No. 4, 523 and *Neurology*, (1994), 44, 2073).

Testing

The anti-inflammatory activity of the compounds of this invention may be assayed by measuring the ability of the compound to inhibit COX I and COX II, especially COX II, in vitro, using a radiometric assay, as described in more detail in Example 31. It may also be assayed by in vivo assays such as the Rat Carrageenan Paw, and Rat Air-Pouch assays, as described in more detail in Examples 32 and 33. The analgesic activity of the compounds of this invention may be assayed by in vivo assays such as the Acetic Acid induced Rat Writhing Assay, and the rat arthritis pain model, as described in more detail in Example 34.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of formula I may range from approximately 0.1–75 mg per Kilogram body weight of the recipient per day; preferably about 5–20 mg/Kg/day. Thus, for administration to a 70 Kg person, the dosage range would most preferably be about 350 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intraveneous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions and are comprised of, in general, a compound of formula I in combination with at least one pharmaceutically acceptable excipient. Acceptable excipients are non-toxic, aid administration, and do not adversely affect the therapeutic benefit of the compound of formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent

41

(wt %) basis, from about 0.01–99.99 wt % of a compound of formula I based on the total formulation, with the balance being one or more suitable pharmaceutical excipients. Preferably, the compound is present at a level of about 1–80 wt %. Representative pharmaceutical formulations containing a compound of formula I are described in Example 30.

EXAMPLES

The following preparations and examples are given to enable those skilled in the art to more clearly understand and to practice the present invention. They should not be considered as limiting the scope of the invention, but merely as being illustrative and representative thereof.

Example 1

Synthesis of 3-fluoro-4-[5-benzoyl-1,4-dimethyl-1H-pyrrol-2-ylmethyl]aniline

Step (a)

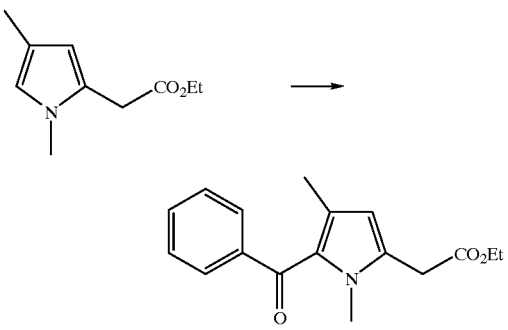

Ethyl 1,4-dimethylpyrrole-2-acetate (37.0 g, 0.19 mol), benzoyl chloride (54.3 g, 0.38 mol), and triethylamine (52.9 ml, 0.38 mol) were dissolved in xylenes (750 ml), and the reaction mixture was refluxed for 18 h under argon. The reaction mixture was cooled to room temperature and the solvent was removed in vacuo. Purification on a Florisil® column (hexane followed by hexane-ethyl acetate, 4:1) gave ethyl 5-benzoyl-1,4-dimethylpyrrole-2-acetate (30.45 g, 57%) as a solid.

Step (b)

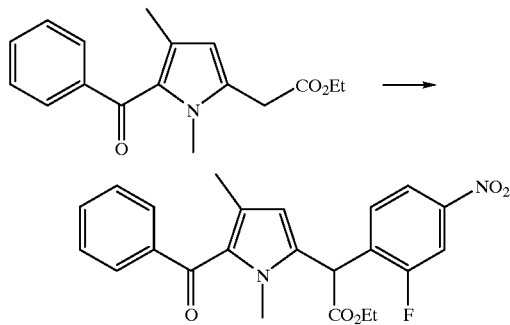

Ethyl 5-benzoyl-1,4-dimethylpyrrole-2-acetate (5.0 g, 17.5 mmol) [prepared as in Example 1, Step (a)], was dissolved in DMF (50 ml) and the solution was cooled in an ice bath to 0° C. under an argon atmosphere. Sodium hydride, 50%/mineral oil, (1.3 g, 27.1 mmol) was added, and after 5 min 3,4-difluoronitrobenzene (3.36 g, 21.1 mmol) was added to the reaction mixture. After 1 h the reaction mixture was poured into 10% HCl/ice and the product was extracted into ethyl acetate. The organic phase was washed with water, dried over sodium sulfate, and evaporated to dryness. Purification on a Florisil® column (hexane-ethyl acetate, 9:1) gave ethyl 2-(5-benzoyl-1,4-dimethylpyrrol-2-yl)-2-(2-fluoro-4-nitrophenyl)acetate (6.22 g, 84%) as a solid.

Step (c)

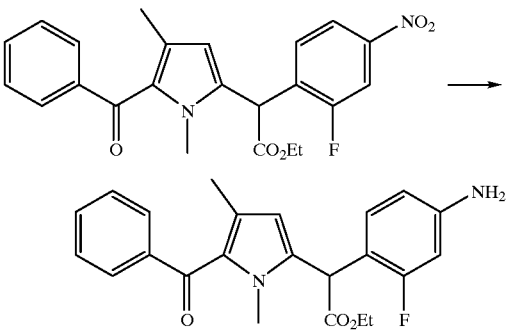

A mixture of ethyl 2-(5-benzoyl-1,4-dimethylpyrrol-2-yl)-2-(2-fluoro-4-nitrophenyl)-acetate (6.0 g, 14.1 mmol) [prepared as in Example 1, Step (b)], nickel boride (8.0 g, 62.4 mmol), hydrochloric acid (50 ml, 1M) and methanol (150 ml) was heated at reflux for 1 h. The reaction mixture was cooled and filtered through Celite®. After removing the methanol in vacuo, the resulting aqueous mixture was made basic with ammonium hydroxide, and the product was extracted into ethyl acetate. The organic layer was washed with brine and dried over sodium sulfate. Evaporation of the organic layer gave ethyl 2-(5-benzoyl-1,4-dimethyl-pyrrol-2-yl)-2-(2-fluoro-4-aminophenyl)acetate (5.3 g, 95%).

Step (d)

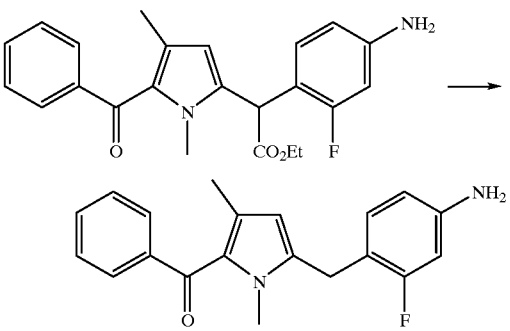

Ethyl 2-(5-benzoyl-1,4-dimethylpyrrol-2-yl)-2-(2-fluoro-4-aminophenyl)acetate (5.3 g, 13,4 mmol) [prepared as in Example 1, Step (c)] and 50% aqueous NaOH (5 ml) were dissolved in a 1:1 mixture of methanol/THF (100 ml), and the reaction mixture was refluxed for 30 min. After removing the solvents in vacuo, the residue was diluted with water and acidified with concentrated HCl. The product was extracted into ethyl acetate, and the organic layer was washed with brine, dried over sodium sulfate, and the solvent was removed under reduced pressure. The residue was re-dissolved in DMF (200 ml) and refluxed for 30 min. The reaction mixture was cooled, poured into water/ice, and the product was extracted into ethyl acetate. The organic layer was washed with water and dried over sodium sulfate. Evaporation of the solvent gave 3-fluoro-4-[5-benzoyl-1,4-dimethyl-1H-pyrrol-2-ylmethyl]aniline (3.12 g, 69%) as a solid.

Example 2

Synthesis of 4-[5-benzoyl-1,4-dimethyl-1H-pyrrol-2-ylmethyl]aniline

Step (a)

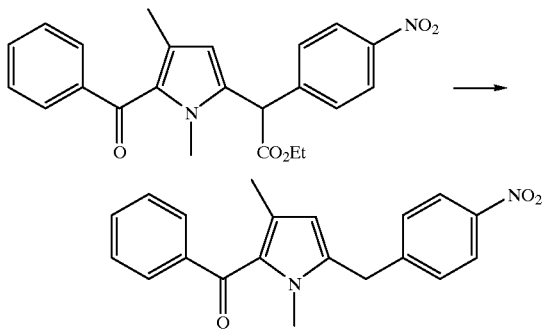

Ethyl 2-(5-benzoyl-1,4-dimethylpyrrol-2-yl)-2-(4-nitrophenyl)acetate (8.2 g, 20.2 mmol) [prepared by proceeding as described in Example 1, Steps (a) and (b)] was dissolved in a 1:1 mixture of methanol/THF (200 ml). An aqueous solution of LiOH (250 ml, 0.4M, 100.9 mmol) was added and the mixture was stirred at 60° C. for 2 h. The organic solvents were evaporated in vacuo, the aqueous residue was acidified with 10% HCl, and the product was extracted into ethyl acetate. The organic phase was washed with water, dried over sodium sulfate, and concentrated under vacuum. Purification on a Florisil® column (hexane-ethyl acetate, 4:1) gave 4-[5-benzoyl-1,4-dimethyl-1H-pyrrol-2-ylmethyl]-nitrobenzene (6.68 g, 99%) as a yellow solid.

Step (b)

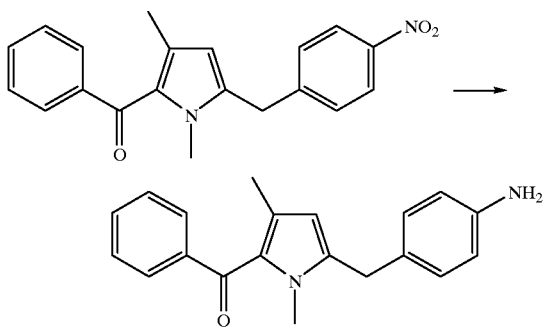

To a slurry of 4-[5-benzoyl-1,4-dimethyl-1H-pyrrol-2-ylmethyl]nitrobenzene (3.55 g, 10.6 mmol) [prepared as in Example 2, Step (a)] in methanol (170 ml) and hydrochloric acid (50 ml, 1M) was added nickel boride (3.41 g, 26.6 mmol), and the mixture was stirred at 75° C. for 15 h. The reaction mixture was cooled, basified with ammonium hydroxide and the product was extracted into ethyl acetate. The organic phase was washed with water and dried over sodium sulfate. Evaporation of the solvent gave 4-[5-benzoyl-1,4-dimethyl-1H-pyrrol-2-ylmethyl]aniline (3.11 g, 96%) as a pale yellow solid.

Example 3

Synthesis of 4-{1-[5-(4-chlorobenzoyl)-1,4-dimethyl-1H-pyrrol-2-yl]ethyl}aniline Step (a)

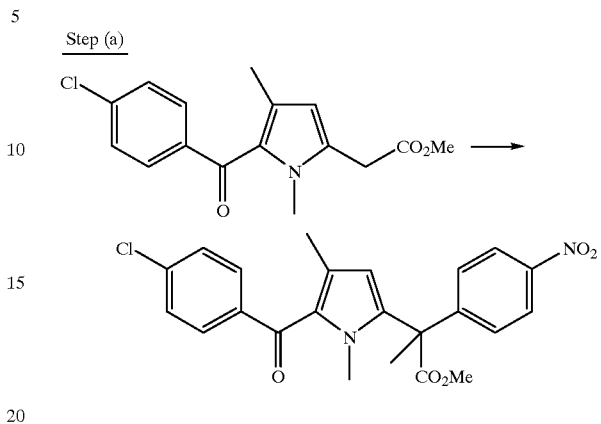

The methyl ester of zomepirac (6.12 g, 20.0 mmol) and 4-fluoronitrobenzene (2.65 ml, 25.0 mmol) were dissolved in DMF (65 ml) and sodium hydride, 60%/in mineral oil (1.68 g, 42 mmol) was added at room temperature. After 30 min methyl iodide (3.12 ml, 50 mmol) was added to the reaction mixture and the stirring was continued for an additional 15 min. The reaction mixture was poured into a mixture of 1N sodium bisulfate (20 ml) and ice-water and stirred overnight. The resulting solid was filtered and washed with water. Recrystallization from ethyl acetate-hexane gave methyl 2-[5-(4-chlorobenzoyl)-1,4-dimethylpyrrol-2-yl]-2-(4-nitro-phenyl)-2-methylacetate 7.85 g, 89%) as a solid, mp 180.9–181.7° C.

4-{1-[5-(4-Chlorobenzoyl)-1,4-dimethyl-1H-pyrrol-2-yl]ethyl}aniline can be prepared from methyl 2-{5-(4-chlorobenzoyl)-1,4-dimethylpyrrol-2-yl)-2-(4-nitrophenyl)-2-methyl-acetate by proceeding as in Example 1, Steps (c) and (d) or Example 2, Steps (a) and (b).

Example 4

Synthesis of 3-chloro-4-[5-(4-methylbenzoyl)-1-methyl-1H-pyrrol-2-ylmethyl]aniline Step (a)

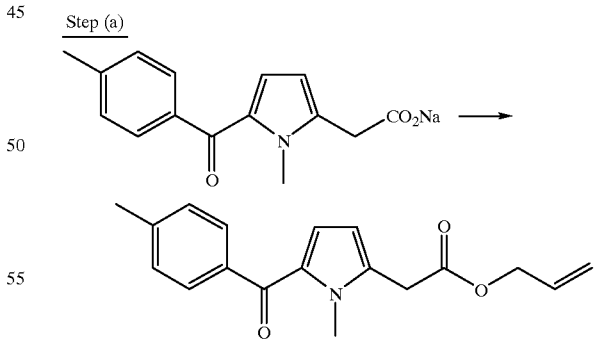

The sodium salt of tolmetin (15.0 g, 47.6 mmol) and allyl bromide (4.3 ml, 49.9 mmol) were dissolved in DMF (50 ml) and the mixture was stirred at room temperature until the esterification was complete (~30 h). The solvent was removed in vacuo and the residue was partitioned between ether and water. The organic layer was separated, washed with water, 1M sodium hydroxide, and brine, and dried over sodium sulfate. Evaporation gave allyl 5-(4- methylbenzoyl)-1-methylpyrrole-2-acetate (11.97 g, 85%) as a solid.

Step (b)

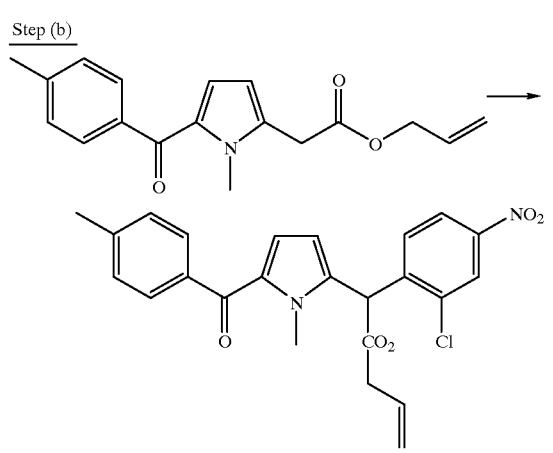

Allyl 5-(4-methylbenzoyl)-1-methylpyrrole-2-acetate (11.83 g, 39.8 mmol) [prepared as in Example 4, Step (a)] and 3,4-dichloronitrobenzene (7.64 g, 39.8 mmol) were dissolved in dry DMF (50 ml). The reaction mixture was cooled under nitrogen to 0° C. and sodium hydride powder (2.01 g, 83.5 mmol) was added in portions. After stirring at 0° C. for 30 min, the reaction mixture was warmed to room temperature and quenched with 1M HCl. The product was extracted into ether and the organic layer was washed with water and brine and dried over magnesium sulfate. Evaporation gave allyl 2-[(5-(4-methylbenzoyl)-1-methylpyrrol-2-yl]-2-(2-chloro-4-nitrophenyl)-acetate 17.15 g, 98%) as a foam.

Step (c)

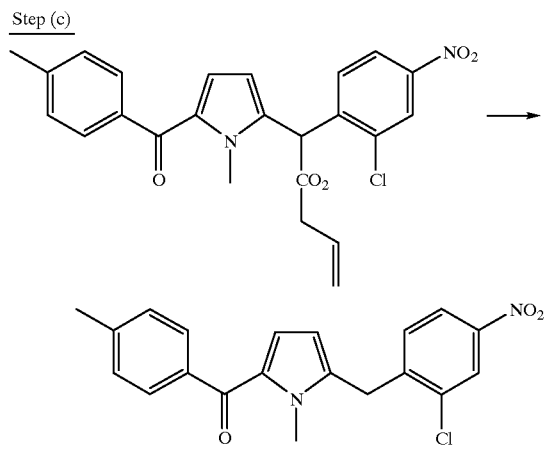

Allyl 2-[(5-(4-methylbenzoyl)-1-methylpyrrol-2-yl]-2-(2-chloro-4-nitrophenyl)acetate (17.15 g, 39.2 mmol [prepared as in Example 4, Step (b)] was dissolved in THF (100 ml) under nitrogen. Morpholine (34.2 ml, 391.7 mmol) and Pd(PPh$_3$)$_4$ (45 mg, 0.04 mmol) were added and the reaction mixture, which developed a white precipitate, was stirred for 20 min. The solvent was removed in vacuo and the residue was dissolved in ether. The ether layer was separated and washed with 1M sodium bisulfate and brine, and dried over magnesium sulfate. Evaporation gave 3-chloro-4-{5-(4-methylbenzoyl)-1-methyl-1H-pyrrol-2-yl-methyl}nitro-benzene (14.38 g, 99%) as a yellow oil.

Step (d)

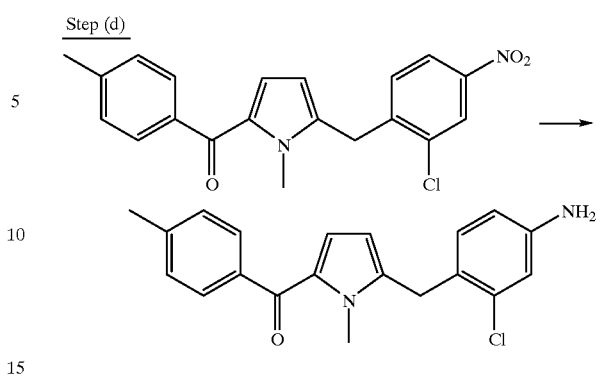

3-Chloro-4-{5-(4-methylbenzoyl)-1-methyl-1H-pyrrol-2-ylmethyl}nitrobenzene (14.38 g, 39.0 mmol) [prepared as in Example 4, Step (c)] was dissolved in ethanol (300 ml) and an aqueous solution of ammonium chloride (14.0 g in 150 ml) and iron powder (14.0 g) were added to the solution. The reaction mixture was refluxed for 30 min, then cooled to room temperature and filtered. The filtrate was concentrated, diluted with water, and extracted with ether and methylene chloride. The organic layer were combined, washed with brine and dried over sodium sulfate. Evaporation gave 3-chloro-4-{5-(4-methylbenzoyl)-1-methyl-1H-pyrrol-2-ylmethyl}aniline (12.09 g, 92%) as a yellow solid.

Example 5

Synthesis of {2-[5-(4-methylbenzoyl)-1-methyl-1H-pyrrol-2-ylmethyl]pyridin-5-yl}amine Step (a)

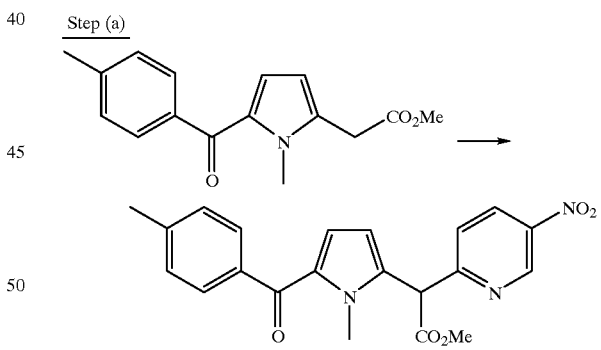

A solution of tolmetin methyl ester (30.0 g, 0.11 mol) and 2-chloro-5-nitropyridine (21.9 g, 0.138 mol) in DMF (350 ml) was cooled to 4° C. and sodium hydride powder (5.87 g, 0.23 mol) was added in portions. The reaction was stirred for 1.5 h and then poured into a cold aqueous solution of potassium bisulfate (31.0 g in 1500 ml water). The resulting orange precipitate was filtered, washed with water, dried under vacuum, and then stirred with ethyl acetate (500 ml). Filtration gave methyl 2-[(5-(4-methylbenzoyl)-1-methylpyrrol-2-yl]-2-(5-nitropyridin-2-yl)-acetate (23 g) as an solid, mp 162.5–163.8° C.

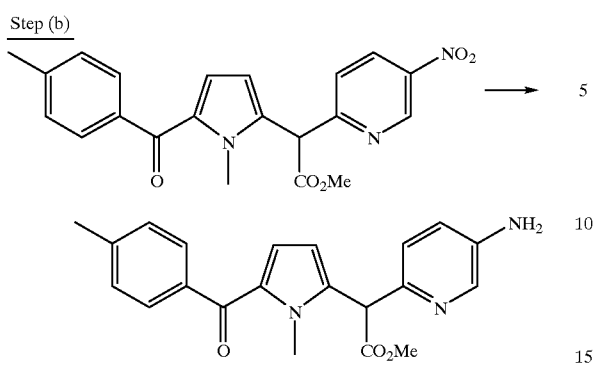

Methyl 2-[(5-(4-methylbenzoyl)-1-methylpyrrol-2-yl]-2-(5-nitropyridin-2-yl)acetate (34.0 g, 86.4 mmol) [prepared as described in Example 5, Step (a)] was dissolved in a mixture of ethanol/THF (600 ml/200 ml) and subjected to catalytic hydrogenation over $PtO_2$ (0.7 g) in a Parr shaker apparatus at 30 psi for 4 h. The reaction mixture was filtered through Celite® and the filtrate was concentrated to dryness. Purification by flash chromatography (hexane-ethyl acetate) gave methyl 2-[(5-(4-methylbenzoyl)-1-methyl-pyrrol-2-yl]-2-(5-aminopyridin-2-yl)-acetate (22.0 g, 70%) as a dark orange gum.

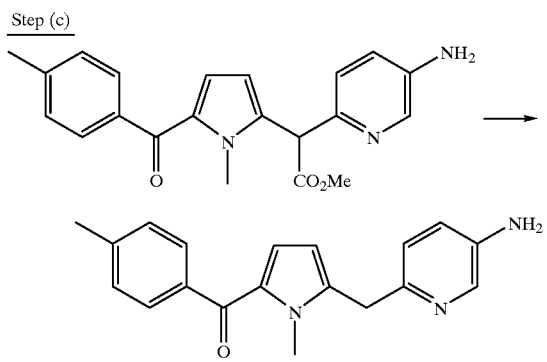

To a solution of methyl 2-[(5-(4-methylbenzoyl)-1-methylpyrrol-2-yl]-2-(5-amino-pyridin-2-yl)acetate (22.0 g, 60.5 mmol) [prepared as in Example 5, Step (b)] in methanol (400 ml) was added an aqueous solution of sodium hydroxide (5.8 g, 145.0 mmol) in 60 ml water. The dark brown reaction mixture was stirred overnight under argon, then acidified with 3 N HCl to pH 2.5 and stirred an additional 6 h. The reaction mixture was then neutralized with a saturated solution of sodium bicarbonate to pH 7.5. The resulting brown precipitate was filtered and purified by flash chromatography (hexane-ethyl acetate) to yield a solid. Recrystallization from hexane-ethyl acetate gave {2-[5-(4-methylbenzoyl)-1-methyl-1H-pyrrol-2-ylmethyl]-pyridin-5-yl}amine (10.2 g, 55%) as a light brown solid, mp 104–106.6° C.

Example 6

Synthesis of 4-[5-(2,4-Dimethylbenzoyl)-1-methylpyrrol-2-ylmethyl)aniline

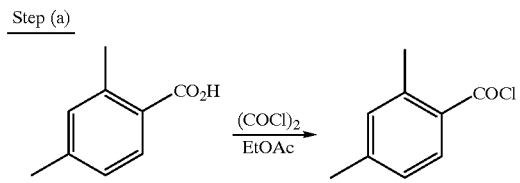

To a suspension of 2,4-dimethylbenzoic acid (10 g, 66.59 mmol) in ethyl acetate (100 ml) was added oxalyl chloride (5.81 ml, 66.59 mmol), and the mixture was slowly heated to 40° C. After 1.5 h, the solvents were removed in vacuo, and the product 2,4-dimethylbenzoyl chloride was used in the next step without purification.

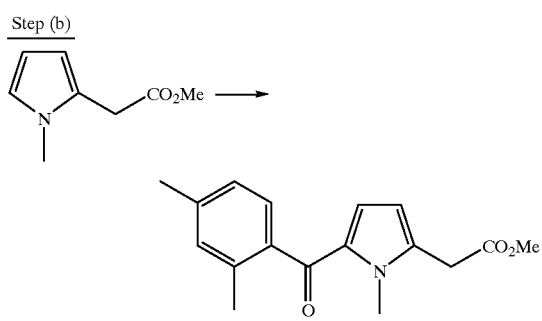

To a solution of 2,4-dimethylbenzoyl chloride (66.59 mmol) [prepared as described in Example 6, Step (a)] in cumene (150 ml) was added methyl 1-methylpyrrole-2-acetate (8 ml, 55.56 mmol) and lithium carbonate (6.16 g, 83.34 mmol), and the reaction mixture was heated to reflux. After 1.5 h, the reaction mixture was cooled to ambient temperature and the solvent was removed in vacuo. Purification by column chromatography (ethyl acetate-hexanes) gave methyl 2-[5-(2,4-dimethylbenzoyl)-1-methylpyrrole-2-acetate (4.03 g, 25%), as a waxy solid.

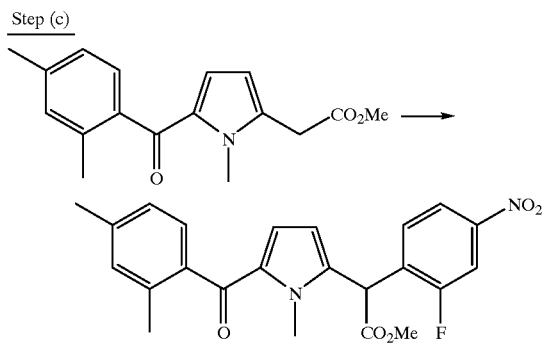

Methyl 2-[5-(2,4-dimethylbenzoyl)-1-methylpyrrole-2-acetate (2.75 g, 9.64 mmol) [prepared as described in Example 6, Step (b)] and 3,4-difluoronitrobenzene (1.28 ml, 11.56 mmol) were dissolved in anhydrous DMF (15 ml) and NaH (486 mg, 20.24 mmol) was added in portions at 0° C. The reaction mixture was stirred at 0° C. for 2 h, then quenched with 1N $NaHSO_4$, and partitioned between ether and 1N NaHSO$_4$. The organic layer was separated, dried over magnesium sulfate, and concentrated to dryness. Purification by column chromatography (ethyl acetate/hexane) gave methyl 2-[5-(2,4-dimethylbenzoyl)-1-methyl-pyrrol-2-yl)-2-(2-fluoro-4-nitrophenyl)acetate (3.56 g, 87%) as a pale yellow oil.

Step (d)

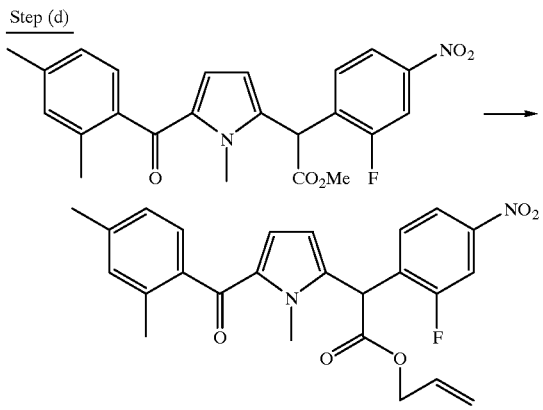

To a solution of methyl 2-[5-(2,4-dimethylbenzoyl)-1-methylpyrrol-2-yl)-2-(2-fluoro-4-nitrophenyl)acetate (3.51 g, 8.27 mmol) [prepared as described in Example 6, Step(c)] in 75 ml allyl alcohol was added titanium tetraisopropoxide (0.244 ml, 0.827 mmol), and the reaction mixture was heated to reflux. After 36 h, the reaction mixture was cooled to room temperature, and partitioned between ether and water. The organic layer was separated, dried over magnesium sulfate, and concentrated to dryness to give allyl 2-[5-(2,4-dimethylbenzoyl)-1-methylpyrrol-2-yl)-2-(2-fluoro-4-nitrophenyl)-acetate (3.60 g, 97%) as a pale yellow oil.

Step (e)

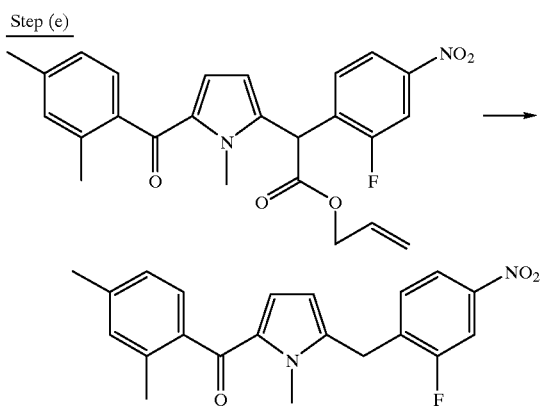

To a solution of allyl 2-[5-(2,4-dimethylbenzoyl)-1-methylpyrrol-2-yl)-2-(2-fluoro-4-nitrophenyl)acetate (3.6 g, 7.99 mmol) [prepared as described in Example 6, Step (d)] in anhydrous THF (40 ml) was added morpholine (6.99 ml, 79.90 mmol) and tetrakis-(triphenylphosphine) palladium (9 mg, 0.008 mmol)). After 1.5 h, the solvent was evaporated and the residue was partitioned between ether and 1N NaHSO$_4$. The organic layer was separated, dried over magnesium sulfate, and concentrated to dryness. Purification by column chromatography (ethyl acetate/hexane) gave 4-[5-(2,4-dimethylbenzoyl)-1-methyl-pyrrol-2-yl-methyl)nitrobenzene (2.73 g, 93%) as a pale yellow oil.

Step (f)

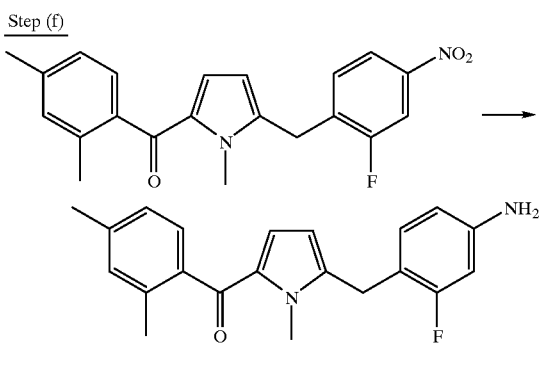

4-[5-(2,4-Dimethylbenzoyl)-1-methylpyrrol-2-ylmethyl) nitrobenzene (923 mg, 2.52 mmol) [prepared as described in Example 6, Step(e)], was dissolved in ethyl acetate (10 ml). 10% Pd/C (92 mg) was added, and the reaction mixture was vigorously stirred under hydrogen atmosphere at ambient temperature and atmospheric pressure for 2 h. The mixture was filtered through Celite®, and the filtrate was evaporated to dryness to give 4-[5-(2,4-dimethylbenzoyl)-1-methylpyrrol-2-yl-methyl)aniline (718 mg, 85%) as pale yellow crystals, mp 107.6–108.5° C.

Example 7

Synthesis of 4-{5-(2,4-dimethylbenzoyl)-1-methyl-1H-pyrrol-2-ylmethyl}aniline

Step (a)

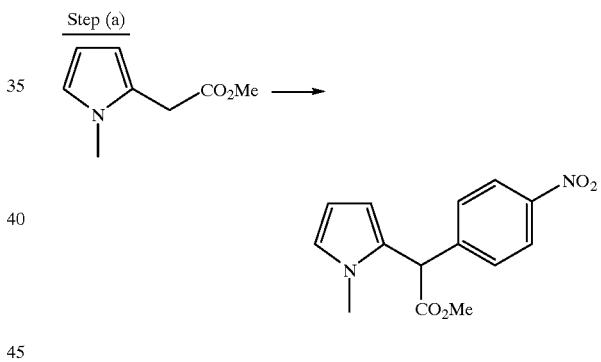

Methyl 1-methylpyrrole-2-acetate (5.0 g, 32.0 mmol) and 4-chloronitrobenzene (10.3 g, 65.0 mmol) were dissolved in DMF (30 ml) and the mixture was cooled in an ice bath under argon. Sodium hydride, 50% in mineral oil, (3.1 g, 64.0 mmol) was added in portions. After stirring for 1 h at room temperature the reaction mixture was poured into 1 M HCl/ice and the product was extracted into ethyl acetate. The organic extracts were washed with water, dried over sodium sulfate, and concentrated to dryness. Purification on a Florisil® column (methylene chloride) gave methyl 2-(1-methylpyrrol-2-yl)-2-(4-nitrophenyl)acetate (4.13 g, 46%) as a solid.

Step (b)

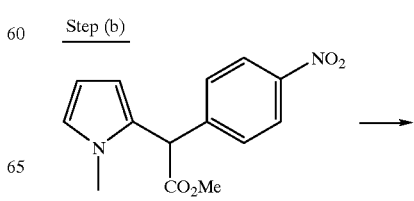

51
-continued

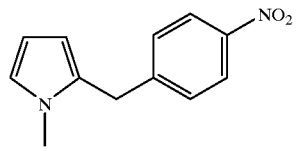

Methyl 2-(1-methylpyrrol-2-yl)-2-(4-nitrophenyl)acetate (3.8 g, 14.0 mmol) [prepared as in Example 7, Step (a)] was dissolved in a 1:1 mixture of MeOH-THF (100 ml) and cooled in an ice bath under argon. A solution of 0.4 M lithium hydroxide (69 ml) was added and the reaction mixture was stirred at room temperature. After 2 h, the reaction mixture was poured into 1 M HCl/ice and extracted with ethyl acetate. The organic layer was washed with water, dried over sodium sulfate and concentrated under reduced pressure. The solid residue was redissolved in DMF (40 ml) and heated at reflux. After 20 min the reaction mixture was poured into ice/water and extracted with ethyl acetate. The organic layer was washed with water, dried over sodium sulfate and concentrated to dryness. Purification on a Florisil® column (hexane-ethyl acetate, 9:1) gave 4-(1-methylpyrrol-2-yl-methyl)nitrobenzene (2.53 g, 82%) as a solid.

Step (c)

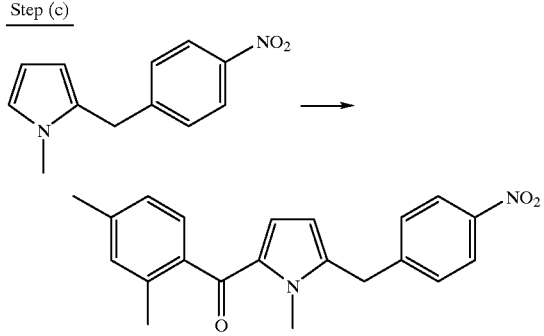

4-(1-Methylpyrrol-2-ylmethyl)nitrobenzene (1.2 g, 5.5 mmol) [prepared as in Example 7, Step (b)], 2,4-dimethylbenzoyl chloride (1.6 g, 9.5 mmol), and triethylamine (1.3 ml, 9.3 mmol) were dissolved in xylenes (50 ml), and the reaction mixture was heated at reflux under argon. After 48 h, the reaction mixture was passed through a Florisil® column (hexane followed by hexane-ethyl acetate, 95:5) to give 4-{5-(2,4-dimethylbenzoyl)-1-methyl-1H-pyrrol-2-yl-methyl}nitrobenzene (0.81 g, 42%) as a solid.

Step (d)

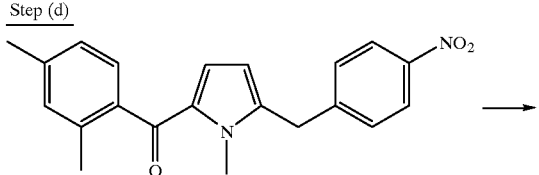

52
-continued

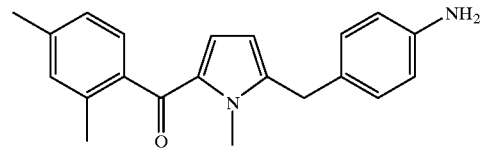

A mixture of 4-{5-(2,4-dimethylbenzoyl)-1-methyl-1H-pyrrol-2-ylmethyl}nitrobenzene (0.81 g, 2.3 mmol), [prepared as in Example 7, Step (c)], nickel boride (1.6 g), 1M HCl (30 ml), and methanol (30 ml) was refluxed for 30 min. The reaction mixture was filtered through a pad of Celite® and the filter cake was washed with ethyl acetate. The filtrate was cooled, made basic with concentrated ammonium hydroxide, and extracted with ethyl acetate. The organic layer was washed with brine, dried over sodium sulfate and concentrated to give 4-{5-(2,4-dimethylbenzoyl)-1-methyl-1H-pyrrol-2-ylmethyl}aniline (760 mg, 100%) as an oil.

Example 8

Synthesis of 3-{5-(4-methylbenzoyl)-1-methyl-1H-pyrrol-2-ylmethyl}aniline

Step (a)

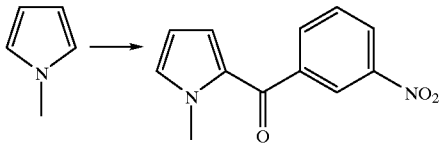

A solution of 1-methylpyrrole (10.0 g, 123.0 mmol), 3-nitrobenzoyl chloride (68.47 g, 369 mmol), and triethylamine (17.14 ml, 123 mmol) in xylenes (150 ml) was refluxed for 40 h. Purification of the reaction mixture on a Florisil® column (hexane-acetone, 85:15) gave 2-(3-nitrobenzoyl)-1-methylpyrrole (13.0 g, 46%) as a solid.

Step (b)

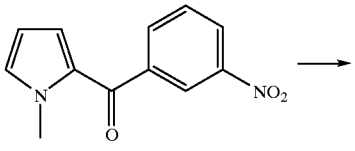

A mixture of 2-(3-nitrobenzoyl)-1-methylpyrrole (5.0 g, 21.7 mmol) [prepared as in Example 8, Step (a)], zinc iodide (10.38 g, 32.5 mmol), sodium cyanoborohydride (10.22 g, 162.7 mmol), and 1,2-dichloroethane (300 ml) was refluxed for 16 h. The reaction mixture was cooled to room temperature, filtered through Celite®, and then concentrated to dryness. Purification of the residue on a Florisil® column (hexane-acetone, 98:1) gave 3-(1-methylpyrrol-2-ylmethyl) nitrobenzene (3.55 g, 75%) as a solid.

Step (c)

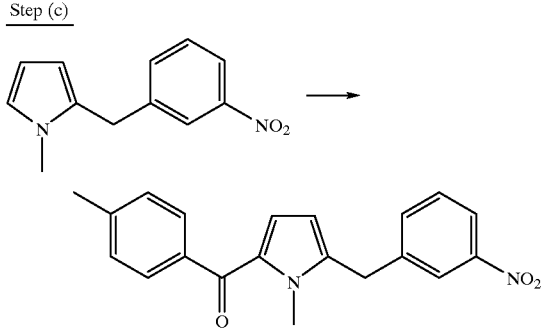

3-(1-Methylpyrrol-2-ylmethyl)nitrobenzene (2.0 g, 9.2 mmol) [prepared as in Example 8, Step (b)], 4-methylbenzoyl chloride (2.84 g, 18.4 mmol), and triethylamine (2.0 ml, 14.3 mmol) were dissolved in xylenes (80 ml) and the reaction mixture was refluxed for 36 h. Purification on a Florisil column (hexane-ethyl acetate, 95:5) gave 3-{5-(4-methyl-benzoyl)-1-methyl-1H-pyrrol-2-ylmethyl}nitrobenzene (0.86 g, 28%) as a solid.

Step (d)

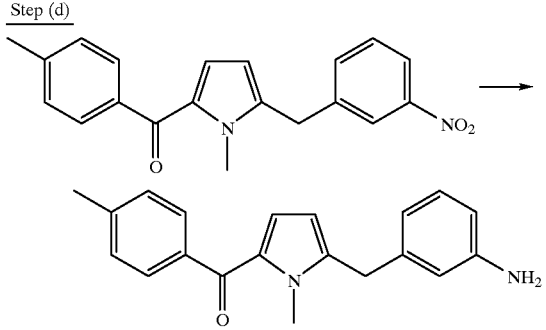

A mixture of 3-{5-(4-methylbenzoyl)-1-methyl-1H-pyrrol-2-ylmethyl}-nitrobenzene (0.86 g, 2.6 mmol) [prepared as in Example 8, Step (c)], nickel boride (1.0 g), 10% HCl (13 ml), and methanol (35 ml) was heated at 65° C. for 40 min. The reaction mixture was cooled to room temperature, made basic with concentrated ammonium hydroxide, and filtered through Celite®. The product was extracted into ethyl acetate, and the organic extracts were washed with water and brine, and dried over sodium sulfate. Evaporation of the organics gave 3-{5-(4-methylbenzoyl)-1-methyl-1H-pyrrol-2-yl-methyl}aniline (0.73 g, 99%) as a solid.

Example 9

Synthesis of 3,5-Difluoro-4-{5-(4-chlorobenzoyl)-1,4-dimethyl-1H-pyrrol-2-ylmethyl}aniline Step (a)

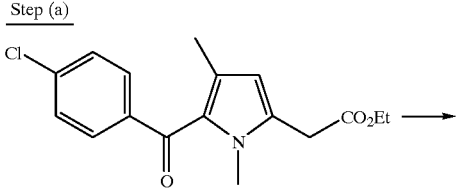

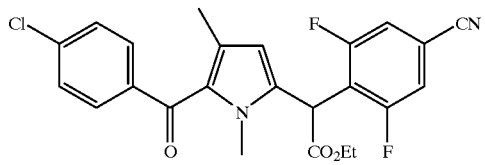

The ethyl ester of zomepirac (4.66 g, 15.2 mmol) and 3,4,5-trifluorobenzonitrile (3.23 g, 20.6 mmol) were dissolved in DMF (75 ml) and NaH (60% in mineral oil, 1.28 g, 32.0 mmol) was added in portions under an argon atmosphere. The reaction mixture was heated at 60° C. for 2.5 h, then cooled to room temperature and added slowly to a mixture of ice/water (600 ml) containing 6N HCl (7.5 ml). The product was filtered and dried under vacuum. Recrystallization from ethyl acetate-hexane gave ethyl 2-[5-(4-chlorobenzoyl)-1,4-dimethyl-pyrrol-2-yl]-2-(2,6-difluoro-4-cyanophenyl)acetate (5.67 g, 84% yield) as yellow crystals, mp 155–155.5° C.

Step (b)

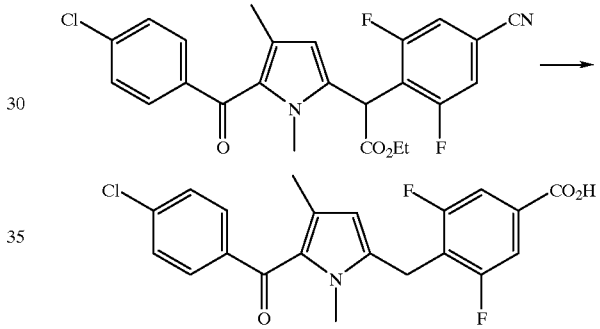

To a slurry of ethyl 2-[5-(4-chlorobenzoyl)-1,4-dimethylpyrrol-2-yl]-2-(2,6-difluoro-4-cyanophenyl)acetate (0.05 g, 0.11 mmol) [prepared as described in Example 9, Step (a)] in methoxyethanol (4 ml) was added an aqueous solution of lithium hydroxide monohydrate (0.02 g in 0.5 ml H₂O), and the reaction mixture was heated at reflux under an argon atmosphere. After 24 hr, the reaction mixture was cooled to room temperature and poured into a mixture of ice/water (40 ml) containing 1N HCl (1 ml). The solid was filtered to give crude {4-[5-(4-chlorobenzoyl)-1,4-dimethyl-1H-pyrrol-2-ylmethyl]]benzoic acid (0.037 g) as a tan solid. Flash chromatography on a silica gel column (0.5% acetic acid-30% acetone:hexane), followed by recrystallization from methanol-acetone gave pure {4-[5-(4-chloro-benzoyl)-1,4-dimethyl-1H-pyrrol-2-ylmethyl]benzoic acid (0.032 g, 70.2% yield) as a white solid, mp 245–246.8° C.

Step (c)

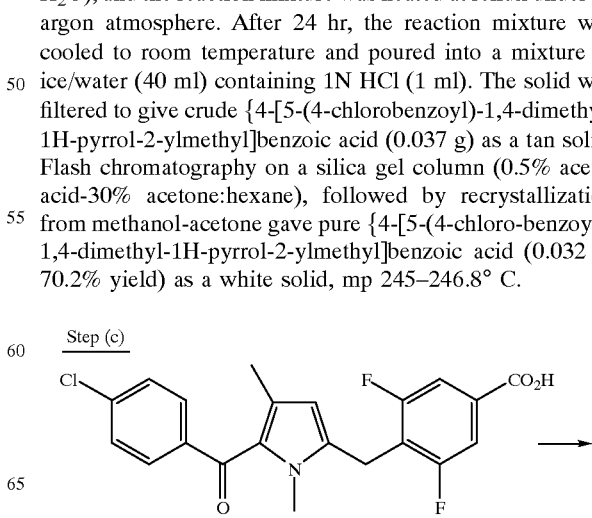

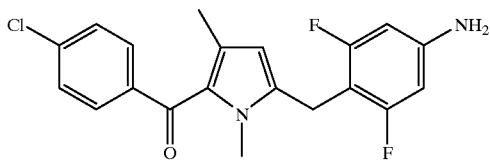

Phosphoryl azide (1.0 ml, 4.61 mmol) was added to a mixture of {4-[5-(4-chloro-benzoyl)-1,4-dimethyl-1H-pyrrol-2-ylmethyl]benzoic acid (1.49 g, 3.69 mmol) [prepared as described in Example 9, Step (b)], and triethylamine (0.77 ml, 5.54 mmol) in toluene at 0° C. under a nitrogen atmosphere. After stirring at room temperature for 10 min, the reaction mixture was heated to 100° C. over the course of 1 hr. After heating at 100° C. for 1 h, the reaction mixture was cooled to room temperature and trimethsilylethanol (1.06 ml, 7.38 mmol) was added. The reaction mixture was reheated and maintained at 50° C. for 1 h under a nitrogen atmosphere, and then the solvent was removed by evaporation under reduced pressure. The resulting yellow oil was redissolved in THF (100 ml) and tetrabutylammonium fluoride (10 ml, 1M soln. in THF) was added. After heating the reaction mixture at reflux for 3 h the solvent was removed in vacuo, and the residue was partitioned between ethyl acetate and water. The organic extracts were washed with water, dried over magnesium sulfate, and evaporated to give a yellow oil. Purification by chromatography on a silica gel column (25% ethyl acetate:hexane), followed by recrystallization from acetone-hexane gave 3,5-difluoro-4-{5-(4-chlorobenzoyl)-1,4-dimethyl-1H-pyrrol-2-ylmethyl}aniline (0.64 g, 64.4% yield) as white crystals, mp 208.2–210° C.

Example 10

Synthesis of 4-{5-(4-chlorobenzoyl)-1,4-dimethyl-1H-pyrrol-2-ylmethyl}phenol

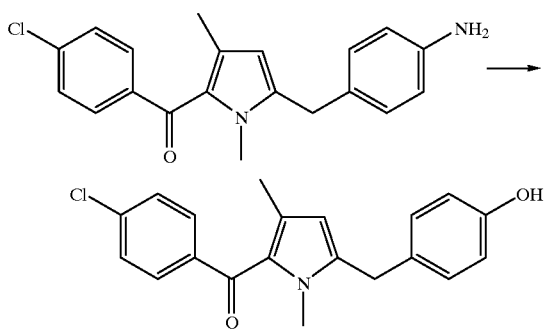

4-{5-(4-Chlorobenzoyl)-1,4-dimethyl-1H-pyrrol-2-ylmethyl}aniline (1.36 g, 4.0 mmol) [prepared by the method described in Example 1, but substituting zomepirac methyl ester and 4-fluoronitrobenzene for ethyl 5-benzoyl-1,4-dimethylpyrrole-2-acetate and 3,4-difluoronitrobenzene respectively, in Step (b)], was dissolved in acetic acid (20 ml), and a solution of 1N sulfuric acid in acetic acid (4.4 ml), followed by acetone (12.5 ml) was added. The reaction mixture was cooled to 6° C. and isoamyl nitrite (0.65 ml, 4.8 mmol) was added. After 1.5 h, the mixture was poured into ether and stored at 2° C. for 6 h. The purple precipitate was filtered, washed with ether and then suspended in acetone (50 ml). After adding sulfuric acid (20 ml, 0.1N), the reaction mixture was stirred at 60° C. for 3 h and then diluted with ethyl acetate and water. The organic layer was separated and washed with water, and dried over sodium sulfate. The solvent was removed in vacuo to give a deep red residue (0.8 g). Purification by flash chromatography (hexane-ether, 6:4), followed by recrystallization from hexane-acetone gave 4-{5-(4-chlorobenzoyl)-1,4-dimethyl-1H-pyrrol-2-ylmethyl}phenol (213 mg, 16%) as a solid, mp 183.4–185.1° C.

Example 11

Synthesis of N-{2-[5-(4-Chlorobenzoyl)-1,4-dimethyl-1H-pyrrol-2-yl-methyl]pyridin-5-yl}acetamide

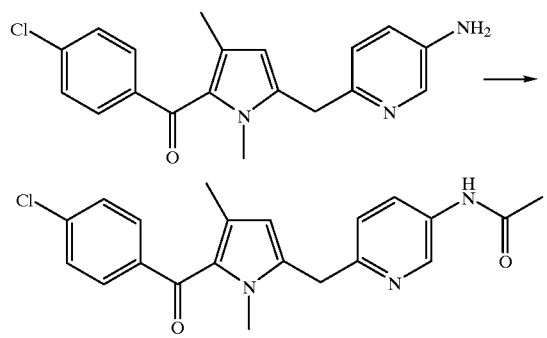

A solution of N-{2-[5-(4-chlorobenzoyl)-1,4-dimethyl-1H-pyrrol-2-ylmethyl]pyridin-5-yl}amine (0.3 g, 0.88 mmol) [prepared by the method described in Example 5, but substituting zomepirac methyl ester for tolmetin methyl ester in Step (a)] and acetic anhydride (0.375 ml, 3.96 mmol) in THF was stirred at 60° C. for 4 h. The solvents were removed under reduced pressure and the residue was crystallized from hexane-chloroform to give N-{2-[5-(4-chlorobenzoyl)-1,4-dimethyl-1H-pyrrol-2-ylmethyl]pyridin-5-yl}-acetamide (295 mg, 88%) as a solid, mp 194–195° C.

Example 12

Synthesis of N-{2-[5-(4-chlorobenzoyl)-1,4-dimethyl-1H-pyrrol-2-yl-methyl]pyridin-5-yl}formamide

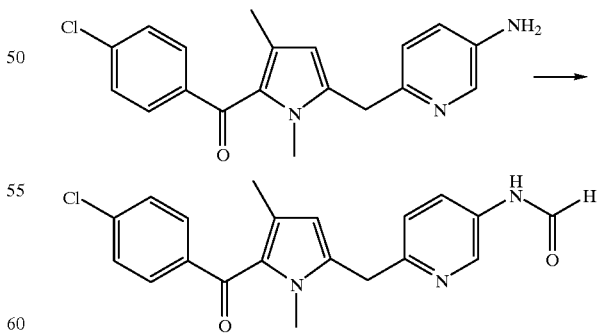

The mixed anhydride of formic and acetic acid was prepared by adding formic acid (1 ml, 98%) dropwise to acetic anhydride (2 ml) and heating the mixture at 55° C. for 2.5 h. This reagent (2.2 ml) was then added to a solution of N-{2-[5-(4-chlorobenzoyl)-1,4-di-methyl-1H-pyrrol-2- methyl]-pyridin-5-yl}amine (0.3 g, 0.88 mmol) in THF (7 ml), and the reaction mixture was heated overnight at 60° C. The solvents were removed in vacuo and the residue was crystallized from chloroform-hexane to give N-{2-[5-(4-chloro-benzoyl)-1,4-dimethyl-1H-pyrrol-2-ylmethyl] pyridin-5-yl}formamide (175 mg, 54%) as a solid, mp 166.6–167.7° C.

1.46 mmol) were dissolved in pyridine (6.6 ml), and the mixture was stirred at room temperature for 96 h. The solvents were removed in vacuo and the residue was crystallized from chloroform-hexane mixture to give 1-{2-[5-(4-chlorobenzoyl)-1,4-dimethyl-1H-pyrrol-2-ylmethyl] pyridin-5-yl}-3,3-dimethylurea (0.31 g, 57%) as a solid, mp 227.2–230.0° C.

Example 13

Synthesis of 1-{4-[5-(4-Chlorobenzoyl)-1,4-dimethyl-1H-pyrrol-2-yl-methyl]phenyl}-3-(2-hydroxyethyl)urea

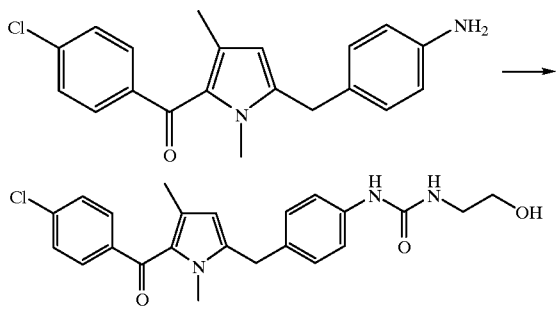

Example 15

Synthesis of 1-{2-[5-(4-Chlorobenzoyl)-1,4-dimethyl-1H-pyrrol-2-yl-methyl]pyridin-5-yl}-3-methylurea

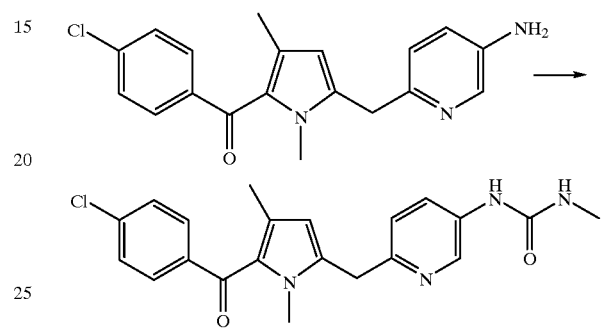

4-{5-(4-Chlorobenzoyl)-1,4-dimethyl-1H-pyrrol-2-ylmethyl}aniline (0.33 g, 0.98 mmol) and 1,1'-carbonyldiimidazole (0.4 g, 2.46 mmol) were dissolved in DMF, and the reaction mixture was stirred at room temperature for 1 h. Ethanolamine (0.3 ml, 4.91 mmol) was added and after 1.5 h the mixture was diluted with water. The product was extracted into ethyl acetate, and the organic layer was dried over $MgSO_4$ and then concentrated under vacuum. Purification by flash chromatography (ethyl acetate), followed by recrystallization from hexane-chloroform gave 1-{4-[5-(4-chlorobenzoyl)-1,4-dimethyl-1H-pyrrol-2-ylmethyl]phenyl}-3-(2-hydroxyethyl)urea (239 mg, 57%) as a solid, mp 209.6–210.2° C.

{2-{5-(4-Chlorobenzoyl)-1,4-dimethyl-1H-pyrrol-2-ylmethyl]pyridin-5-yl}amine (0.3 g, 0.88 mmol) was dissolved in THF (4 ml), and the solution was cooled to 0° C. Methyl isocyanate (0.062 ml, 1.06 mmol) was added and the reaction mixture was stirred overnight at ambient temperature. Additional methyl isocyanate (0.062 ml) was added and the mixture was stirred for an additional 24 h. The reaction mixture was concentrated under vacuum and the residue was crystallized from hexane-chloroform to give 1-{2-[5-(4-chlorobenzoyl)-1,4-di-methyl-1H-pyrrol-2-ylmethyl] pyridin-5-yl}-3-methylurea (240 mg, 69%), mp 234.0–235.5° C.

Example 14

Synthesis of 1-{2-[5-(4-chlorobenzoyl)-1,4-dimethyl-1H-pyrrol-2-yl-methyl]pyridin-5-yl}-3,3-dimethylurea

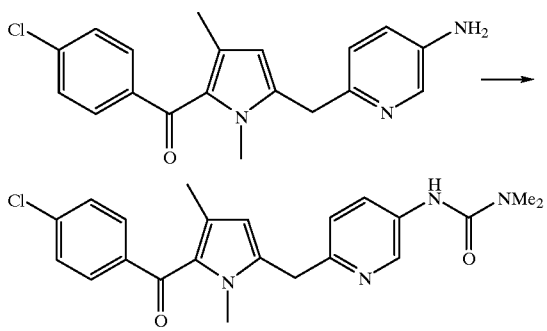

Example 16

Synthesis of 1-{2-[5-(4-chlorobenzoyl)-1,4-dimethyl-1H-pyrrol-2-yl-methyl]pyridin-5-yl}-3-methyl-2-thiourea

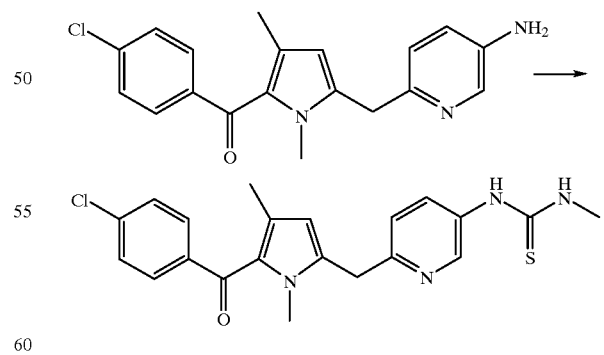

{2-[5-(4-Chlorobenzoyl)-1,4-dimethyl-1H-pyrrol-2-ylmethyl]pyridin-5-yl}amine [prepared by the method described in Example 5, but substituting the methyl ester of zomepirac for the methyl ester of tolmetin in Step (a)] (0.45 g, 1.32 mmol) and dimethylcarbamoyl chloride (0.13 ml, N-{2-[5-(4-Chlorobenzoyl)-1,4-dimethyl-1H-pyrrol-2-ylmethyl]pyridin-5-yl}amine (0.3 g, 0.88 mmol) and methylisothiocyanate (0.3 ml, 4.4 mmol) were dissolved in THF and the reaction mixture was stirred at 60° C. overnight. The mixture was diluted with ethyl acetate and washed with 1N HCl, 10% sodium bicarbonate, water, and brine. The solvents were removed in vacuo and the crude product was purified by flash chromatography (ethyl acetate-methanol, 97:3) to give 1-{2-[5-(4-chlorobenzoyl)-1,4-dimethyl-1H-pyrrol-2-ylmethyl]pyridin-5-yl}-3-methyl-2-thiourea (265 mg, 73%) as a solid, mp 135° C.

Example 17

Synthesis of N-{3-Fluoro-4-[5-benzoyl-1,4-dimethyl-1H-pyrrol-2-yl-methyl]phenyl}methanesulfonamide

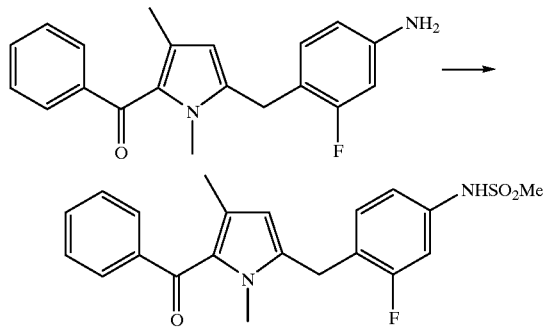

3-Fluoro-4-[5-benzoyl-1,4-dimethyl-1H-pyrrol-2-ylmethyl]aniline (1.0 g, 3.1 mmol) [prepared as described in Example 1] was dissolved in pyridine (10 ml) and the solution was cooled to −5° C. Methanesulfonyl chloride (0.39 g, 3.4 mmol) was added and after 1 h the reaction mixture was poured into 1M HCl/ice/water and extracted with ethyl acetate. The organic layer was washed with water, dried over sodium sulfate and concentrated to dryness. The residue was crystallized from methylene chloride-methanol to give N-{3-fluoro-4-[5-benzoyl-1,4-dimethyl-1H-pyrrol-2-ylmethyl]phenyl}-methanesulfonamide (775 mg, 62%) as a solid, mp 165–167° C.

Proceeding as described in Example 17, but substituting 3-Cyano-4-[5-(4-chloro-benzoyl)-1,4-dimethyl-1H-pyrrol-2-ylmethyl]aniline [prepared by the method described in Example 4, but substituting the sodium salt of zomepirac for the sodium salt of tolmetin in Step (a) and 3-cyano-4-chloronitrobenzene for 3,4-dichloronitrobenzene in Step (b)], for 3-fluoro-4-[5-benzoyl-1,4-dimethyl-1H-pyrrol-2-ylmethyl]aniline gave N-{3-cyano-4-[5-(4-chlorobenzoyl)-1,4-dimethyl-pyrrol-2-ylmethyl]phenyl}methanesulfonamide.

Proceeding as described in Example 17, but substituting {2-[5-(4-chlorobenzoyl)-1,4-dimethyl-1H-pyrrol-2-ylmethyl]pyridin-5-yl}amine, [prepared by the method described in Example 5, but substituting the zomepirac methyl ester for the tolmetin methyl ester in Step (a)], for 3-fluoro-4-[5-benzoyl-1,4-dimethyl-1H-pyrrol-2-ylmethyl]aniline gave N-{2-[5-(4-chlorobenzoyl)-1,4-dimethyl-1H-pyrrol-2-ylmethyl]pyridin-5-yl}methane-sulfonamide.

Proceeding as described in Example 17, but substituting {2-[5-(4-methylbenzoyl)-1-methyl-1H-pyrrol-2-ylmethyl]pyridin-5-yl}amine, [prepared by the method described in Example 5], for 3-Fluoro-4-[5-benzoyl-1,4-dimethyl-1H-pyrrol-2-ylmethyl]aniline gave N-2-[5-(4-methylbenzoyl)-1-methyl-1H-pyrrol-2-ylmethyl]pyridin-5-yl}-methanesulfonamide.

Proceeding as described in Example 17, but substituting 3-fluoro-4-[5-(2-methoxy-benzoyl)-1-methyl-1H-pyrrol-2-ylmethyl]aniline [prepared by the method described in Example 1, but substituting 2-methoxybenzoyl chloride and methyl 1-methylpyrrole-2-acetate for benzoyl chloride and ethyl 1,4-dimethylpyrrole-2-acetate, respectively in Step (a)] for 3-fluoro-4-[5-benzoyl-1,4-dimethyl-1H-pyrrol-2-yl-methyl]aniline gave N-{3-fluoro-4-[5-(2-methoxybenzoyl)-1-methyl-1H-pyrrol-2-yl-methyl]phenyl}-methanesulfonamide.

Proceeding as described in Example 17, but substituting {3-chloro-2-[5-(4-methoxy-benzoyl)-1,4-dimethyl-1H-pyrrol-2-ylmethyl]pyridin-5-yl}amine [prepared by the method described in Example 4, but substituting methyl 5-(4-methoxybenzoyl)-1,4-dimethylpyrrole-2-acetate for the sodium salt of tolmetin in step (a) and 2,3-dichloro-4-nitropyridine for 3,4-dichloronitrobenzene in Step (b)], for 3-fluoro-4-[5-benzoyl-1,4-dimethyl-1H-pyrrol-2-ylmethyl]aniline gave N-{3-[5-(4-methoxybenzoyl)-1,4-dimethyl-1H-pyrrol-2-yl-methyl]pyridin-5-yl}methanesulfonamide.

Proceeding as described in Example 17, but substituting {2-[5-(4-methoxybenzoyl)-1-methyl-1H-pyrrol-2-ylmethyl]pyridin-5-yl}amine [prepared by the method described in Example 5, but substituting the methyl ester of tolmetin for methyl 5-(4-methylbenzoyl)-1-methylpyrrole-2-acetate in Step (b)], for 3-fluoro-4-[5-benzoyl-1,4-dimethyl-1H-pyrrol-ylmethyl]aniline gave N-{2-[5-(4-methoxybenzoyl)-1-methyl-1H-pyrrol-2-ylmethyl]-pyridin-5-yl}methanesulfonamide.

Example 18

Synthesis of N-{3-fluoro-4-[5-benzoyl-1-methyl-1H-pyrrol-2-yl-methyl]phenyl}-2-(hydroxy)ethanesulfonamide.

Step (a)

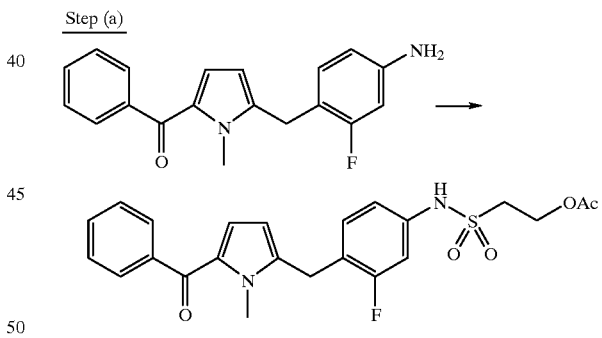

3-Fluoro-4-[5-benzoyl-1-methyl-1H-pyrrol-2-ylmethyl]aniline (0.75 g, 2.43 mmol) [prepared as described in Example 1, but substituting ethyl 1,4-dimethylpyrrole-2-acetate with methyl 1-methylpyrrole-2-acetate in Step (a)], and pyridine (0.39 ml, 4.88 mmol) were dissolved in methylene chloride (8 ml). 2-Acetoxyethanesulfonyl chloride (681 mg, 3.65 mmol) was added to the solution and after 15 min, the reaction mixture was partitioned between ethyl acetate and water. The organic layer was separated, washed with brine, dried over sodium sulfate and concentrated to dryness. Purification of the residue by flash chromatography (hexane-ethyl acetate, 3:2) gave N-{3-fluoro-4-[5-benzoyl-1-methyl-1H-pyrrol-2-ylmethyl]-phenyl}-2-(acetoxy)ethanesulfonamide, (643 mg, 58%) as a solid.

Step (b)

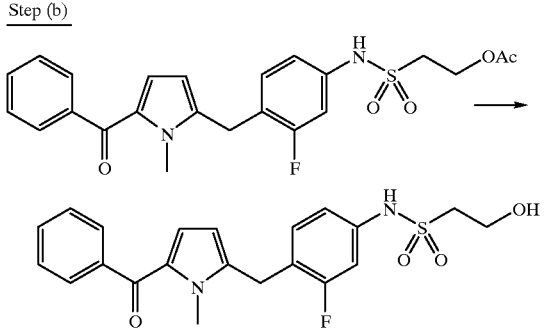

N-{3-Fluoro-4-[5-benzoyl-1-methyl-1H-pyrrol-2-ylmethyl]phenyl}-2-(acetoxy)-ethanesulfonamide (0.415 g, 0.905 mmol) [prepared as in Example 18, Step (a)] was dissolved in methanol (5 ml) and a 2.0 M solution of ammonia in methanol (4.53 ml, 9.05 mmol) was added. The mixture was stirred for 60 h, after which it was concentrated to dryness. Purification of the residue by flash chromatography gave N-{3-fluoro-4-[5-benzoyl-1-methyl-1H-pyrrol-2-ylmethyl]phenyl}-2-(hydroxy)-ethanesulfonamide (282 mg, 75%) as a solid.

Proceeding as described in Example 18, but substituting 3-fluoro-4-[5-(2,4-di-methylbenzoyl)-1-methyl-1H-pyrrol-2-ylmethyl]aniline [prepared by the method described in Example 6], for 3-fluoro-4-[5-benzoyl-1-methyl-1H-pyrrol-2-ylmethyl]aniline gave N-{3-fluoro-4-[5-(2,4-dimethylbenzoyl)-1-methyl-1H-pyrrol-2-ylmethyl]phenyl}-2-(hydroxy)-ethanesulfonamide.

Proceeding as described in Example 18, but substituting 3-fluoro-4-[5-(4-methyl-benzoyl)-1-methyl-1H-pyrrol-2-ylmethyl]aniline [prepared by the method described in Example 1, but substituting the methyl ester of tolmetin for ethyl 5-benzoyl-1,4-di-methylpyrrole-2-acetate in step (b)], for 3-fluoro-4-[5-benzoyl-1-methyl-1H-pyrrol-2-ylmethyl] aniline gave N-{3-fluoro-4-[5-(4-methylbenzoyl)-1-methyl-1H-pyrrol-2-yl-methyl]phenyl}-2-(hydroxy)-ethanesulfonamide.

Proceeding as described in Example 18, but substituting 3-fluoro-4-[5-(4-methoxy-benzoyl)-1,4-dimethyl-1H-pyrrol-2-ylmethyl]aniline [prepared by the method described in Example 1, but substituting 4-methoxybenzoyl chloride for benzoyl chloride in step (a)], for 3-fluoro-4-[5-benzoyl- 1-methyl-1H-pyrrol-2-ylmethyl]aniline gave N-{3-fluoro-4-[5-(4-methoxybenzoyl)-1,4-dimethyl-1H-pyrrol-2-ylmethyl]phenyl}-2-(hydroxy)-ethanesulfonamide.

Example 19

Synthesis of N-{4-[5-(4-Chlorobenzoyl)-1,4-dimethyl-1H-pyrrol-2-yl-methyl]phenyl}ethenesulfonamide

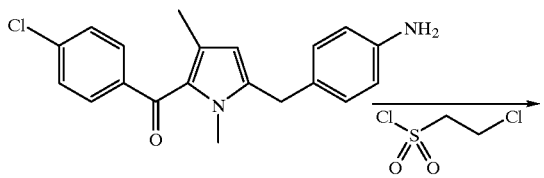

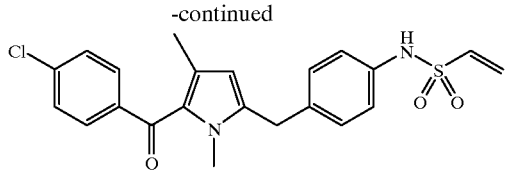

4-[5-(4-Chlorobenzoyl)-1,4-dimethyl-1H-pyrrol-2-ylmethyl]aniline (1.1 g, 3.25 mmol) was dissolved in pyridine (16.5 ml) and 2-chloroethanesulfonyl chloride (1.02 ml, 9.74 mmol) was added to the solution. The mixture was stirred for 1.5 h and then concentrated to dryness. The residue was filtered through a pad of silica gel (ethyl acetate) to give N-{4-[5-(4-chloro-benzoyl)-1,4-dimethyl-1H-pyrrol-2-ylmethyl]phenyl}ethenesulfonamide, (1.29 g, 93%) as a solid.

Example 20

Synthesis of N-4-[5-(4-chlorobenzoyl)-1,4-dimethyl-1H-pyrrol-2-ylmethyl]phenyl}-2-(dimethylamino)ethanesulfonamide hydrochloride

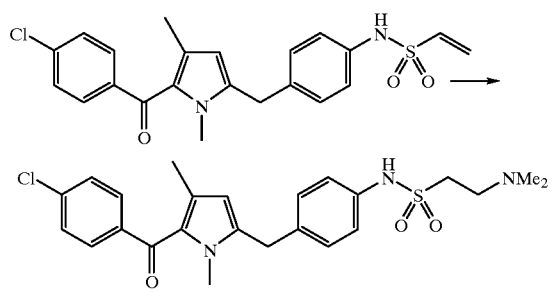

N-{4-[5-(4-Chlorobenzoyl)-1,4-dimethyl-1H-pyrrol-2-ylmethyl]phenyl}-ethenesulfonamide (250 mg, 0.583 mmol) [prepared as in Example 19], was dissolved in DMF (1.1 ml). Triethylamine (0.11 ml, 0.8 mmol), followed by dimethylamine hydrochloride (36 mg, 0.69 mmol), was added and the reaction mixture was stirred for 1 h. A second batch of trimethylamine and dimethyamine hydrochloride was added and the stirring was continued overnight. The reaction mixture was partitioned between ethyl acetate and water, and the organic layer was separated and dried over sodium sulfate. The solvent was removed in vacuo and the crude product was then dissolved in ethyl acetate, after which ethanolic HCl was added to give N-{4-[5-(4-chlorobenzoyl)-1,4-dimethyl-1H-pyrrol-2-ylmethyl]phenyl}-2-(dimethyl-amino)ethanesulfonamide (257 mg, 86%) as the hydrochloride salt.

Example 21

Synthesis of N-{4-[5-(4-aminobenzoyl)-1-methyl-1H-pyrrol-2-yl-methyl]phenyl}methanesulfonamide Step (a)

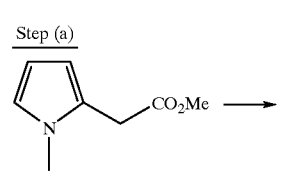

-continued

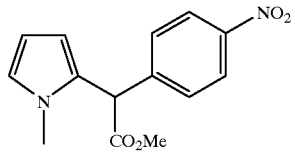

Methyl 1-methylpyrrole-2-acetate (5.32 g, 34.73 mmol) and 4-fluoro-nitrobenzene (4.9 g, 34.73 mmol) were dissolved in dry DMF (100 ml), and the solution was cooled to 0° C. under nitrogen. Sodium hydride powder (1.75 g, 72.93 mmol) was added in portions. After 30 min the reaction mixture was quenched with 1 M HCl and the product was extracted into ether. The organic extracts were washed with water and brine, and dried over magnesium sulfate. The solvent was removed in vacuo to give methyl-2-(1-methylpyrrol-2-yl)-2-(4-nitrophenyl)acetate (9.20 g, 97%) as a red oil.

Step (b)

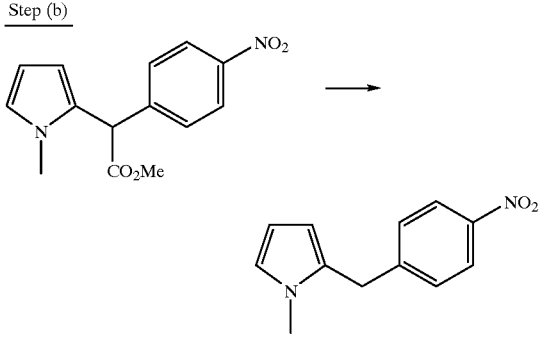

Methyl 2-(1-methylpyrrol-2-yl)-2-(4-nitrophenyl)acetate (9.2 g, 33.54 mmol) [prepared as in Example 21, Step (a)], was dissolved in methanol (100 ml) and an aqueous solution of lithium hydroxide (3.52 g in 50 ml of water) was added. After 1.5 h the reaction mixture was concentrated to dryness in vacuo and the resulting residue was dissolved in water (100 ml). The solution was acidified to pH 1 with 6 M HCl and then extracted with ethyl acetate. The organic extracts were washed with water, and brine, and dried over magnesium sulfate. The solvent was removed in vacuo and the residue was purified by flash chromatography (hexane-ethyl acetate, 9:1) to give 4-(1-methylpyrrol-2-ylmethyl) nitrobenzene (4.8 g, 66%) as a yellow oil.

Step (c)

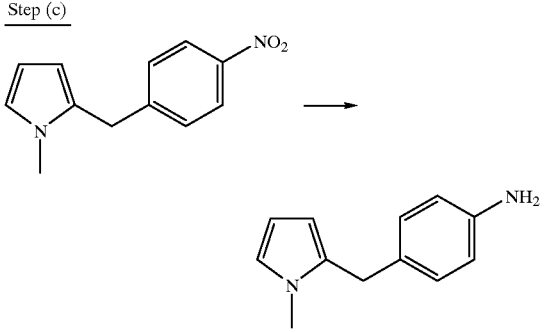

4-(1-Methylpyrrol-2-ylmethyl)nitrobenzene (500 mg, 2.31 mmol) [prepared as described in Example 21, Step (b)], was dissolved in ethyl acetate and subjected to hydrogenation over 5% Pd/C (50 mg) at ambient temperature and atmospheric pressure. After 3 h the mixture was filtered and the filtrate was concentrated to give 4-(1-methylpyrrol-2-yl-methyl)aniline (430 mg, 100%) as a yellow oil.

Step (d)

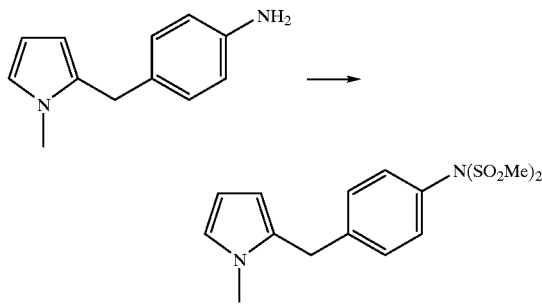

A mixture of 4-(1-methylpyrrol-2-ylmethyl)aniline (3.21 g, 17.23 mmol) [prepared as in Example 21, Step (c)], and triethylamine (8.4 ml, 60.27 mmol) was cooled to 0° C. under nitrogen. Methanesulfonyl chloride (4.2 ml, 54.26 mmol) was added and after for 1.5 h the reaction mixture was diluted with methylene chloride. The organic layer was separated and washed with 1 M aqueous sodium bisulfate, and brine and then dried over magnesium sulfate. Evaporation gave N-{4-(1-methylpyrrol-2-ylmethyl) phenyl}bismethanesulfonamide (6.63 g) as an orange foam which was used in step (e) without further purification.

Step (e)

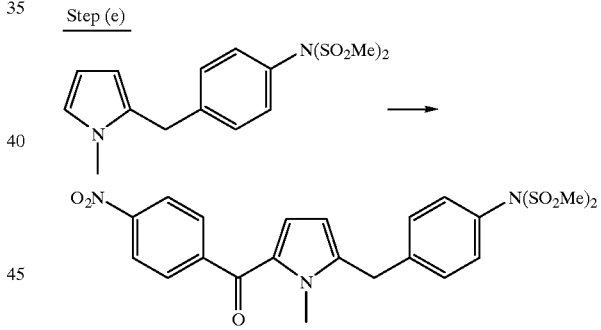

N,N-dimethyl-4-nitrobenzamide (0.65 mg, 3.36 mmol) and phosphorus oxychloride were stirred together until the mixture became homogeneous. A solution of N-{4-(1-methylpyrrol-2-ylmethyl)-phenyl}-bis-methanesulfonamide (1.15 g) [prepared as described in Example 21, Step (d)], in dry dichloroethane (15 ml) was added and the stirring was continued overnight. Sodium bicarbonate (17 ml, 10% solution in water) was added and after 1.5 h the reaction mixture was cooled to room temperature, and diluted with methylene chloride. The organic layer was separated and washed with water and brine, and dried over magnesium sulfate. The solvent was removed in vacuo and the residue was purified by flash chromatography (hexane-ethyl acetate, 3:2) to give N-{4-[5-(4-nitro-benzoyl)-1-methyl-1H-pyrrol-2-ylmethyl]-phenyl}bismethanesulfonamide (0.35 g, 25%) as an oil.

Step (f)

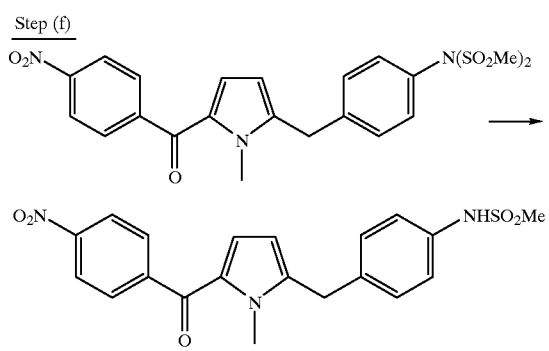

4-{5-[(4-Nitrobenzoyl)-1-methyl-1H-pyrrol-2-ylmethyl]phenyl}bismethanesulfonamide (0.35 g, 0.712 mmol) [prepared as in Example 21, Step (e)], was dissolved in dioxane (4 ml) and an aqueous solution of lithium hydroxide (60 mg, 1.42 mmol in 1 ml of water) was added. After stirring for 60 h the mixture was partitioned between ethyl acetate and a 1 M sodium bisulfate solution. The organic layer was separated, washed with brine, and dried over sodium sulfate. Concentration gave N-{4-[5-(4-nitrobenzoyl)-1-methyl-1H-pyrrol-2-yl-methyl]phenyl}methanesulfonamide (294 mg) as a dark yellow oil which was used in the next step without further purification.

Step (g)

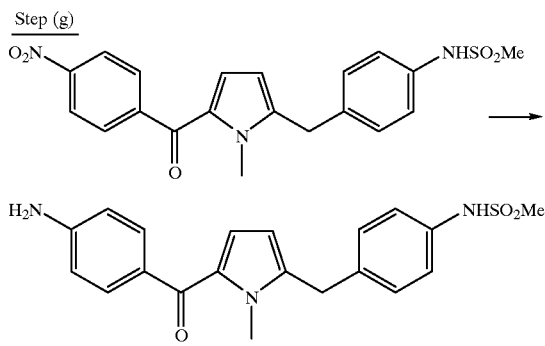

N-{4-[5-[(4-Nitrobenzoyl)-1-methyl-1H-pyrrol-2-ylmethyl]phenyl}methanesulfonamide (294 mg) [prepared as in Example 21, Step (f)], and an aqueous solution of ammonium chloride (0.3 g/2.5 ml water) were dissolved in ethanol (5 ml). Iron powder (0.2 g) was added and the reaction mixture was heated at reflux for 20 min. The mixture was filtered and the filter cake was washed with methylene chloride. The filtrate was diluted with ethyl acetate, washed with water, and brine, and dried over sodium sulfate. The solvent was removed in vacuo and the residue was purified by flash chromatography (hexane-ethyl acetate, 3:2). Recrystallization of the product from hexane-ethyl acetate gave N-{4-[5-(4-aminobenzoyl)-1-methyl-1H-pyrrol-2-ylmethyl]phenyl}methanesulfonamide (175 mg, 64%) as a yellow powder.

Example 22

Synthesis of 1-{3-fluoro-4-[5-benzoyl-1,4-dimethyl-1H-pyrrol-2-yl-methyl]phenyl}-3,3-dimethylsulfamide

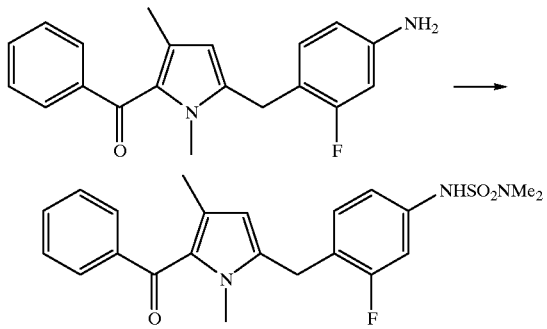

3-Fluoro-4-[5-benzoyl-1,4-dimethyl-1H-pyrrol-2-ylmethyl]aniline (1.0 g, 3.1 mmol) [prepared by the method described in Example 1], and N,N-dimethylsulfamoyl chloride (894 mg, 6.2 mmol) were dissolved in pyridine (10 ml) and stirred at 50° C. for 12 h. The reaction mixture was poured into 1M HCl/ice/water and extracted with ethyl acetate. The organic layer was separated, washed with water, dried over sodium sulfate and concentrated to dryness. The residue was triturated with methanol, filtered and then purified by preparatory thin layer chromatography TLC (hexane-ethyl acetate, 3:2). Crystallization from a chloroform-hexane mixture gave 1-{3-fluoro-4-[5-benzoyl-1,4-dimethyl-1H-pyrrol-2-yl-methyl]phenyl)-3,3-dimethylsulfamide (343 mg, 26%), mp 182–182° C.

Proceeding as described in Example 22, but substituting 4-[5-(4-chlorobenzoyl)-1,4-di-methyl-1H-pyrrol-2-ylmethyl]aniline [prepared by the method described in Example 1, but substituting methyl ester of zomepirac and 4-fluoronitrobenzene for ethyl 5-benzoyl-1,4-di-methylpyrrole-2-acetate and 3,4-difluoronitrobenzene respectively in Step (b)], for 3-fluoro-4-[5-benzoyl-1,4-dimethyl-1H-pyrrol-2-ylmethyl]aniline gave 1-{4-[5-(4-chloro-benzoyl)-1,4-dimethyl-1H-pyrrol-2-ylmethyl]phenyl}-3,3-dimethylsulfamide.

Example 23

Synthesis of 1-3-Fluoro-4-[5-(4-methylbenzoyl)-1-methyl-1H-pyrrol-2-yl-methyl]phenyl}sulfamide

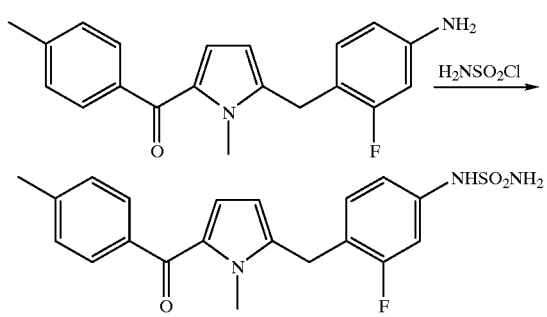

A 1M solution of aminosulfamoyl chloride was prepared by addition of a solution of water (1.44 g, 80.0 mmol) in ethylene glycol dimethyl ether (20 ml) to a solution of chlorosulfonyl isocyanate (7.0 ml, 80.0 mmol) in ethylene glycol dimethyl ether (60 ml) under nitrogen at −45° C. The reaction mixture was allowed to warm to room temperature slowly. This reagent solution (1.0 ml, 1.0 mmol) was added to a solution of 3-fluoro-4-[5-(4-methylbenzoyl)-1-methyl-1H-pyrrol-2-ylmethyl]aniline (322 mg, 1.0 mmol) and triethylamine (0.14 ml, 1.2 mmol) in dry methylene chloride at 5° C. under nitrogen. After 35 min, additional amounts of triethylamine (0.7 ml, 0.6 mmol) and aminosulfamoyl chloride solution (0.5 ml, 0.5 mmol) were added, and the reaction mixture was stirred for an additional 15 min. The reaction mixture was diluted with ethyl acetate and water, and the organic layer was separated, washed with 1M sodium bisulfate and brine, and dried over magnesium sulfate. The solvent was removed in vacuo and the solid residue was triturated with ether to give 1-{3-fluoro-4-[5-(4-methylbenzoyl)-1-methyl-1H-pyrrol-2-ylmethyl]-phenyl}sulfamide (303 mg, 75%) as a tan powder.

Proceeding as described in Example 23, but substituting 3-fluoro-4-[5-(2,4-dimethyl-benzoyl)-1-methyl-1H-pyrrol-2-ylmethyl]aniline [prepared by the method described in Example 6], for 3-fluoro-4-[5-(4-methylbenzoyl)-1-methyl-1H-pyrrol-2-yl-methyl]aniline gave 1-{3-fluoro-4-[5-(2,4-dimethylbenzoyl)-1-methyl-1H-pyrrol-2-yl-methyl]phenyl}-sulfamide.

Proceeding as described in Example 23, but substituting 3-fluoro-4-[5-(4-chloro-benzoyl)-1,4-dimethyl-1H-pyrrol-2-ylmethyl]aniline [prepared by the method described in Example 1, but substituting the methyl ester of zomepirac for ethyl 5-benzoyl-1,4-dimethyl-pyrrole-2-acetate in Step (b)], for 3-fluoro-4-[5-(4-methylbenzoyl)-1-methyl-1H-pyrrol-2-yl-methyl]aniline gave 1-{3-fluoro-4-[5-(4-chlorobenzoyl)-1,4-dimethyl-1H-pyrrol-2-ylmethyl]phenyl}sulfamide.

Proceeding as described in Example 23, but substituting 3-cyano-4-[5-(4-methoxy-benzoyl)-1-methyl-1H-pyrrol-2-ylmethyl]aniline [prepared by the method described in Example 6, but substituting 4-methoxybenzoyl chloride for 2,4-dimethy-lbenzoyl chloride in Step (b) and 3-cyano-4-chloronitrobenzene for 3,4-difluoro-nitrobenzene in Step (c)], for 3-fluoro-4-[5-(4-methylbenzoyl)-1-methyl-1H-pyrrol-2-ylmethyl]aniline gave 1-{3-cyano-4-[5-(4-methoxybenzoyl)-1-methyl-1H-pyrrol-2-ylmethyl]phenyl}sulfamide.

Proceeding as described in Example 23, but substituting {2-[5-(4-methoxybenzoyl)-1-methyl-1H-pyrrol-2-ylmethyl]pyridin-5-yl}amine [prepared by the method described in Example 5, but substituting the methyl ester of tolmetin for methyl 5-(4-methylbenzoyl)-1-methylpyrrole- 2-acetate in Step (b)], for 3-fluoro-4-[5-(4-methylbenzoyl)-1-methyl-1H-pyrrol-2-ylmethyl]aniline gave 1-{2-[5-(4-methoxybenzoyl)-1-methyl-1H-pyrrol-2-yl-methyl]pyridin-5-yl}sulfamide.

Example 24

Synthesis of 1-{4-[5-(4-chlorobenzoyl)-1,4-dimethyl-1H-pyrrol-2-yl-methyl]phenyl}-3-sulfamorpholide

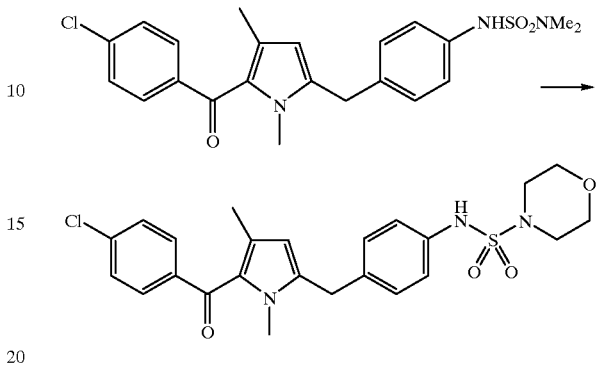

1-(4-[5-(4-Chlorobenzoyl)-1,4-dimethyl-1H-pyrrol-2-ylmethyl]phenyl}-3,3-di-methylsulfamide (75 mg, 0.188 mmol) and triethylamine (0.047 ml, 0.376 mmol) were dissolved in benzene (0.4 ml). The reaction mixture was stirred for 15 min and then concentrated in vacuo. The yellow solid residue was redissolved in 1.0 ml of morpholine and heated at 65° C. for 24 h. The reaction mixture was partitioned between ethyl acetate and 5% aqueous HCl. The organic layer was separated, washed with water, and brine, and dried over sodium sulfate. Crystallization of the crude product from hexane-ethyl acetate gave 1-{4-[5-(4-chlorobenzoyl)-1,4-dimethyl-1H-pyrrol-2-ylmethyl]phenyl}-3-sulfa-morpholide (49 mg, 53%) as a solid, mp 126–127° C.

Example 25

Synthesis of N-2-hydroxy-4-[5-(4-chlorobenzoyl-1,4-dimethyl-1H-pyrrol-2-yl-methyl]phenyl}methanesulfonamide

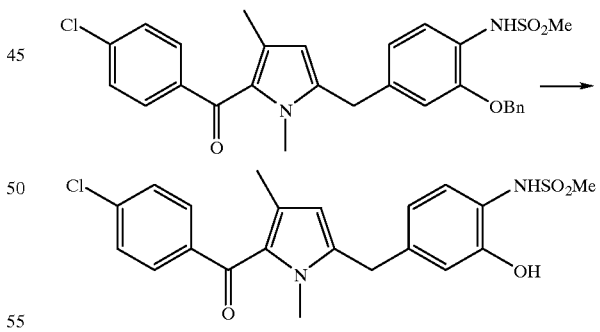

N-{2-Benzyloxy-4-[5-(4-chlorobenzoyl-1,4-dimethyl-1H-pyrrol-2-ylmethyl]phenyl}-methanesulfonamide (0.31 g, 0.59 mmol) was dissolved in ethyl acetate (50 ml). 10% Pd/C (93 mg) was added and the mixture was stirred under $H_2$ atmosphere for 2h. The mixture was filtered through Celite® and the filtrate was evaporated to give a solid. Crystallization from hexane-acetone gave N-{2-hydroxy-4-[5-(4-chlorobenzoyl-1,4-dimethyl-1H-pyrrol-2-yl-methyl]phenyl}-methanesulfonamide (200 mg, 78%) as a solid, mp 205° C. (dec.).

Example 26

Synthesis of N-{3-carboxy-4-[5-(4-chlorobenzoyl)-1,4-dimethyl-1H-pyrrol-2-yl-methyl]phenyl}methanesulfonamide

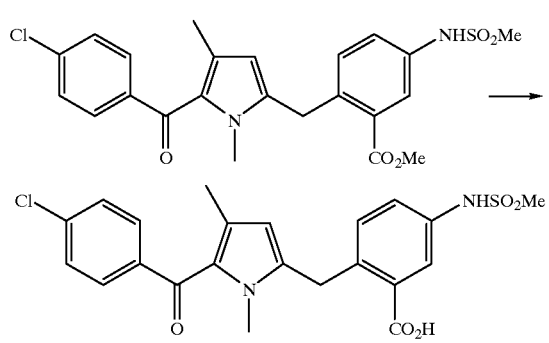

N-{3-Methoxycarbonyl-4-[5-(4-chlorobenzoyl)-1,4-dimethyl-1H-pyrrol-2-yl-methyl]phenyl}methanesulfonamide (735 mg, 1.54 mmol) and 2.5 N sodium hydroxide (2.5 ml) were dissolved in a 1:1 mixture of methanol-THF (40 ml) and stirred at room temperature for 64 h. The mixture was diluted with water, acidified to pH 2 with 2.0 N HCl, and extracted with ethyl acetate. The organic extracts were washed with brine, dried over sodium sulfate and concentrated to dryness. Crystallization from methylene chloride-methanol gave N-3-carboxy-4-[5-(4-chlorobenzoyl)-1,4-dimethyl-1H-pyrrol-2-ylmethyl]phenyl}-methanesulfonamide (500 mg, 70%) as a solid, mp 248–250° C. (dec.).

Example 27

Synthesis of N-{3-cyano-4-[5-(4-methylbenzoyl)-1-methyl-1H-pyrrol-2-yl-methyl]-phenyl}methanesulfonamide

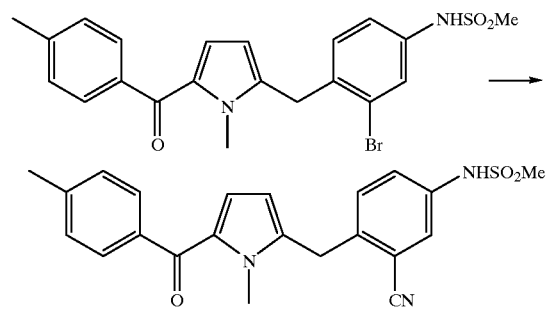

N-{3-Bromo-4-[5-(4-methylbenzoyl)-1-methyl-1H-pyrrol-2-ylmethyl]phenyl}methanesulfonamide (320 mg, 0.69 mmol) was dissolved in DMF. CuCN (120 mg, 1.38 mmol) was added and the suspension was refluxed for 4 h. The mixture was cooled to room temperature, and NaCN (2.0 g in 10 ml of water) was added. After 0.5 h the mixture was extracted with ethyl acetate and the extracts were washed with water, and brine, and dried over sodium sulfate. The solvent was removed in vacuo and the residue was purified by preparatory TLC (hexane-ethyl acetate) to give N-{3-cyano-4-[5-(4-methylbenzoyl)-1-methyl-1H-pyrrol-2-yl-methyl]phenyl}methanesulfonamide (190 mg, 67%) as a solid, mp 171–172° C.

Example 28

Synthesis of 3-fluoro-4-[5-benzoyl-1,4-dimethyl-1H-pyrrol-2-ylmethyl]aniline

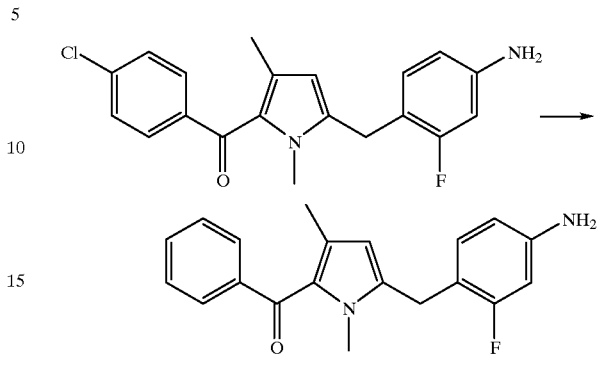

3-Fluoro-4-[5-(4-chlorobenzoyl)-1,4-dimethyl-1H-pyrrol-2-ylmethyl]aniline (5.0 g, 14.0 mmol), sodium acetate (1.15 g, 14 mmol) and 10% Pd/C (475 mg) were suspended in ethanol (230 ml). The reaction mixture was shaken in a Parr apparatus under hydrogen atmosphere at 30 psi overnight. The mixture was filtered through Celite® and the filtrate was evaporated to dryness. The crude product was purified on a silica gel column (methylene chloride-methanol, 99:1) and then crystallized from ethyl acetate/hexane/cyclohexane to give 3-fluoro-4-[5-benzoyl-1,4-dimethyl-1H-pyrrol-2-yl-methyl]aniline (2.49 g, 55%) as a solid.

Example 29

Synthesis of 3-fluoro-4-[5-(4-methylthiobenzoyl)-1,4-dimethyl-1H-pyrrol-2-ylmethyl]aniline

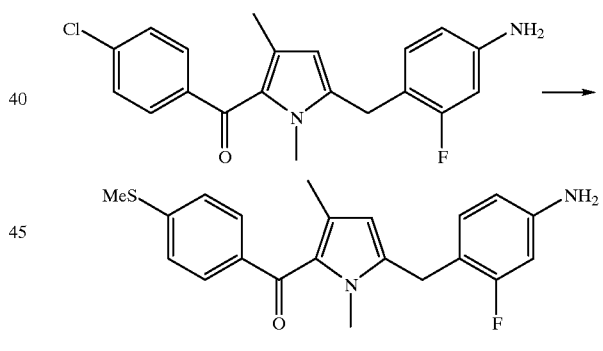

3-Fluoro-4-[5-(4-chlorobenzoyl)-1,4-dimethyl-1H-pyrrol-2-ylmethyl]aniline (2.0 g, 5.6 mmol) was dissolved in degassed DMF. Sodium thiomethoxide (1.5 g, 22.4 mmol) was added and the mixture stirred at room temperature under argon for 24 h. The reaction was poured into ice-water, acidified with acetic acid to pH 3 and extracted with ethyl acetate. The organic extracts were washed with water, and brine, and dried over magnesium sulfate. The solvent was removed in vacuo and the crude product was purified on a silica gel column (methylene chloride-methanol-acetone, 96:2:2) to give 3-fluoro-4-[5-(4-methylthiobenzoyl)-1,4-dimethyl-1H-pyrrol-2-ylmethyl]aniline (1.13 g, 55%) as a solid, mp 199.1–199.7° C.

Example 30

The following are representative pharmaceutical formulations containing a compound of formula I.

Tablet formulation
The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule formulation
The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension formulation
The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable formulation
The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Topical formulation
A topical formulation is prepared with the following ingredients.

| Ingredient | Amount, g |
|---|---|
| compound of this invention | 10 |
| Span 60 | 2 |
| TWEEN ® 60 | 2 |
| mineral oil | 5 |
| petrolatum | 10 |
| methyl paraben | 0.15 |
| propyl paraben | 0.05 |
| BHA (butylated hydroxy anisole) | 0.01 |
| water | q.s. to 100 |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
|---|---|
| compound of the invention | 500 mg |
| Witepsol ® H-15 | balance |

Example 31

Inhibition of COX I and COX II in vitro

The COX I and COX II inhibitory activity of compounds of this invention in vitro was determined using partially purified COX I and COX II enzymes, prepared as described in J. Barnett et al., *Biochim. Biophys. Acta*, 1209:130–139 (1994).

COX I and COX II samples were diluted with Tris-HCl buffer (50 mM Tris-HCl, pH 7.9) containing 2 mM EDTA and 10% glycerol and reconstituted by incubating first with 2 mM phenol for 5 minutes and then with I micromolar hematin for an additional 5 minutes. 125 $\mu$l of the reconstituted COX I or COX II enzyme were preincubated for 10 minutes at room temperature in a shaking water bath with the compounds of the invention dissolved in 2–15 $\mu$l of DMSO or the carrier vehicles (control samples). The enzyme reaction was initiated by adding 25 $\mu$l of 1-[14C] arachidonic acid (80,000–100,000 cpm/tube; 20 micromolar final concentration) and the reaction was allowed to continue for an additional 45 seconds. The reaction was terminated by adding 100 $\mu$l of 2 N HCl and 750 $\mu$l water. An aliquot (950 $\mu$l) of the reaction mixture was loaded onto a 1 ml $C_{18}$ Sep-Pak column (J. T. Baker, Phillipsburg, N.J.) which had been previously washed with 2–3 ml methanol and equilibrated with 5–6 ml distilled water. Oxygenated products were quantitatively eluted with 3 ml of acetonitrile/water/acetic acid (50:50:0.1, v/v) and the radioactivity in the eluate determined in a scintillation counter.

Compounds of this invention were active in this assay.

The COX inhibitory activities (expressed as $IC_{50}$, the concentration causing 50% inhibition of the COX enzyme being assayed) of some compounds of the invention and indomethacin as a comparator, were:

| CPD# | COX I $IC_{50}$, $\mu$M | COX II $IC_{50}$, $\mu$M | CPD# | COX I $IC_{50}$, $\mu$M | COX II $IC_{50}$, $\mu$M |
|---|---|---|---|---|---|
| 1 | 11 | 0.15 | 206 | 0.46 | 0.24 |
| 11 | 7.5 | 0.51 | 222 | 0.46 | 0.074 |
| 19 | 0.76 | 0.08 | 223 | 0.064 | 0.029 |
| 27 | 415 | 0.063 | 226 | 100 | 2.1 |
| 28 | 33 | 0.19 | 227 | 2.5 | 0.1 |
| 31 | 3.9 | 0.045 | 228 | 8.5 | 0.1 |
| 36 | 10 | 0.05 | 235 | 8.2 | 0.17 |
| 38 | 0.27 | 0.065 | 236 | 15 | 0.51 |
| 48 | 61 | 0.08 | 243 | 100 | 8.9 |
| 60 | 0.16 | 0.028 | 250 | 34 | 27.4 |
| 63 | 0.035 | 0.33 | 251 | 310 | 0.64 |
| 66 | 6.9 | 0.12 | 263 | 49 | 0.45 |
| 68 | 0.86 | 0.073 | 267 | 210 | 0.7 |
| 71 | 38 | 0.16 | 271 | 89 | 0.43 |
| 72 | 265 | 0.7 | 272 | >1000 | 2.1 |
| 88 | <0.1 | 0.06 | 276 | 60 | 0.5 |
| 95 | 0.09 | 0.06 | 284 | 22 | 0.50 |
| 97 | <0.1 | 0.038 | 288 | 235 | 0.55 |
| 98 | <0.1 | 0.23 | 289 | 10.2 | 1.5 |
| 104 | 0.75 | 0.24 | 294 | 9.1 | 2.6 |
| 106 | 0.95 | 0.07 | 295 | 0.60 | 0.10 |
| 131 | 0.20 | 0.077 | 296 | 0.21 | 0.40 |
| 133 | 0.045 | 0.058 | 306 | 113 | 0.64 |

-continued

| CPD# | COX I IC$_{50}$, μM | COX II IC$_{50}$, μM | CPD# | COX I IC$_{50}$, μM | COX II IC$_{50}$, μM |
|---|---|---|---|---|---|
| 140 | 5.4 | 0.12 | 308 | 650 | 8.75 |
| 141 | 3.9 | 003 | 310 | 142 | 9.2 |
| 146 | 29 | 0.06 | 314 | 65 | 0.56 |
| 147 | 0.6 | 0.1 | 316 | 360 | 0.20 |
| 154 | 34 | 0.054 | 329 | 256 | 43.7 |
| 165 | 16.8 | 0.095 | 330 | 61.1 | 30 |
| 172 | 43 | 0.09 | 333 | NA | 78.4 |
| 177 | 0.79 | 0.30 | 334 | 18.3 | 0.64 |
| 196 | 5.0 | 0.04 | 340 | 0.02 | 0.06 |
| 197 | <0.1 | 0.07 | 343 | 6.6 | 0.54 |
| 202 | 3.2 | 0.05 | Indo-methacin | 0.4 | 14 |

Example 32

Anti-inflammatory Activity

The anti-inflammatory activity of compounds of this invention was determined by measuring the inhibition of carrageenan-induced paw edema in the rat, using a modification of the method described in Winter C. A. et al. (1962) "Carrageenan-Induced Edema in Hind Paw of the Rat as an Assay for Anti-inflammatory Drugs." Proc. Soc. Exp. Biol. Med. 111: 544–547. This assay has been used as a primary in vivo screen for anti-inflammatory activity of most NSAIDs, and is considered predictive of human efficacy. Briefly, test materials were administered orally to female rats in a volume of 1 ml prepared as solutions or suspensions in an aqueous vehicle containing 0.9% NaCl, 0.5% sodium carboxymethyl-cellulose, 0.4% polysorbate 80, 0.9% benzyl alcohol and 97.3% distilled water. Control rats received vehicle alone. After 1 h 0.05 ml of a 0.5% solution of Carrageenan (Type IV Lambda, Sigma Chemical Co.) in 0.9% saline was injected into the subplantar region of the right hind paw Three hours later the rats were euthanized in a carbon dioxide atmosphere; hind paws were removed by severing at the tatso-crural joint; and the left and right paws were weighed. The increase in weight of the right paw over the left paw was obtained for each animal and the mean increases were calculated for each group. The anti-inflammatory activity of the test materials is expressed as the percent inhibition of the increase in hind paw weight of the test group relative to the vehicle-dosed control group.

Compounds of this invention were active in this assay.

The anti-inflammatory activities (expressed as % inhibition) of some of the compounds of the invention at 10 mg/Kg were:

| CPD# | % Inhibition | CPD# | % Inhibition |
|---|---|---|---|
| 19 | 36 | 146 | 40 |
| 36 | 31 | 165 | 17 |
| 48 | 35 | 263 | 40 |
| 98 | 42 | 288 | 20 |
| 140 | 27 | 343 | 35 |

Example 33

Inhibition of Eicosanoid Synthesis in vivo

The activity of compounds of this invention in inhibiting in vivo eicosanoid (prostaglandin E$_2$) synthesis in inflamed tissues was determined by the carrageenan-induced inflammation (air-pouch model) in rats, using a modification of the method described in Futaki, M., et al.; (1993) "Selective Inhibition of NS-398 on prostanoid production in inflamed tissue in rat Carrageenan Air-pouch Inflammation," J. Pharm. Pharmacol. 45:753–755, and Masferrer, J. L., et al.; (1994) "Selective Inhibition of inducible cyclooxygenase 2 in vivo is Antiflammatory and Nonulcerogenic," Proc. Natl. Acad. Sci. USA. 91: 3228–3232. In this assay, an air-pouch is created in the rat and the PGE$_2$ levels in the air-pouch exudate are measured by enzyme immunoassay. Briefly, male rats were anesthetized using a 60:40 CO$_2$:O$_2$ mixture and subsequently injected subcutaneously with 20 ml of sterilized air, under aseptic conditions, in the proximal area of the dorsum. This injection of sterile air causes the creation of a subcutaneous "air pouch". The next day, a further 10 ml of sterile air was injected into the previously formed pouch using the same technique. The test materials were administered orally in a volume of 1 ml/100 g body weight as solutions or suspensions in an aqueous vehicle containing 0.9% NaCl, 0.5% sodium carboxymethyl-cellulose, 0.4% polysorbate 80, 0.9% benzyl alcohol and 97.3% water. Control rats received vehicle alone. After 30 minutes, 5 ml of a 0.5% solution of arrageenan (Sigma, Lambda Type IV) was injected into the air pouch. The rats were euthanized 3 or 6 h after the compound administration. 10 ml of a solution containing 10 μg/l of indomethacin and 5.4 mM EDTA in 0.9% sterile saline was injected into the air pouch; the air pouch was cut open; and the exudate was harvested. The total exudate volume was recorded, and the samples were analyzed for PGE$_2$ and 6-keto PGF$_1$ by ELISA (Titerzyme®, PerSeptive Diagnostics) and TxB$_2$ by radio-immuno assay (New England Nuclear Research, Catalog No. NEK-037), according to the manufacturer's directions.

The mean concentrations of PGE$_2$ were calculated for each group. The anti-inflammatory activity of test materials is expressed as the percent inhibition of PGE$_2$ formation in the test group relative to the control group.

Compounds of this invention were active in this assay.

The anti-inflammatory activities (expressed as % inhibition of air pouch PGE$_2$ formation) of some of the compounds of this invention and indomethacin as a comparator were:

| CPD# | Dose mg/Kg | % Inhibition | Time |
|---|---|---|---|
| 19 | 10 | 74% | 3 hr |
| 36 | 10 | 96% | 3 hr |
| 48 | 30 | 64% | 3 hr |
| 98 | 10 | 98% | 3 hr |
| 140 | 30 | 83% | 6 hr |
| 146 | 10 | 93% | 3 hr |
| 165 | 10 | 52% | 3 hr |
| 236 | 30 | 71% | 6 hr |
| 263 | 30 | 80% | 6 hr |
| 271 | 10 | 56% | 3 hr |
| 284 | 10 | 65% | 3 hr |
| 288 | 10 | 53% | 3 hr |
| 334 | 10 | 44% | 3 hr |
| Indomethacin | 2–5 | >70% | |

Example 34

Analgesic Activity

The analgesic activity of compounds of this invention may be determined by the Acetic Acid-induced Rat Writhing Assay, using a modification of the method described in Berkenkopf, J. W. and Weichman, B. M. "Production of Prostacyclin in Mice following Intraperitoneal Injection of Acetic Acid, Phenylbenzoquinone and Zymosan: Its Role in the Writhing Response," *Prostaglandins*: 36: 693–70 (1988). This assay is one of several acute assays which have been used to assess the analgesic activity of NSAIDs, and is considered predictive of human efficacy. The test materials were administered orally to male Sprague Dawley rats in a volume of 1 ml/100 g body weight as solutions or suspensions in an aqueous vehicle containing 0.9% NaCl, 0.5% sodium carboxymethyl-cellulose, 0.4% polysorbate 80, 0.9% benzyl alcohol and 97.3% water. Control rats received vehicle alone. One hour after compound administration, 0.3 ml/100 g body weight of 0.75% solution of acetic acid was injected intraperitoneally. The acetic acid injection induces a series of characteristic writhing responses, which were counted over the period between 15 and 30 minutes after the injection. The analgesic activity of test materials is expressed as the percentage inhibition of writhing in the test group relative to the control group.

Compounds of this invention were active in this assay. The analgesic activities (expressed as % inhibition of writhing responses) of some of the compounds of this invention at 10 mg/Kg were:

| CPD# | % Inhibition | CPD# | % Inhibition |
|------|--------------|------|--------------|
| 36   | 16           | 140  | 4            |
| 98   | 71           | 263  | 31           |

The analgesic activity of compounds of this invention may also be determined using an adjuvant-induced arthritis pain model in the rat, where pain is assessed by the animal's vocal response to the squeezing or flexing of an inflamed ankle joint, as described in Winter C. A. and Nuss, G. W. (1966) "Treatment of Adjuvant Arthritis in rats with Anti-inflammatory Drugs," *Arthritis Rheum*. 9: 394–403 and Winter, C. A., Kling P. J., Tocco, D. J., and Tanabe, K. (1979). "Analgesic activity of Diflunisal [MK-647; 5-(2,4-Difluorophenyl)salicylic acid] in Rats with Hyperalgesia Induced by Freund's Adjuvant" *J. Pharmacol. Exp. Ther*. 211: 678–685.

What is claimed is:

1. A compound selected from the group of compounds represented by formula I:

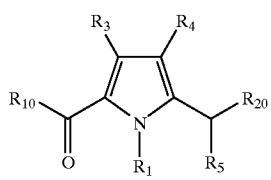

where:

$R_1$ and $R_5$ together are —$(CH_2)_2$— or —$(CH_2)_3$—;

$R_3$ and $R_4$ are independently H, halo, alkyl, alkyloxy, or alkylthio;

$R_{10}$ is a group represented by formula (A), (B) or (C):

(A)
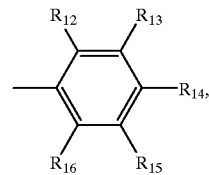

(B)
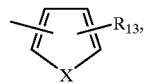

or (C)
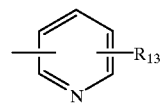

where:
X is O or S;
$R_{12}$ and $R_{16}$ are independently H, halo, alkyl, alkyloxy, alkylthio, cyano, or hydroxy;
$R_{13}$ and $R_{15}$ are independently H, halo, alkyl, alkyloxy, or alkylthio; and
$R_{14}$ is H, halo, alkyl, haloalkyl, amino, alkylamino, dialkylamino, alkyloxy, hydroxy, alkylthio, alkenyl, alkynyl, cyano, —$SO_2R_{17}$ where $R_{17}$ is alkyl, or —$SO_2NR_{18}R_{19}$ where $R_{18}$ and $R_{19}$ are independently H or alkyl;
provided that at least two of $R_{12}$, $R_{13}$, $R_{14}$, $R_{15}$ and $R_{16}$ are H, and that if only two of $R_{12}$, $R_{13}$, $R_{14}$, $R_{15}$, and $R_{16}$ are H, the non-hydrogen substituents are not all adjacent; or
$R_{12}$, $R_{15}$, and $R_{16}$ are H and $R_{13}$ and $R_{14}$ together are —$OCH_2O$—;

$R_{20}$ is a group represented by formula (U), (V) or (W):

(U)
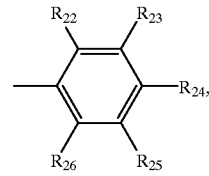

(V)
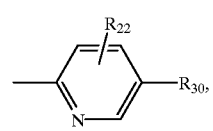

or (W)
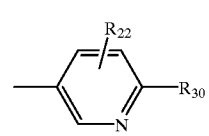

where:
$R_{22}$ is H, halo, alkyl, cyano, trifluoromethyl, hydroxy, alkyloxy, or —$CO_2R_{27}$ where $R_{27}$ is H or alkyl;

one of $R_{23}$, $R_{24}$, and $R_{25}$ is $R_{30}$; and either all the remaining $R_{23}$, $R_{24}$, $R_{25}$, and $R_{26}$ are H; or one of the remaining $R_{23}$, $R_{24}$, $R_{25}$, and $R_{26}$ is halo, alkyl, cyano, trifluoromethyl, hydroxy, or alkyloxy; and $R_{30}$ is —OH*, —NHH*, —NH*CHO, —NH*C(X)$R_{31}$, —NH*SO$_2$R$_{31}$, —NH*C(X)NR$_{32}$R$_{33}$, or —NH*SO$_2$NR$_{32}$R$_{34}$, where:

H* is hydrogen, optionally replaced by an in vivo hydrolyzable protecting group;

$R_{31}$ is alkyl, haloalkyl, hydroxyalkyl, alkenyl, benzyl, aryl, cycloamino, —CH$_2$SO$_2$Me, or —(CH$_2$)$_n$R$_{35}$, where n is an integer from 2 to 5 and $R_{35}$ is alkylamino, dialkylamino, cycloamino, alkyloxy, acyloxy, or —CO$_2$R$_{27}$;

$R_{32}$ is H, alkyl, or —(CH$_2$)$_n$OR$_{27}$;

$R_{33}$ is H, alkyl, haloalkyl, aryl, hydroxyalkyl, tetrahydrofuran-2-ylmethyl, —CH$_2$CO$_2$R$_{27}$, or —(CH$_2$)$_n$R$_{35}$; and $R_{34}$ is H, alkyl, acetyl, hydroxyalkyl, or —(CH$_2$)$_n$R$_{35}$;

and their pharmaceutically acceptable salts.

2. The compound of claim 1 where $R_{20}$ is a group represented by formula (U) or (V) and $R_{24}$ is $R_{30}$.

3. The compound of claim 2 where $R_{10}$ is a group represented by formula (A).

4. The compound of claim 3 where $R_3$ is H or alkyl; $R_4$, $R_{15}$, and $R_{16}$ are H; and $R_{13}$ is H, halo, or alkyl.

5. The compound of claim 4 where $R_{30}$ is —NHH*, —NH*SO$_2$R$_{31}$, or —NH*SO$_2$NR$_{32}$R$_{34}$.

6. The compound of claim 5 where $R_3$ is H or Me; $R_{13}$ is H; and $R_{14}$ is H, halo, alkyl, alkylthio, or alkoxy.

7. The compound of claim 6 where $R_{12}$ is H, F, Cl, Me, OMe, or OH; and $R_{14}$ is H, F, Cl, Me, OMe, or SMe.

8. The compound of claim 7 where $R_{20}$ is a group represented by formula (U); $R_{23}$ and $R_{25}$ are H; and $R_{22}$ and $R_{26}$ are independently H, halo, or cyano.

9. The compound of claim 8 where $R_{14}$ is H, Me, Cl or OMe; and $R_{22}$ and $R_{26}$ are independently H, F, Cl, or CN.

10. The compound of claim 9 where $R_{26}$ is H.

11. The compound of claim 10 where $R_{30}$ is —NH*SO$_2$R$_{31}$.

12. The compound of claim 11 where $R_{31}$ is alkyl, hydroxyalkyl, or —(CH$_2$)$_n$R$_{35}$.

13. The compound of claim 12 where $R_{31}$ is Me or 2-hydroxyethyl.

14. The compound of claim 10 where $R_{30}$ is —NH*SO$_2$NR$_{32}$R$_{34}$.

15. The compound of claim 10 where $R_{30}$ is —NHH*.

16. A pharmaceutical composition comprising a therapeutically effective amount of a compound of claim 1 and a pharmaceutically acceptable excipient.

17. A method of treating an inflammatory disease or an autoimmune disease in a mammal by inhibiting prostaglandin G/H synthase comprising administration to the mammal of a therapeutically effective amount of a compound of claim 1.

* * * * *